(12) United States Patent
Sumiya et al.

(10) Patent No.: US 7,470,738 B2
(45) Date of Patent: Dec. 30, 2008

(54) NON-AQUEOUS ABSORBENT AND USE THEREOF

(75) Inventors: Takashi Sumiya, Kyoto (JP); Kazuya Ohtani, Kyoto (JP); Takeaki Yamaguchi, Kyoto (JP); Youji Fujiura, Kyoto (JP)

(73) Assignee: Sanyo Chemical Industries, Ltd., Kyoto (JP)

( * ) Notice: Subject to any disclaimer, the term of this patent is extended or adjusted under 35 U.S.C. 154(b) by 765 days.

(21) Appl. No.: 10/499,840

(22) PCT Filed: Dec. 24, 2002

(86) PCT No.: PCT/JP02/13471

§ 371 (c)(1),
(2), (4) Date: Jun. 22, 2004

(87) PCT Pub. No.: WO03/057745

PCT Pub. Date: Jul. 17, 2003

(65) Prior Publication Data

US 2005/0136247 A1 Jun. 23, 2005

(30) Foreign Application Priority Data

| Dec. 27, 2001 | (JP) | ............................ 2001-396347 |
| Apr. 23, 2002 | (JP) | ............................ 2002-120323 |
| Apr. 23, 2002 | (JP) | ............................ 2002-120360 |
| Apr. 26, 2002 | (JP) | ............................ 2002-125646 |
| May 20, 2002 | (JP) | ............................ 2002-144194 |
| Jul. 22, 2002 | (JP) | ............................ 2002-212251 |
| Oct. 1, 2002 | (JP) | ............................ 2002-288764 |
| Oct. 24, 2002 | (JP) | ............................ 2002-309174 |
| Nov. 5, 2002 | (JP) | ............................ 2002-321540 |
| Nov. 11, 2002 | (JP) | ............................ 2002-326452 |
| Nov. 11, 2002 | (JP) | ............................ 2002-326888 |

(51) Int. Cl.
*C08G 18/66* (2006.01)
*B32B 5/16* (2006.01)

(52) U.S. Cl. ........................ 524/356; 428/327; 428/403; 525/329.7; 525/330.3; 525/333.3; 526/286; 526/317.1; 526/318.4

(58) Field of Classification Search ................ 526/286, 526/317.1, 318.4; 524/356; 428/327, 403; 525/329.7, 330.3, 333.3
See application file for complete search history.

(56) References Cited

U.S. PATENT DOCUMENTS

| 4,132,695 | A | * | 1/1979 | Burkholder | .................. 524/547 |
| 4,879,117 | A | * | 11/1989 | Rombi | ...................... 424/411 |
| 4,997,656 | A | * | 3/1991 | Shikinami et al. | ........... 424/448 |
| 6,244,265 | B1 | * | 6/2001 | Cronk et al. | ........... 128/200.24 |

FOREIGN PATENT DOCUMENTS

| JP | 62-262735 | | 11/1987 |
| JP | 5-325986 | | 12/1993 |
| JP | 05325986 | A * | 12/1993 |
| JP | 6-166726 | | 6/1994 |
| JP | 06166726 | A * | 6/1994 |

* cited by examiner

*Primary Examiner*—Randy Gulakowski
*Assistant Examiner*—Michael M Bernshteyn
(74) *Attorney, Agent, or Firm*—Baker & Daniels LLP

(57) ABSTRACT

A non-aqueous absorbent comprising a crosslinked polymer which contains a structural unit having a carboxyl group and/or a sulfonate group in an amount of 20 to 100% weight in its molecule and in which from 30 to 100% by mol of the protons in the carboxyl group and/or the sulfonate group have been substituted by onium cations; a non-aqueous gel made of this non-aqueous absorbent and an organic solvent; and a non-aqueous absorbent sheet and a non-aqueous absorbent agent containing the non-aqueous absorbent. Because of having excellent capabilities of absorbing and holding various organic solvents such as alcohols and gelating, these materials are usable for various purposes, for example, lithium batteries, alcohol-based bactericidal materials or alcohol-based bactericides, cold insulating materials or cold insulators, gel sheets for cooling, fuel compositions for solid fuels or solid fuels using the same, fragrance materials or fragrances, patch materials or patches, insecticidal compositions or insecticides, fuel stores for fuel batteries or fuel batteries using the same.

18 Claims, No Drawings

NON-AQUEOUS ABSORBENT AND USE THEREOF

TECHNICAL FIELD

The present invention relates to a non-aqueous absorbent comprising a crosslinked body having a particular composition, and a non-aqueous absorbing gel, a non-aqueous absorbing sheet and a non-aqueous absorbent agent using the same. More particularly, the present invention relates to a non-aqueous absorbent having extremely high capabilities of absorbing and gelating an organic solvent, and a form such as a non-aqueous absorbing gel, a non-aqueous absorbing sheet, a non-aqueous absorbent agent and the like, as well as various uses employing them.

BACKGROUND TECHNIQUE

Previously, a crosslinked sodium polyacrylate salt has been used as a water-absorbing resin in a variety of utilities. However, in this composition, an amount of absorbing water or urine is high, but a resin is not swollen at all in an organic solvent. Therefore, the resin is not applied as an agent for absorbing an organic solvent or as a gelating agent.

As a crosslinked resin which absorbs an organic solvent, for example, there are proposed:

(1) a crosslinked polymer of a monomer containing a tertiary or quaternary amino group such as dialkylaminoalkyl (meth)acrylate, (meth)acryloyltrialkylammonium chloride and the like (JP-A No. 58-154709 gazette), (2) an alcohol absorbent comprising a crosslinked copolymer of the aforementioned tertiary amino group-containing monomer and a vinyl monomer having a carboxyl group (JP-A No. 60-179410 gazette, JP-A No. 60-192717 gazette etc.), (3) an oil absorbent comprising crosslinked (meth)acrylate of a monovalent aliphatic alcohol having a carbon number of 10 to 16 or a crosslinked monomer having a solubility parameter of 9 or smaller (JP-A No. 3-221582 gazette, JP-No. 4-100539 gazette etc.), (4) a liquid-absorbing resin comprising crosslinked alkoxyalkyl (meth)acrylate and the like or crosslinked N-vinyllactam (JP-A No. 10-101745 gazette, JP-A No. 11-35632 gazette etc.), (5) a liquid-absorbing resin comprising crosslinked N-vinylacetamide (JP-A No. 4-230250 gazette, JP-A No. 8-59743 gazette).

In addition, in the fields of lithium batteries and condensers, a polar organic solvent such as propylene carbonate and γ-butyrolactone is usually used as an electrolyte solution. In order to make a battery thin or to prevent solution leakage at damage, there is a great demand for gelating this organic solvent. As a polymer for gelating an electrolyte solution, for example, there are proposed:

(6) crosslinked polyalkylene oxide (hereinafter, referred to as PEO system, JP-A No. 62-285954 gazette, JP-A No. 6-68906 gazette and many publications), (7) crosslinked polyacrylnitrile (hereinafter, referred to as PAN system, JP-A No. 8-264205 gazette, JP-A No. 2000-58078 gazette, JP-A No. 2000-223105 gazette etc.), (8) crosslinked polyacrylic acid ester, and a method of using a polymer having the same composition as that of the (1) as a gelating agent for an electrolyte solution (JP-A No. 2000-331533 gazette, 2001-123073 gazette etc.).

However, although the crosslinked polymer of (1) exhibits a relatively high amount of absorbing an alcohol, the polymer has a low amount of absorbing an organic solvent other than an alcohol, for example, propylene carbonate, γ-butyrolactone, toluene and the like, and at the same time, an ester group of this kind of cationic polymer is extremely easily degraded at a region of a pH 4 or larger due to intramolecular interaction between an amino group and an ester group, and therefore, there is a problem that the polymer is not suitable for utilities requiring durability of a polymer, such as a gelating agent for an electrolyte solution.

In addition, regarding crosslinked polymers of (3) to (8), since these polymers are fundamentally a nonionic polymer, dissociation of a polymer does not occur in the aforementioned subject organic solvents. Therefore, those polymers have weak capabilities of absorbing and gelating subject organic solvents and, in order to absorb and gelate these organic solvents, it becomes necessary to add a large amount of a polymer. There is a problem that not only this is uneconomical, but also when used in utilities such as batteries and condensers, addition of a large amount of a polymer reduces an electrical conductivity of an electrolyte solution, and deteriorates electrical properties.

Further, lithium batteries and condensers are used in mobile phones, computers, various appliance products and the like. However, there is a problem that, when an organic solvent-based electrolyte solution is leaked, a harmful gas is generated, substrates of other ICs and semiconductors are polluted, and ignition occurs in some cases. Regarding prevention of leakage of these electrolyte solutions, only a non-woven fabric sheet is practically proposed. The non-woven fabric has an extremely small solution holding amount to these electrolyte solutions. When there is a great leakage, this can not be defended at all. Therefore, there is a great demand for development of a sheet which can hold a large amount of these organic solvents.

In view of the aforementioned circumstances, the present inventors intensively studied, and as a result, found that a non-aqueous absorbent comprising a crosslinked body having a particular composition has extremely high capabilities of absorbing and gelating the aforementioned organic solvents, a large amount of organic solvents can be absorbed and gelated by addition of a small amount of the non-aqueous absorbent, and a sheet containing the non-aqueous absorbent has an extremely high amount of holding the aforementioned organic solvents, and can hold a large amount of those organic solvents, which resulted in completion of the present invention.

An object of the present invention is to provide a non-aqueous absorbent which has extremely high capabilities of absorbing and gelating organic solvents, and can absorb a large amount of organic solvent and gelate organic solvents by addition of a small amount of the same.

Another object of the present invention is to provide various uses of this non-aqueous absorbent in various forms.

SUMMARY OF THE INVENTION

That is, the present invention is a non-aqueous absorbent (B) comprising a crosslinked polymer (1) (A) which contains a structural unit having a carboxyl group and/or a sulfonate group in an amount of 20 to 100% by weight in its molecule and in which from 30 to 100% by mol of the protons in the carboxyl group and/or the sulfonate group have been substituted by onium cations; a form of non-aqueous gel (C), a non-aqueous absorbent sheet (D) and a non-aqueous absorbent agent (E) made of the (B); as well as uses of an alcohol-based bactericidal material or an alcohol-based bactericide, a cold insulating material or a cold insulator, a gel sheet for cooling, a fuel composition for solid fuels or a solid fuel using the same, a fragrance material or a fragrance, a patch material or a patch, an insecticidal composition or an insecticide, a fuel store for fuel batteries or a fuel battery using the same, or a lithium battery or the like.

BEST MODE FOR CARRYING OUT THE INVENTION

The non-aqueous absorbent (B) of the present invention is characterized in that it comprises a crosslinked polymer (1) (A) which contains a predetermined amount of a structural unit having a carboxyl group and/or a sulfonate group in its molecule, and in which protons of the carboxyl group and/or the sulfonate group are substituted with a predetermined amount of onium cations, for the purpose of absorbing gelating subject organic solvents. That is, the non-aqueous absorbent (B) of the present invention comprises a crosslinked polymer (1) (A) which contains a structural unit having a carboxyl group and/or a sulfonate group in an amount of 20 to 100% by weight in its molecule, and in which from 30 to 100% by mole of protons of the carboxyl group and/or the sulfonate group are substituted with onium cations.

Examples of a monomer (a') constituting a structural unit (a) having a carboxyl group and/or a sulfonate group include carboxyl group-containing monomers [e.g. (meth)acrylic acid, (eth)acrylic acid, crotonic acid, sorbic acid, maleic acid, itaconic acid, fumaric acid, cinnamic acid, and anhydride thereof etc.]; sulfonate group-containing monomers [e.g. aliphatic vinyl sulfonic acid [vinyl sulfonic acid, allylsulfonic acid, vinyl toluenesulfonic acid, styrenesulfonic acid, etc.], (meth)acrylate-type sulfonic acid [sulfoethyl(meth)acrylate, sulfopropyl(meth)acrylate etc.] and (meth)acryl amide-type sulfonic acid [acrylamido-2-methylpropanesulfonic acid etc.]], and one or more of them may be polymerized to obtain a structural unit (a) in the polymer (1). Preferable is a structural unit having a carboxyl group and/or a sulfonate group having a carbon number of 3 to 30.

In addition, examples of a method of obtaining a polymer (1) containing a predetermined amount of a structural unit having a carboxyl group and/or a sulfonate group in its molecule include, in addition to the method of polymerizing a predetermined amount of a monomer (a') constituting the structural unit (a), a method of polymerizing a monomer which can be easily converted into a carboxyl group and/or a sulfonate group such as an ester and an amide of the carboxyl group and/or sulfonate group-containing monomer, and introducing a predetermined amount of a structural unit of a carboxyl group or a sulfonate group into a molecule using such as a hydrolyzing method, and a method of obtaining a carboxyl group or sulfonate group-containing polysaccharide polymer, a representative of which is carboxymethylcellulose, or a graft copolymer of the polysaccharide and other monomer. However, such the method is not particularly limited as long as a polymer containing a predetermined amount of a structural unit of a carboxyl group and/or a sulfonate group is finally obtained.

In the present invention, it is necessary that a content of the polymer (1) of a structural unit (a) having a carboxyl group and/or a sulfonate group is 20 to 100% by weight, preferably 40 to 100% by weight, more preferably 60 to 100% by weight based on a weight of the polymer (1). When the content is smaller than 20% by weight, an amount of absorbing a subject organic solvent is reduced, or a subject organic solvent can not be gelated at a small amount in some cases, even when protons of carboxylic acid or sulfonic acid are substituted with onium cations described later.

In the present invention, examples of a copolymerizable monomer (b') constituting a structural unit other than a structural unit (a) having a carboxyl group and/or a sulfonate group include alkyl(meth)acrylate (carbon number 1 to 30) esters [methyl(meth)acrylate, ethyl(meth)acrylate, propyl(meth)acrylate, butyl(meth)acrylate, ethylhexyl(meth)acrylate, octyl(meth)acrylate, dodecyl(meth)acrylate, stearyl(meth)acrylate, cyclohexyl(meth)acrylate, etc.]; oxyalkyl(meth)acrylates (carbon number 1 to 4) [hydroxyethyl(meth)acrylate, hydroxypropyl(meth)acrylate, (meth)acrylate mono(polyethylene glycol)ester [polyethlene glycol (hereinafter, referred to as PEG) number average molecular weight: 100 to 4,000], (meth)acrylic acid mono(polypropylene glycol)ester [polypropylene glycol (hereinafter, referred to as PPG) number average molecular weight: 100 to 4,000], (meth)acrylic acid monomethoxy polyethylene glycol (PEG number average molecular weight: 100 to 4,000), (meth)acrylic acid monomethoxy propylene glycol (PPG number average molecular weight: 100 to 4,000) etc.], (meth)acrylamides [(meth)acrylamide, (di)methyl(meth)acrylamide, (di)ethyl(meth)acrylamide, (di)propyl(meth)acrylamide etc.]; allyl ethers [methyl allyl ether, ethyl allyl ether, propyl allyl ether, glycerol monoallyl ether, trimethylolpropane triallyl ether, pentaerythritol monoallyl ether, etc.]; α-olefins having a carbon number of 4 to 20 [isobutylene, 1-hexene, 1-octene, iso-octene, 1-nonene, 1-decene, 1-dodecene etc.]; aromatic vinyl compounds having a carbon number of 8 to 20 [styrene, t-butylstyrene, octylstyrene etc.]; other vinyl compounds [N-vinylacetamide, vinyl caproate, vinyl laurate, vinyl stearate etc.], amino group-containing monomers [dialkyl(carbon number of alkyl: 1 to 5)aminoethyl(meth)acrylate, meth(acryloyl)oxyethyltrialkyl(carbon number of alkyl: 1 to 5)ammonium chloride, bromide or sulfate etc.] and alkali metal salts, primary to tertiary amine salts or alkanolamine salts of the aforementioned monomers having a carboxyl group or a sulfonate group. It is preferable that one or more of these monomers (b') is (are) copolymerized with the (a') in a range of a predetermined amount (smaller than 80% of polymer structural unit) as necessary.

From a viewpoint of polymerizability of a monomer and stability of the produced polymer, among the aforementioned monomers (b'), alkyl(meth)acrylate esters, oxyalkyl(meth)acrylates, allyl ethers, α-olefins, and aromatic vinyl compounds are preferable.

In addition, since the present invention is aimed at absorbing and gelating various organic solvents, it is preferable to select such a monomer (b') that a difference between a SP value (solubility parameter) of an organic solvent and that of a monomer (b') is 5 or smaller, depending on a SP value of a subject organic solvent because an absorbing amount and a gelating capability are easily increased. It is more preferable to select such a monomer (b') that a difference of a SP value of a subject organic solvent and that of the monomer (b') is 3 or smaller.

In the present invention, it is essential that from 30 to 100% by mol of protons of the carboxyl group and/or the sulfonate group are substituted with onium cations.

The onium cation is one or more selected from the group consisting of quaternary ammonium cation (I), tertiary sulfonium cation (II), quaternary phosphonium cation (III) and tertiary oxonium cation (IV).

Examples of the quaternary ammonium cation (I) include the following (I-1) to (I-11) (hereinafter, cation is omitted).

(I-1) Aliphatic quaternary ammoniums having an alkyl and/or alkenyl group having a carbon number of 4 to 30 or more;

tetramethylammonium, ethyltrimethylammonium, diethyldimethylammonium, triethylmethylammonium, tetraethylammonium, trimethylpropylammonium, dimethylpropylammonium, ethylmethyldipropylammonium, tetrapropylammonium, butyltrimethylammonium, dimethyldibutylammonium, tetrabutylammonium, etc.;

(I-2) Aromatic quaternary ammoniums having a carbon number of 6 to 30 or more; trimethylphenylammonium, dimethylethylphenylammonium, triethylphenylammonium, etc.;

(I-3) Alicyclic quaternary ammoniums having a carbon number of 3 to 30 or more; N,N-dimethylpyrrolidinium, N-ethyl-N-methylpyrrolidinium, N,N-diethylpyrrolidinium, N,N-dimethylmorpholinium, N-ethyl-N-methylmorpholinium, N,N-diethylmorpholinium, N,N-dimethylpiperidinium, N,N-diethylpiperidinium etc.;

(I-4) Imidazoliniums having a carbon number of 3 to 30 or more;

1,2,3-trimethylimidazolinium, 1,2,3,4-tetramethylimidazolinium, 1,3,4-trimethyl-2-ethylimidazolinium, 1,3-dimethyl-2,4-diethylimidazolinium, 1,2-dimethyl-3,4-diethylimidazolinium, 1,2-dimethyl-3-ethylimidazolinium, 1-ethyl-3-methylimidazolinium, 1-methyl-3-ethylimidazolinium, 1,2,3,4-tetraethylimidazolinium, 1,2,3-triethylimidazolinium, 4-cyano-1,2,3-trimethylimidazolinium, 2-cyanomethyl-1,3-dimethylimidazolinium, 4-acetyl-1,2,3-trimethylimidazolinium, 3-acetylmethyl-1,2-dimethylimidazolinium, 4-methylcarboxymethyl-1,2,3-trimethylimidazolinium, 3-methoxy-1,2-dimethylimidazolinium, 4-formyl-1,2,3-trimethylimidazolinium, 4-formyl-1,2-dimethylimidazolinium, 3-hydroxyethyl-1,2,3-trimethylimidazolinium, 3-hydroxyethyl-1,2-dimethylimidazolinium, etc.;

(I-5) Imidazoliums having a carbon number of 3 to 30 or more;

1,3-dimethylimidazolium, 1-ethyl-3-methylimidazolium, 1-methyl-3-ethylimidazolium, 1,2,3-trimethylimidazolium, 1,2,3,4-tetramethylimidazolium, 1,3-dimethyl-2-ethylimidazolium, 1,2-dimethyl-3-ethylimidazolium, 1-ethyl-3-methylimidazolium, 1-methyl-3-ethylimidazolium, 1,2,3-triethylimidazolium, 1,2,3,4-tetraethylimidazolium, 1,3-dimethyl-2-phenylimidazolium, 1,3-dimethyl-2-benzylimidazolium, 1-benzyl-2,3-dimethylimidazolium, 4-cyano-1,2,3-trimethylimiddazolium, 3-cyanomethyl-1,2-dimethylimidazolium, 4-acetyl-1,2,3-trimethylimidazolium, 3-acetylmethyl-1,2-dimethylimidazolium, 4-carboxymethyl-1,2,3-trimethylimidazolium, 3-methylcarboxymethyl-1,2-dimethylimidazolium, 4-methoxy-1,2,3-trimethylimidazolium, 4-formyl-1,2,3-trimethylimidazolium, 3-formylmethyl-1,2-dimethylimidazolium, 3-hydroxyethyl-1,2-dimethylimidazolium, 2-hydroxyethyl-1,3-dimethylimidazolium, N,N'-dimethylbenzimidazolium, N,N'-diethylbenzimidazolium, N-methyl-N'-ethylbenzimidazolium, etc.;

(I-6) Tetrahydropyrimidinium having a carbon number of 4 to 30 or more;

1,3-dimethyltetrahydropyrimidinium, 1,2,3-trimethyltetrahydropyrimidinium, 1,2,3,4-tetramethyltetrahydropyrimidinium, 8-methyl-1,8-diazabicyclo[5,4,0]-7-undecenium, 5-methyl-1,5-diazabicyclo[4,3,0]-5-nonenium, 4-cyano-1,2,3-trimethyltetrahydropyrimidinium, 3-cyanomethyl-1,2-dimethyltetrahydropyrimidinium, 4-acetyl-1,2,3-trimethyltetrahydropyrimidinium, 3-acetylmethyl-1,2-dimethyltetrahydropyrimidinium, 4-methylcarboxymethyl-1,2,3-trimethyl-tetrahydropyrimidinium, 4-methoxy-1,2,3-trimethyltetrahydropyrimidinium, 3-methoxymethyl-1,2-dimethyltetrahydropyrimidinium, 4-hydroxymethyl-1,2,3-trimethyltetrahydropyrimidinium, 4-hydroxymethyl-1,3-dimethltetrahydropyrimidinium, etc.;

(I-7) Dihydropyrimidiniums having a carbon number of 4 to 30 or more;

1,3-dimethyl-2,4- or -2,6-dihydropyrimidinium, [these are expressed by 1,3-dimethyl-2,4,(6)-dihydropyrimidinium, and the similar expression is used hereinafter], 1,2,3-trimethyl-2,4,(6)-dihydropyrimidinium, 1,2,3,4-tetramethyl-2,4,(6)-dihydropyrimidinium, 1,2,3,5-tetramethyl-2,4,(6)-dihydropyrimidinium, 8-methyl-1,8-diazacyclo[5,4,0]-7,9(10)-undecadienium, 5-methyl-1,5-diazacyclo[4,3,0]-5,7(8)-nonadienium, 2-cyanomethyl-1,3-dimethyl-2,4,(6)-dihydropyrimidinium, 3-acetylmethyl-1,2-dimethyl-2,4,(6)-dihydropyrimidinium, 4-methylcarboxymethyl-1,2,3-trimethyl-2,4,(6)-dihydropyrimidinium, 4-methoxy-1,2,3-trimethyl-2,4,(6)-dihydropyrimidinium, 4-formyl-1,2,3-trimethyl-2,4,(6)-dihydropyrimidinium, 3-hydroxyethyl-1,2-dimethyl-2,4,(6)-dihydropyrimidinium, 2-hydroxyethyl-1,3-dimethyl-2,4,(6)-dihydropyrimidinium, etc.;

(I-8) Guanidiums having an imidazolinium skeleton having a carbon number of 3 to 30 or more;

2-dimethylamino-1,3,4-trimethylimidazolinium, 2-diethylamino-1,3,4-trimethylimidazolinium, 2-diethylamino-1,3-dimethyl-4-ethylimidazolinium, 2-dimethylamino-1-methyl-3,4-diethylimidazolinium, 2-diethylamino-1,3,4-triethylimidazolinium, 2-dimethylamino-1,3-dimethylimidazolinium, 2-diethylamino-1,3-dimethylimidazolinium, 2-diethylamino-1,3-diethylimidazolinium, 1,5,6,7-tetrahydro-1,2-dimethyl-2H-imido[1,2a]imidazolinium, 1,5,6,7-tetrahydro-1,2-dimethyl-2H-pyrimido[1,2a]imidazolinium, 1,5-dihydro-1,2-dimethyl-2H-pyrimido[1,2a]imidazolinium, 2-dimethyl-3-cyanomethyl-1-methylimidazolinium, 2-dimethylamino-3-methylcarboxymethyl-1-methylimidazolinium, 2-dimethylamino-4-formyl-1,3-dimethylimidazolinium, 2-dimethylamino-3-hydroxyethyl-1-methylimidazolinium, 2-dimethylamino-4-hydroxymethyl-1,3-dimethylimidazolinium, etc.;

(I-9) Guanidiums having an imidazolium skeleton having a carbon number of 3 to 30 or more;

2-dimethylamino-1,3,4-trimethylimidazolium, 2-diethylamino-1,3,4-trimethylimidazolium, 2-diethylamino-1,3-dimethyl-4-ethylimidazolium, 2-diethylamino-1-methyl-3,4-diethylimidazolium, 2-diethylamino-1,3,4-triethylimidazolium, 2-diemethylamino-1,3-dimethylimidazolium, 2-dimethylamino-1-ethyl-3-methylimidazolium, 2-diethylamino-1,3-diethylimidazolium, 1,5,6,7-tetrahydro-1,2-dimethyl-2H-imido[1,2a]imidazolium, 1,5,6,7-tetrahydro-1,2-dimethyl-2H-pyrimido[1,2a]imidazolium, 1,5-dihydro-1,2-dimethyl-2Hpyrimido-[1,2a]imidazolium, 2-dimethylamino-3-cyanomethyl-1-methylimidazolium, 2-dimethylamino-acetyl-1,3-dimethylimidazolium, 2-dimethylamino-4-methylcarboxymethyl-1,3-dimethylimidazolium, 2-dimethylamino-4-methoxy-1,3-dimethylimidazolium, 2-dimethylamino-3-methoxymethyl-1-methylimidazolium, 2-dimethylamino-3-formylmethyl-1-methylimidazolium, 2-dimethylamino-4-hydroxymethyl-1,3-dimethylimidazolium etc.;

(I-10) Guanidiums having a tetrahydropyrimidinium skeleton having a carbon number of 4 to 30 or more;

2-dimethylamino-1,3,4-trimethyltetrahydropyrimidinium, 2-diethylamino-1,3,4-trimethyltetrahydropyrimidinium, 2-diethylamino-1,3-dimethyl-4-ethyltetrahydropyrimidinium, 2-diethylamino-1-methyl-3,4-diethyltetrahydropyrimidinium, 2-dimethylamino-1,3-dimethyltetrahydropyrimidinium, 2-diethylamino-1,3- dimethyltetrahydropyrimidinium, 2-diethylamino-1,3-diethyltetrahydropyrimidinium, 1,3,4,6,7,8-hexahydro-1,2-dimethyl-2H-imido[1,2a]pyrimidinium, 1,3,4,6,7,8-hexahydro-1,2-dimethyl-2H-pyrimido[1,2a]pyrimidinium, 2,3,4,6-tetrahydro-1,2-dimethyl-2H-pyrimido[1,2a]pyrimidinium, 2-dimethylamino-3-cyanomethyl-1-methyltetrahydropyrimidinium, 2-dimethylamino-4-acetyl-1,3-dimethyltetrahydropyrimidinium, 2-dimethylamino-4-methylcarboxymethyl-1,3-dimethyltetrahydropyrimidinium, 2-dimethylamino-3-methylcarboxymethyl-1-methyltetrahydropyrimidinium, 2-dimethylamino-3-methoxymethyl-1-methyltetrahydropyrimidinium, 2-dimethylamino-4-formyl-1,3-dimethyltetrahydropyrimidinium, 2-dimethylamino-3-hydroxyethyl-1-methyltetrahydropyrimidinium, 2-dimethylamino-4-hydroxymethyl-1,3-dimethyltetrahydropyrimidinium etc.;

(I-11) Guanidiums having a dihydropyrimidinium skeleton having a carbon number of 4 to 30 or more;

2-dimethylamino-1,3,4-trimethyl-2,4(6)-dihydropyrimidinium, 2-diethylamino-1,3,4-trimethyl-2,4(6)-dihydropyrimidinium, 2-dimethylamino-1-methyl-3,4-diethyl-2,4(6)-dihydropyrimidinium, 2-diethylamino-1-methyl-3,4-diethyl-2,4(6)-dihydropyrimidinium, 4-diethylamino-1,3,4-triethyl-2,4(6)-dihydropyrimidinium, 2-diethylamino-1,3-dimethyl-2,4(6)-dihydropyrimidinium, 2-diethylamino-1,3-dimethyl-2,4(6)-dihydropyrimidinium, 2-dimethylamino-1-ethyl-3-methyl-2,4(6)-dihydropyrimidinium, 1,6,7,8-tetrahydro-1,2-dimethyl-2H-imido[1,2a]pyrimidinium, 1,6-dihydro-1,2-dimethyl-2H-imido[1,2a]pyrimidinium, 1,6-dihydro-1,2-dimethyl-2H-pyrimido[1,2a]pyrimidinium, 2-dimethylamino-4-cyano-1,3-dimethyl-2,4(6)-dihydropyrimidinium, 2-dimethylamino-4-acetyl-1,3-dimethyl-2,4(6)-dihydropyrimidinium, 2-dimethylamino-3-acetylmethyl-1-methyl-2,4(6)-dihydropyrimidinium, 2-dimethylamino-3-methylcarboxymethyl-1-methyl-2,4(6)-dihydropyrimidinium, 2-dimethylamino-4-methoxy-1,3-dimethyl-2,4(6)-dihydropyrimidinium, 2-dimethylamino-4-formyl-1,3-dimethyl-2,4(6)-dihydropyrimidinium, 2-dimethylamino-3-formylmethyl-1-methyl-2,4(6)-dihydropyrimidinium, 2-dimethylamino-4-hydroxymethyl-1,3-dimethyl-2,4(6)-dihydropyrimidinium etc.

Examples of the tertiary sulfonium cation (II) include the following (II-1) to (II-3):

(II-1) Aliphatic tertiary sulfoniums having an alkyl and/or alkenyl group having a carbon number of 1 to 30 or more;

trimethylsulfonium, triethylsulfonium, ethyldimethylsulfonium, diethylmethylsulfonium etc.;

(II-2) Aliphatic tertiary sulfoniums having a carbon number of 6 to 30 or more;

phenyldimethylsulfonium, phenylethylmethylsulfonium, phenylmethylbenzylsulfonium etc.;

(II-3) Alicyclic tertiary phosphoniums having a carbon number of 3 to 30 or more;

methylthiolanium, phenylthiolanium, methylthianium etc.

Examples of the quaternary phosphonium cation (III) include the following (III-1) to (III-3):

(III-1); Aliphatic quaternary phosphoniums having an alkyl and/or alkenyl group having a carbon number of 1 to 30 or more;

tetramethylphosphonium, tetraethylphosphonium, tetrapropylphosphonium, tetrabutylphosphonium, methyltriethylphosphonium, methyltripropylphosphonium, methyltributylphosphonium, dimethyldiethylphosphonium, dimethyldipropylphosphonium, dimethyldibutylphosphonium, trimethylethylphosphonium, trimethylpropylphosphonium, trimethylbutylphosphonium etc.;

(III-2) Aromatic quaternary phosphoniums having a carbon number of 6 to 30 or more;

triphenylmethylphosphonium, diphenyldimethylphosphonium, triphenylbenzylphosphonium etc.;

(III-3) Alicyclic quaternary phosphoniums having a carbon number of 3-30 or more;

1,1-dimethylphosphoranium, 1-methyl-1-ethylphosphoranium, 1,1-diethylphosphoranium, 1,1-dimethylphosphorynanium, 1-methyl-1-ethylphosphorinanium, 1,1-diethylphosphorinanium, 1,1-pentaethylenephosphorinanium etc.

Examples of the tertiary oxonium cation (IV) include the following (IV-1) to (IV-3):

(IV-1) Aliphatic tertiary oxoniums having an alkyl and/or alkenyl group having a carbon number of 1 to 30 or more;

trimethyloxonium, triethyloxonium, ethyldimethyloxonium, diethylmethyloxonium etc.;

(IV-2) Aromatic tertiary oxoniums having a carbon number of 6 to 30 or more;

phenyldimethyloxonium, phenylethylmethyloxonium, phenylmethylbenzyloxonium etc.;

(IV-3) Alicyclic tertiary oxoniums having a carbon number of 3 to 30 or more;

methyloxolanium, phenyloxolanium, methyloxanium etc.

Among them, preferable onium cation is (I), more preferable are (I-1), (I-4) and (I-5), and further preferable are (I-4) and (I-5).

These onium cations may be used alone or in combination of two or more.

In the present invention, examples of a method of introducing an onium cation into a polymer include a method of substituting protons of a carboxyl group and/or a sulfonate group of a polymer with the onium cations. As the method of substituting protons with the onium cations, any methods may be used as long as they are a method which can substitute a predetermined amount with the onium cations. For example, protons can be easily substituted by adding a hydroxide salt (e.g. tetraethylammonium hydroxide etc.) or a monomethylcarbonate salt (e.g. 1,2,3,4-trimethylimidazolinium monomethylcarbonate salt etc.) of the onium cation to a polymer containing a carboxyl group and/or a sulfonate group, and performing dehydration, decarbonization or demethanolation as necessary. Alternatively, substitution may be performed similarly at a stage of a monomer.

Regarding a stage of substitution with the onium cations, examples include a method of polymerization after a monomer containing the carboxyl group and/or the sulfonate group is substituted with the onium cations, and a method of substituting protons of an acid with the onium cations after a polymer having a carboxyl group and/or a sulfonate group is prepared, but substitution may be performed at any stage as long as protons of a carboxyl group and/or a sulfonate group of a final polymer are substituted.

In the present invention, an degree of substitution (substitution degree) of protons of a carboxyl group and/or a sulfonate group with the onium cations is different variously depending on utility of a final product (e.g. utility such as non-aqueous absorbent sheet or non-aqueous absorbent agent, gelating agent of an electrolyte solution etc.), but a substitution degree is necessary to be 30 to 100% by mol, preferably 50 to 100% by mol, more preferably 70 to 100% by mol. In addition, when utility is a gelating agent of a lithium battery containing a lithium salt, it is particularly preferable that a substitution degree is as high as 90 to 100% by mol from a viewpoint of reduction in active protons.

When a substitution degree by the onium cations is smaller than 30% by mol, dissociation of a carboxyl group and a sulfonate group of a polymer (1) and an onium cation is too low, therefore, swelling capability and gelating capability are low, and electric properties are reduced due to too much active protons, in some cases, depending on utility.

In the present invention, the polymer (I) which contains a predetermined amount of a structural unit having a carboxyl group and/or a sulfonate group and in which the carboxyl group and/or the sulfonate group is substituted with a predetermined amount of onium cations, is finally crosslinked to obtain a crosslinked body.

A crosslinking method may be the known method, and examples include the following (i) to (v) methods:

(i) Crosslinking with copolymerizing crosslinking agent;

A method of performing crosslinking by copolymerizing the carboxyl group and/or sulfonate group-containing monomer (a'), the monomer substituted with an onium cation and, if necessary, a copolymerizing crosslinking agent which is copolymerizable with other copolymerizable monomer (b') or has two or more double bonds in a molecule [multivalent vinyl-type crosslinking agent such as divinylbenzene etc., (meth)acrylamide-type crosslinking agent such as N,N'-methylenebisacrylamide etc., multivalent allyl ether-type crosslinking agent such as pentaerythritol triallyl ether etc., multivalent (meth)acrylic acid ester-type crosslinking agent such as trimethylolpropane triacrylate etc., etc.].

(ii) Crosslinking with a reactive crosslinking agent;

A method of performing crosslinking using a monomer having a carboxyl group and/or a sulfonate group or the group substituted with an onium cation and, if necessary, a reactive crosslinking agent having two or more functional groups which can react with a functional group of a copolymerizable monomer, in a molecule [multivalent isocyanate-type crosslinking agent such as 4,4'-diphenylmethane diisocyanate etc., multivalent epoxy-type crosslinking agent such as polyglycelol polyglycidyl ether etc., polyhydric alcohol-type crosslinking agent such as glycerin etc., multivalent amine or imine-type crosslinking agent such as hexamethylenetetramine and polyethyleneimine etc., haloepoxy-type crosslinking agent such as epichlorohydrin etc., multivalent metal salt-type crosslinking agent such as aluminum sulfate etc., etc.].

(iii) Crosslinking with polymerization reactive crosslinking agent;

A method of performing crosslinking using the carboxyl group and/or sulfonate group-containing monomer (a'), the monomer substituted with an onium cation, a monomer which is copolymerizable with other monomer (b') to be copolymerized if necessary, or has a double bond in a molecule, and has a carboxyl group and/or a sulfonate group or the group substituted with an onium cation, and a polymerization reactive crosslinking agent having a functional group which can react with a functional group of a monomer to be copolymerized if necessary, in a molecule [glycidyl (meth) acrylate-type crosslinking agent of glycidyl methacrylate etc., allylepoxy-type crosslinking agent such as allyl glycidyl ether etc., etc.].

(iv) Crosslinking with irradiation;

A method of crosslinking a polymer (1) by irradiating the polymer (1) with radiation such as ultraviolet-ray, electron beam, γ-ray or the like, and a method of performing polymerization and crosslinking at the same time by irradiating the monomer with radiation such as ultraviolet-ray, electron beam, γ-ray or the like.

(v) Crosslinking with heating

A method of performing thermal intermolecular crosslinking of a polymer (1) by heating the polymer (1) at 100° C. or higher [crosslinking between carbons or crosslinking between functional groups by generation of a radical by heating].

Among these crosslinking methods, a preferable method is different depending on use and a form of a final product, and is (i) (ii) (iv) from an overall viewpoint.

Among the aforementioned copolymerizing crosslinking agents, preferable are a (meth)acrylamide-type crosslinking agent, a multivalent allyl ether-type crosslinking agent, and a multivalent (meth)acrylic acid ester-type crosslinking agent, and more preferable is a multivalent allyl ether-type crosslinking agent.

Among the aforementioned reactive crosslinking agents, preferable are a multivalent isocyanate-type crosslinking agent and a multivalent epoxy-type crosslinking agent, and more preferable is a multivalent isocyanate-type crosslinking agent or a multivalent epoxy-type crosslinking agent, which has 3 or more functional groups in a molecule.

A crosslinking degree can be appropriately selected depending on a use purpose. When a copolymerizing crosslinking agent is used, an amount of the crosslinking agent is preferably 0.001 to 10% by weight, more preferably 0.01 to 5% by weight relative to a total monomer weight.

When a reactive crosslinking agent is used, a preferable addition amount is different depending on a kind of a product to be made utilizing the crosslinked body of the present invention and, when a non-aqueous absorbent sheet or a non-aqueous absorbent agent described later is made, an amount is preferably 0.001 to 10% by weight based on a total polymer weight. When an integrated gel containing an organic solvent described later is made, an amount is preferably 0.01 to 50% by weight.

In the present invention, a method of polymerizing the carboxyl group and/or sulfonate group-containing monomer, the monomer substituted with an onium cation, and other monomer (b') to be copolymerized if necessary may be the known method, and examples include a solution polymerization method in which polymerization is performed in a solvent capable of dissolving the aforementioned respective monomers and the produced polymer, a bulk polymerization method of performing polymerization without using a solvent, an emulsion polymerization method and the like. Among them, preferable is a solution polymerization method.

An organic solvent in solution polymerization can be appropriately selected depending on a solubility of a monomer and a polymer used, and examples include alcohols such as methanol, ethanol and the like, carbonates such as ethylene carbonate, propylene carbonate, dimethylene carbonate and the like, lactones such as γ-butyrolactone and the like, lactams such as ε-caprolactam and the like, ketones such as acetone, methyl ethyl ketone and the like, carboxylic acid esters such as ethyl acetate and the like, ethers such as tetrahydrofuran, dimethoxyethane and the like, aromatic hydrocarbons such as toluene, xylene and the like, and water. These solvents may be used alone, or by mixing two or more.

The polymerization concentration in solution polymerization is not particularly limited, and is different variously depending on a use purpose, but is preferably 1 to 80% by weight, more preferably 5 to 60% by weight.

A polymerization initiator may be a normal initiator, and examples include azo-based initiators [azobisisobutylonitrile, azobiscyanovaleric acid, azobis(2,4-dimethyl)valeronitrile], azobis(2-amidinopropane)dihydrochloride, azobis{2-methyl-N-(2-hydroxyethyl)propionamide} etc.), peroxide-based initiators [benzoyl peroxide, di-t-butyl peroxide, cumene hydroperoxide, succinic acid peroxide, di(2-ethoxyethyl)peroxy dicarbonate, hydrogen peroxide etc.], and redox initiators [combination of the aforementioned peroxide-based initiator and a reducing agent (ascorbic acid or persulfate salt) etc.].

Examples of other polymerization method include a method of adding a photosensitive initiator [benzophenone etc.] and irradiating ultraviolet-ray, and a method of performing polymerization by irradiating radiation such as γ-ray and electron beam.

An amount of an initiator to be added when a polymerization initiator is used is not particularly limited, but is preferably 0.0001 to 5% by weight, more preferably 0.001 to 2% by weight relative to a total weight of monomers used.

A polymerization temperature is different variously depending on a desired molecular weight, a degradation temperature of an initiator, and a boiling point of a solvent used, and is preferably −20 to 200° C., more preferably 0 to 100° C.

The non-aqueous absorbent (B) of the present invention comprises the thus obtained crosslinked body (A), and can be processed into various forms depending on a purpose, being not limiting. Examples of a preferable form include particulate and sheet-like forms.

A method of making a preferable form will be explained below, but since a making method and a preferable method are slightly different depending on a form, each of them will be explained.

(Form)

When the non-aqueous absorbent (B) comprising the crosslinked body (A) of the present invention is formulated into particulate, a particle diameter as an average particle diameter is preferably 1 to 5,000 μm, more preferably 50 to 2,000 μm.

A method of obtaining a particulate form is not particularly limited as long as a particulate form is obtained finally, but examples include the following (i) to (iv) methods.

(i) A method of copolymerizing the aforementioned copolymerizing crosslinking agent using, if necessary, a solvent to prepare a non-aqueous absorbent (B) comprising a crosslinked polymer (1) (A) and, if necessary, distilling off a solvent by a method such as drying, and grinding using the known grinding method to obtain a particulate form.

(ii) A method of performing polymerization to prepare a polymer (1), and if necessary, using a solvent, crosslinking the polymer (1) by means of the aforementioned reactive crosslinking agent or irradiation and the like, and if necessary, distilling off a solvent by a method such as drying or the like, and grinding this using the known grinding method to obtain a particulate form.

(iii) A method of copolymerizing the aforementioned carboxyl group and/or sulfonate group-containing monomer (a'), and if necessary, other monomer (b') in the presence of the aforementioned copolymerizing crosslinking agent, if necessary, using a solvent to obtain a crosslinkied polymer, adding the aforementioned onium cation compound to substitute protons of an acid group with a predetermined amount of onium cations, and if necessary, distilling off a solvent by a method such as drying or the like, and grinding this using the known grinding method to obtain a particulate form.

(iv) A method of copolymerizing the aforementioned carboxyl group and/or sulfonate group-containing monomer (a'), and if necessary other monomer (b') in the presence of the aforementioned copolymerizing crosslinking agent, if necessary, using a solvent without crosslinking to obtain a polymer, crosslinking the polymer with the aforementioned onium cation compound and reactive crosslinking agent or irradiation at the same time with substituting protons of an acid group, and if necessary, distilling off a solvent by a method such as drying or the like, and grinding this using the known grinding method to obtain a particulate form.

Drying which is performed, if necessary, during a process of rendering particulate a shape of a non-aqueous absorbent (B) comprising the aforementioned crosslinked body (A) may be the known drying method, and examples include ventilation drying (circulating wing drier etc.), gas permeating drying (band-type drier etc.), vacuum drying (vacuum drier etc.), contact drying (drum drier etc.) and the like.

A drying temperature when drying is performed is not particularly limited as long as deterioration of a polymer or excessive crosslinking does not occur, but is preferably 0 to 200° C., more preferably 50 to 150° C.

A grinding method when a shape is rendered particulate may be the known method and, examples include methods such as impact grinding (high speed rotating-type grinder such as pinmill, cutter mill, ball mill-type grinder and ACM pulverizer), air grinding (jet grinder etc.), and freezing grinding.

The non-aqueous absorbent (B) comprising the thus particulated crosslinked body (A) has capability of absorbing an organic solvent, and can be utilized as a non-aqueous absorbent agent (E).

A liquid holding amount of the non-aqueous absorbent (B) of the present invention varies variously depending on a kind of a subject organic solvent, a composition of the polymer, a gel strength, and the like. When the (B) is used as a non-aqueous absorbent agent (E), a liquid holding amount for an organic solvent selected from propylene carbonate, γ-butyrolactone, ethanol and methanol is designed at preferably 10 to 1,000 g/g, more preferably 50 to 900 g/g. When a liquid holding amount is 10 g/g or larger, a liquid holding amount is considerably larger as compared with previous non-ionic absorbent, and when a liquid holding amount is 1,000 g/g or smaller, there is not a problem that a gel strength of an absorbent agent holding an organic solvent is too weak.

Another invention of the present invention is a non-aqueous gel (C) comprising the aforementioned non-aqueous absorbent (B) and an organic solvent (2).

A ratio of the non-aqueous absorbent (B)/organic solvent in this non-aqueous gel (C) is preferably 0.1 to 99/1 to 99.9% by weight, more preferably 0.5 to 50/50 to 99.5% by weight, further preferably 1 to 30/70 to 99% by weight, most preferably 1 to 20/80 to 99% by weight. When a ratio of the (B) is 0.1% by weight or larger, a gel strength of the produced non-aqueous gel (C) is not weak, and a whole can be sufficiently gelated. When the ratio is 99.9% by weight or smaller, even if it is used for gelation of an electrolyte solution, an electrical conductivity of a gel is not reduced, and an amount of a necessary electrolyte solution or an electrolyte described later to be added is not too smaller, not leading to insufficient volume.

Examples of the organic solvent (2) used in the non-aqueous gel (C) of the present invention include the same organic solvents as those described above, and specific examples include alcohol organic solvents such as methanol, ethanol, propanol, butanol and the like, glycol organic solvents such as ethylene glycol, propylene glycol and the like, carbonate organic solvents such as dimethyl carbonate, ethylene carbonate, propylene carbonate and the like, ketone organic solvents such as acetone, dimethyl ketone, methyl ethyl ketone and the like, ether organic solvents such as diethyl ether, diethoxyethane, tetrahydrofuran, dioxane and the like, aliphatic hydrocarbon organic solvents such as hexane, octane and the like, aromatic hydrocarbon organic solvents such as toluene, xylene and the like, carboxylic acid ester organic solvents such as methyl acetate, ethyl acetate, propyl acetate and the like, lactone organic solvents such as γ-butyrolactone and the like, and lactam organic solvents such as ε-caprolactam and the like.

Among them, preferably organic solvents are propylene carbonate, ethylene carbonate, dimethyl carbonate, and dimethoxyethane which are a solvent for lithium batteries; γ-butyrolactone, and ε-caprolactum which are a solvent for a condenser; methanol, ethanol, and propanol which are a solvent for solid fuels or ignition agents; other toluene, xylene, propylene glycol and the like, and a mixture of two or more of them.

In the present invention, these organic solvents may be a solvent in which a salt of lithium as an electrolyte used in such as lithium batteries contained in the aforementioned organic solvent.

Examples of a kind of a preferable lithium salt contained in the aforementioned organic solvents include one or more kinds of $LiClO_4$, $LiBF_4$, $LiPH_6$, $LiAsF_6$, $LiCF_3SO_3$, and $Li(CF_8SO_2)_2$, and a more preferable salt is $L_1BF_4$ and/or $LiPH_6$.

A content of a lithium salt to be added as necessary can be selected variously depending on a purpose or necessity thereof, Li solubility and the like, and the salt is contained in the aforementioned organic solvent at preferably 0.5 to 50% by weight, more preferably 1 to 20% by weight.

In the present invention, since an organic solvent containing the lithium salt is used, and there is a possibility that a proton of the carboxyl group and/or sulfonate group reacts with a lithium salt, a substitution degree of a proton with an onium cation in this case is preferably 90 to 100% by mol, more preferably 98 to 100% by mol.

Examples of a method of preparing the non-aqueous gel (C) of the present invention include the following (v) to (viii), but it is preferable to prepare an integrated gel by methods exemplified in (vii) and (viii).

(v) A method of adding a predetermined amount of the organic solvent (2) to the aforementioned particualte non-aqueous absorbent (B) of the present invention;

(vi) A method of adding the organic solvent (2) to a sheet containing the non-aqueous absorbent (B);

(vii) A method of dissolving the polymer (1) in the organic solvent (2), and crosslinking the polymer (1) by any crosslinking means of crosslinking with the aforementioned linking agent, crosslinking by irradiation with ultraviolet-ray or radiation (electron beam, γ-ray etc.), and crosslinking by heating to obtain an integrated gel;

(viii) A method of obtaining an integrated gel by polymerizing 20 to 100% by weight of a carboxyl group and/or sulfonate group-containing monomer in which from 30 to 100% by mol of protons are substituted with the aforementioned onium cations, and if necessary, 0 to 80% by weight of other copolymerizable monomer in the organic solvent (2) in the presence of the aforementioned copolymerizing crosslinking agent.

A form of a gel comprising the non-aqueous absorbent (B) and the organic solvent (2) can be appropriately selected depending on a purpose and a utility. Examples of a shape include sheet-like, block-like, spherical and cylindrical shapes. Among them, a preferable shape is sheet-like or block-like and, in particular, when used in a gel battery for mobile phones or computers, sheet-like is preferable.

A thickness of a gel when formulated into a sheet-like gel is preferably 1 to 10,000 μm, more preferably 10 to 1,000 μm. A width and a length of a sheet-like gel may be appropriately selected depending on a use purpose, a use place, a utility and the like.

A method of preparing gels having these shapes is not particularly limited, but examples include a method of performing gelating in a container or a cell in conformity with a shape which is wanted to be prepared, and a method of preparing a sheet-gel by laminating or coating a mixture of the polymer (1), the monomer or the like and the organic solvent (2) on a releasing paper, a film, a non-woven fabric or the like.

Since the non-aqueous absorbent (B) or the non-aqueous absorbent agent (E) and/or the non-aqueous gel (C) of the present invention can gelate a large amount of an organic solvent for lithium batteries at a small amount of them, increase in a ratio of an electrolyte solution becomes possible, and as a result, since increase in ionic conductivity becomes possible, they can be suitably used as a gelating agent for lithium batteries.

Then, the case where the non-aqueous absorbent (B) of the present invention is shaped into a sheet will be explained.

The non-aqueous absorbent sheet (D) of the present invention comprises the aforementioned non-aqueous absorbent (B), and a substrate selected from the group consisting of a non-woven fabric, a woven fabric, a paper and a film.

Examples of a method of obtaining a sheet-like shape include the following (ix) to (xi) methods.

(ix) A method of holding the aforementioned particulate non-aqueous absorbent (B) between non-woven fabrics or papers to obtain a sandwich sheet.

(x) A method of impregnating and/or coating one or more substrates selected from the group consisting of a non-woven fabric, a woven fabric, a paper and a film with the uncrosslinked polymer (1), and then, crosslinking the polymer (1) using one or more crosslinking means selected from the group consisting of crosslinking with the aforementioned crosslinking agent, crosslinking by irradiation with ultraviolet-ray or radiation (electron beam, γ-ray etc.), and crosslinking by heating, and at the same time, if necessary, distilling off a solvent to obtain a sheet.

(xi) A method of impregnating and/or coating one or more substrates selected from the group consisting of a non-woven fabric, a woven fabric, a paper and a film with a mixed solution containing 20 to 100% by weight of a carboxyl group and/or a sulfonate group-containing monomer in which from 30 to 100% by mol of protons are substituted with the aforementioned onium cations, 0 to 80% by weight of other copolymerizable monomer and the aforementioned crosslinking agent, and then, polymerizing the substrate using one or more crosslinking means selected from the group consisting of crosslinking by a polymerization initiator and/or irradiation with ultraviolet-ray or radiation (electron beam, γ-ray etc.), and crosslinking by heating and, if necessary, distilling off a solvent to obtain a sheet.

Among these methods, it is preferable to use a method of (x) or (xi) from a viewpoint of easy adjustment of a thickness of a sheet and an absorbing rate.

A thickness when a shape is a sheet is preferably 1 to 5,000 μm, more preferably 5 to 2,000 μm, further preferably 10 to 1,000 μm. When a thickness of a sheet is 1 μm or larger, a basis amount of the non-aqueous absorbent (B) becomes insufficient and, when the thickness is 5,000 μm or smaller, a thickness of the sheet is sufficient.

A length and a width of a sheet are not particularly limited, and can be appropriately selected depending on a use purpose and a utility, but a preferable length is 0.01 to 10,000 m, and a preferable width is 0.1 to 300 cm.

A basis weight of the non-aqueous absorbent (B) of the present invention in the sheet is not particularly limited, but when capabilities of absorbing and holding a subject organic solvent, and not too large thickness are considered, a basis weight is preferably 10 to 3,000 g/m², more preferably 20 to 10,000 g/m².

In the present invention, a substrate such as a non-woven fabric, a woven fabric, a paper, a film and the like to be used if necessary to render a shape sheet-like may be the known-substrate, and examples include a non-woven fabric or a woven fabric composed of a synthetic fiber and/or a natural fiber having a basis weight of around 10 to 500 g/m², a paper (wood free paper, thin paper, Japanese paper etc.), a film composed of a synthetic resin, and a substrate of two or more of them, and a composite of them.

Among these substrate, preferable is a non-woven film, and a composite of a non-woven fabric and a film, and more preferably is a composite composed of a film having one side of a non-woven fabric and one side having no liquid-permeating property.

In the present invention, a thickness of these substrates is preferably 1 to 5,000 μm, more preferably 10 to 2,000 μm. When a thickness is 1 μm or larger, impregnation or coating with a predetermined amount of the polymer (1) becomes easy. On the other hand, when a thickness is 5,000 μm or smaller, a sheet is not too thick, and a sheet is easily used.

A method of coating or impregnating a substrate with the polymer (1) may be the known method. For example, normal methods such as coating and padding may be applied. After coating or padding treatment, a solvent used for polymerization, dilution or viscosity adjustment may be, if necessary, distilled off by a method such as drying or the like.

Since the thus prepared sheet containing the non-aqueous absorbent (B) of the present invention effectively absorbs an organic solvent, the sheet is used as a non-aqueous absorbent sheet (D), and is mainly used as a non-aqueous absorbent sheet or a leakage-preventing sheet for organic solvents or organic solvent electrolyte solutions in lithium primary batteries, secondary batteries, and condensers.

An absorbing amount of this non-aqueous absorbent sheet (D) is variously different depending on a use purpose, but a liquid-holding amount (absorbing amount after centrifugation dehydration) for propylene carbonate which is a representative solvent of a lithium battery is preferably 0.1 to 100 g/cm², preferably 1 to 100 g/cm². When a liquid-holding amount is 0.1 g/cm² or larger, an electrolyte solution can be sufficiently held, and when the amount is 100 g/cm² or smaller, a sheet which has absorbed an organic solvent does not become too thick.

In the present invention, the non-aqueous absorbent (B) can be used as a gel electrolyte for lithium batteries, but from a viewpoint of contact with an electro rode (interface), a sheet-like crosslinked body (A) which has absorbed an organic solvent containing the aforementioned lithium electrolyte, or an integrated non-aqueous gel (C) comprising the non-aqueous absorbent (B) and an organic solvent containing the aforementioned lithium electrolyte may be used as a gel electrolyte.

(Examples of Utilities)

From the foregoing, under the aforementioned various forms, the non-aqueous absorbent (B) of the present invention is useful in a wide range of utilities such as a leakage-preventing sheet and a liquid stop agent for electronic and electric appliances and automobile organic solvent batteries, condensers, capacitors and the like, an ignition agent, organic solvent batteries and gel electrolyte batteries of condensers, alcohol-based bactericidal materials or alcohol-based bactericides, cold insulating materials or cold insulators, gel sheets for cooling, fuel compositions for solid fuels or solid fuels using the same, fragrance materials or fragrances, patch materials or patches, insecticidal compositions or insecticides, or fuel stores for fuel batteries or fuel batteries using the same. In addition, in particular, the non-aqueous absorbent sheet (D) is useful in electrolyte solutions of lithium primary batteries, lithium secondary batteries or condensers.

Among the aforementioned utility examples, alcohol-based bactericidal materials or alcohol-based bactericides, cold insulating materials or cold insulators, gel sheets for cooling, fuel compositions for solid fuels or solid fuels using the same, fragrance materials and cold insulators, patch materials or patches, insecticidal compositions or insecticides, or fuel stores for fuel batteries or fuel batteries using the same will be described in detail below.

[Alcohol-Based Bactericidal Materials and Alcohol-Based Bactericides]

An alcohol-based bactericidal material comprising the non-aqueous absorbent (B) and an alcohol solvent, can be processed into various forms depending on a purpose. Examples of a preferable form include the aforementioned particulate, sheet-like, and integrated gelated forms, being not particularly limited. In the present invention, an alcohol solvent refers to a water-soluble alcohol alone which can be mixed with water at an arbitrary ratio, or a mixture of this and water. Preferable examples include a mixture of one or more alcohols selected from the group consisting of methanol, ethanol and isopropyl alcohol (hereinafter, abbreviated as IPA) and water, being not particularly limited. Particularly preferable is a mixture of ethanol and water.

An amount of absorbing an alcohol solvent of an alcohol-based bactericidal material is such that an amount of absorbing ethanol and/or methanol is designed at preferably 10 to 1,000 g/g, more preferably 50 to 900 g/g. When an absorbing amount is 10 g/g or larger, a liquid-holding amount is considerably larger as compared with the previous non-ionic absorbent. When the amount is 1,000 g/g or smaller, there is not a problem that a gel strength of an alcohol-based bactericidal material holding an alcohol solvent is too weak.

When a shape of an alcohol-based bactericidal material is formulated into a sheet, a shape is as described for the aforementioned non-aqueous absorbent (B) shaped into a sheet. That is, a thickness, a length and a width of a sheet; a substrate to be used, and a basis weight are as described above. However, among substrates, preferable are a non-woven fabric, and a composite of a non-woven fabric, a plastic film and a metal film, and more preferable is a composite having one surface composed of a non-woven fabric, and another surface composed of a plastic film and a metal film having no liquid permeability. In addition, a thickness of a substrate, a method of coating or impregnating a substrate with the polymer (1), and the like are as described above. Since the thus prepared alcohol-based bactericidal material contains the sheet-like non-aqueous absorbent (B) of the present invention, and effectively absorbs an alcohol solvent, the material is suitably used as a sheet-type alcohol-based bactericidal material.

Another aspect is an integrated gelated-type alcohol-based bactericidal material comprising the aforementioned non-aqueous absorbent (B) and an alcohol solvent.

As a method of preparing the integrated gelated-type alcohol-based bactericidal material, for example, (v) a method of adding a predetermined amount of an alcohol solvent to the aforementioned particulate non-aqueous absorbent (B); (vi) a method of adding an alcohol solvent to a sheet containing the non-aqueous absorbent (B) may be used, and these alcohol-containing gels are preferably such that an integrated gel is prepared by the methods exemplified in (vii) and (viii).

A ratio of the non-aqueous absorbent (B)/alcohol solvent in this integrated gelated-type alcohol-based bactericidal material is preferably 0.1 to 99/1 to 99.9% by weight, more preferably 0.5 to 50/50 to 99.5% by weight, more preferably 1 to 30/70 to 99% by weight, most preferably 1 to 20/80 to 99% by weight. When a ratio of the non-aqueous absorbent (B) is 0.1% by weight or larger, a gel strength of the produced alcohol-containing gel is not weak, and a whole can not be gelated in any cases. On the other hand, the content is 99% by weight or smaller, the gel can be sufficiently used as an integrated gelated-type alcohol-based bactericidal material.

A form of the integrated gel comprising the non-aqueous absorbent (B) of the present invention and an alcohol solvent can be appropriately selected depending on a purpose and a utility, and examples of a shape include sheet-like, block-like, spherical, and cylindrical shapes. Among them, a preferable shape is sheet-like or block-like shape. When used as an alcohol-based bactericidal material for storing foods, a sheet-like shape is preferable. When formulated into a sheet-like gel, a thickness of gel is a preferably 1 to 10,000 μm, more preferably 10 to 1,000 μm. A width and a length of a sheet-gel may be appropriately selected depending on a use purpose, a use place, a utility and the like.

A method of preparing a gel having these shapes is not particularly limited, but examples include a method of performing gelating in a container or a cell in conformity with a shape which is wanted to be prepared, and a method of preparing a sheet-like gel by laminating or coating a mixture of the polymer (1), the monomer or the like and an alcohol solvent on a releasing paper, a film, a non-woven fabric or the like.

In addition, in order to contact feeling, if necessary, a water-soluble polymer such as polyvinyl alcohol, sodium polyacrylate, polyacrylamide and the like, a water-absorbing polymer such as crosslinked-polyacrylate salt, starch acrylate graft and the like, and a natural thickener such as pullulan, carrageenan and the like may be added to an alcohol-based bactericidal material.

In addition, another invention is an alcohol-based bactericide in which the alcohol-based bactericidal material is accommodated in an external material, at least a part of which is composed of a substrate through which a steam of an alcohol solvent, preferably, a steam of ethanol can permeate (hereinafter, referred to as steam permeable substrate).

Herein, the aforementioned alcohol solvent steam permeable substrate is a substrate having an alcohol solvent steam permeability, preferably, an ethanol steam permeability of 0.1 g/m$^2$·24 hr (50% RH/40° C.) or larger, more preferably 1 g/m$^2$·24 hr (50% RH/40° C.) or larger, further preferably 5 g/m$^2$·24 hr (50% RH/40° C.) or larger. Herein, an alcohol solvent steam permeability is expressed by an amount (g) of an alcohol solvent steam which passes through 1 m$^2$ of a substrate under environment of a temperature of 40° C. and a relative humidity of 50% for 24 hours, and a value thereof is measured according to JIS-Z-0208 generally used for measuring a water steam permeation amount of a resin film. As a material used as such the substrate, a sheet having pores or voids such as a paper, a non-woven fabric, a perforated plastic film, a microporous membrane and the like, a poreless film such as polyethylene, polypropylene, ethylene-vinyl acetate copolymer (EVA), ethylene-vinyl alcohol copolymer (EVAL), polyvinyl alcohol, ionomer, nylon, cellulose triacetate and the like, or a laminate thereof are used. Any materials may be used as long as contents thereof are riot leaked. If necessary, substrates may be subjected to water resistance treatment, oil resistance treatment, or printing.

Alternatively, a part of a substrate may be alcohol solvent steam impermeable. In this case, any sheets may be used as long as contents thereof are not leaked, and a material there of is not particularly limited.

In this alcohol-based bactericide, materials other than the non-aqueous absorbent (B) and the alcohol solvent may be present in the external material. Examples include a resin which absorbs the alcohol solvent, an ethanol carrier such as silicon dioxide, vermiculite and the like, an oxygen scavenger comprising an iron powder and an oxidation promoter such as sodium chloride, an aldehyde absorber such as polyallylamine and anionic exchange resin, ethylene adsorbent, ethylene generator, perfume and the like, other than the aforementioned non-aqueous absorbent (B), being not limiting. A method of allowing the aforementioned oxygen scavenger, aldehyde adsorbent, ethylene adsorbent, ethylene generator, perfume and the like to be present together is not particularly limited as long as sterilizing disinfecting effect of an alcohol-based bactericidal material and effects of other materials present therein are not prevented. For example, these materials may be mixed with an alcohol-based bactericidal material composition in advance, and accommodated into the external material to prepare a laminate sheet having a structure of (external material/the aforementioned non-aqueous absorbent (B)+coexisting substance/external material). Alternatively, these coexisting materials may be accommodated in a layer different from a layer in which the non-aqueous absorbent (B) is accommodated. In this case, by allowing to a sheet to intervene between the non-aqueous absorbent (B) layer and a coexisting material layer, a laminate sheet having a structure of (external material/the aforementioned non-aqueous absorbent (B) layer/intervening sheet/coexisting material layer/external material) may be prepared.

Since the non-aqueous absorbent (B) in the alcohol-based bactericide of the present invention can gelate a large amount of an alcohol solvent at a small amount, it becomes possible to hold a large amount of an alcohol solvent, and disinfecting or sterilizing effect lasts for a long period of time. Therefore, this can be suitably used as an alcohol-based bactericide such as a sheet-type alcohol-based bactericide, an integrated gelated-type alcohol-based bactericide and the like.

In addition, an alcohol-based bactericide in which the alcohol-based bactericidal material is accommodated in an external material, at least a part of which comprises a substitute through which a steam of an alcohol solvent can permeate, has no fear of pollution due to leakage of the contents. Alternatively, by accommodation in an external material having an regulated steam permeation amount, since disinfecting or sterilizing effect lasts for a longer time, the bactericide is used for treating foods by accommodating this and foods in a container having alcohol solvent steam retainability. Inter alia, the bactericide can be particularly suitably used for retaining freshness of breads, confectionary, processed foods, dry foods, cereals and the like.

[Cold Insulating Materials and Cold Insulators]

The cold insulating material of the present invention comprises the non-aqueous absorbent (B) and an alcohol solvent, and an alcohol solvent to be used may be the same as that used in the aforementioned alcohol-based bactericidal material.

An amount of absorbing an alcohol of the cold insulating material has no problem when the amount is designed as in the aforementioned alcohol-bactericidal material. When a sheet of the cold insulating material is sheet-like, a shape may be sheet-like as in the case of the alcohol-based bactericidal material. A substrate such as a non-woven fabric, a woven fabric, a paper, a film and the like which are, if necessary, used in order to render a form sheet-like may be the known substrate. Examples include a non-woven fabric or a woven fabric comprising a synthetic fiber and/or a natural fiber having a basis weight of around 10 to 500 g, a paper (wood free paper, thin paper, Japanese paper etc.), a film comprising a synthetic resin, a substrate of two or more of them, and a composite thereof. Among these substrates, preferable are a non-woven fabric, and a composite of a non-woven fabric and a film, and particularly preferable is a composite having one surface composed of a non-woven fabric and one surface composed of a film having no liquid permeability. A thickness, a length and a width of a sheet are as described for the aforementioned alcohol-based bactericidal material. A thickness of a substrate, and a method of coating or impregnating a substrate with a polymer (1) may be the same as those of the aforementioned alcohol-based bactericidal material. The thus prepared cold insulating material has a sheet-like form containing the non-aqueous absorbent (B) of the present invention, and effectively absorbs an alcohol solvent. Therefore, since the material retains softness even at freezing, and has cold insulating effect sustained for a long time, the material can be suitably used as a cold insulator.

Another aspect is an integrated gelated-type cold insulating material comprising the aforementioned non-aqueous absorbent (B) and an alcohol solvent. A ratio of the non-aqueous absorbent (B)/alcohol solvent in this integrated gelated-type cold insulating material, and a method of preparing the material may be the same as those of the aforementioned integrated gelated-type alcohol-based bactericidal material.

Thereupon, a form of a gel comprising the non-aqueous absorbent (B) and an alcohol solvent, and a method for preparing the gel may be the same as those of the aforementioned alcohol-based bactericidal material. In order to improve contact feeling, the same materials as those of the aforementioned alcohol-based bactericidal material may be added to the cold insulating material. By further adding a freezing-point depressant to an alcohol solvent, a freezing point may be further lowered, and it becomes possible to maintain softness at a lower temperature. Examples of such the freezing-point depressant include organic materials such as polyhydric alcohol (sorbitol etc.), urea and the like, and inorganic salts such as sodium chloride, lithium chloride, magnesium chloride, ammonium nitrate and the like. The freezing-point depressant is not particularly limited as long as it is a material which has a freezing-point lowering ability, and is dissolved in an alcohol solvent Preferable are inorganic salts. An amount of a freezing-point depressant to be added to an alcohol solvent is not particularly limited as long as the depressant is dissolved in an alcohol solvent, and freezing point lowering ability is exerted. Alternatively, in order to further increase cooling feeling, menthol may be incorporated. In addition, in order to prevent erroneous drinking, as a bitter ingredient, urea, phenylurea, caffein, naringin, nicotine, tenulin, lactucin, marrubiin, amarogentin, swelcide, aucubin, loganin, colchline, casterin, jasminine, denatonium benzoate and the like may be incorporated.

In addition, another invention is a cold insulator in which the aforementioned cold insulating material is accommodated in an external material comprising a substrate not allowing a steam of an alcohol solvent, preferably, a steam of ethanol to permeate (hereinafter, steam impermeable substrate), in order to suppress evaporation of an alcohol.

Herein, an alcohol solvent steam impermeable substrate is a substrate having an alcohol solvent steam permeability, for example, an ethanol steam permeability of preferably 10 $g/m^2 \cdot 24$ hr (50% RH/40° C.) or smaller, more preferably 1 $g/m^2 \cdot 24$ hr (50% RH/40° C.) or smaller, further preferably 0.1 $g/m^2 \cdot 24$ hr (50% RH/40° C.) or smaller. Herein, an alcohol solvent steam permeability is expressed by an amount (g) of an alcohol solvent steam passing through 1 $m^2$ of a substrate under environment of a temperature of 40° C. and a relative humidity of 50% for 24 hours, and a value thereof is measured according to JIS-Z-0208 generally used for measuring a steam permeation amount of a resin film. Examples of a material used as such the substrate include a plastic film such as low density polyethylene, biaxial-stretched polypropylene, polyester, nylon, polyvinyl chloride, polyvinylidene chloride and the like, and a laminate thereof, a metal film such as an aluminum foil, an aluminum-deposited film and the like, and the laminate thereof, a laminate of the plastic film and the metal film, and a laminate of those materials and a paper, a non-woven fabric, a woven-fabric and the like. A substrate which has alcohol steam impermeability and in which contents thereof are not leaked therefrom, is preferable, being not limiting.

In the cold insulator of the present invention, materials other than the aforementioned non-aqueous absorbent (B) and the aforementioned alcohol solvent may be present together in the aforementioned external material. Such the material and laminated sheet are as described for the aforementioned alcohol-based bactericidal material.

[Gel Sheets for Cooling]

The gel sheet for cooling of the present invention is formed of a gel layer of the aforementioned cold insulating material and a support. The gel layer can be processed into various forms depending on a purpose, being not particularly limiting. Examples of a preferable form include particulate, sheet-like, and integrated gelated-type forms. More preferable is sheet-like. A method of preparing a sheet-like gel layer is as described for preparation of the sheet-like cold insulating material. A thickness and a length of a sheet, an additive, a kind and a thickness of a substrate, a coating method, absorbing ability and the like are preferably the same as those of the cooling insulating material.

Examples of a support is not particularly limited, but specifically, examples include a combination of one or more selected from the group consisting of a steam permeable substrate having an alcohol solvent steam permeability exceeding 0.1 $g/m^2 \cdot 24$ hr (50% RH·40° C.) as in the aforementioned alcohol-based bactericidal material, an external material and a pressure-sensitive adhesive layer.

A pressure-sensitive adhesive agent constituting the pressure-sensitive layer may be the known pressure-sensitive adhesive used in a cataplasm or the previous gel sheet for cooling, and examples include a pressure-sensitive adhesive such as thermally crosslinked CMC, gelatin, gum arabic and the like. Among them, preferable are thermally crosslinked CMC, gelatin and the like which have high safety even when contacted with a skin.

Among these supports, preferable is the aforementioned steam permeable substrate, and further preferable is a non-woven fabric.

In the gel sheet for cooling, a support is contacted with at least a part of a gel layer. An area with which a support is contacted is not particularly limited as long as a part of a gel layer is exposed, but preferably 75% or smaller, more preferably 65% or smaller, further preferably 50% or smaller of a surface area of a gel layer. Therefore, as a preferable aspect of a gel sheet for cooling, a gel layer is attached to one surface of the aforementioned steam permeable substrate. A pressure-sensitive adhesive may be directly contacted with a gel layer.

A size of a gel sheet for cooling of the present invention can be arbitrarily adjusted depending on a use purpose.

For example, when used on a forehead of a head, around 5 cm×10 cm is preferable. In the case of back of a foot, 5 to 6 cm×20 to 25 cm is preferable. A size of the sheet may be adjusted to these sizes at either of preparation or use.

In another preferable aspect, a gel layer is accommodated in an external material. That is, in order that an alcohol solvent is not evaporated until a gel sheet for cooling is used, it is preferable that a gel layer part is covered and sealed with a substrate having an alcohol solvent steam permeability of 0.1 g/m²·24 hr (50% RH/40° C.) or smaller, and a gel layer part is opened upon use to evaporate an alcohol solvent. Examples of this substrate having an alcohol solvent steam permeability of 0.1 g/m²·24 hr (50% RH/40° C.) or smaller include a paper having low steam permeability (e.g. oiled paper etc.), a non-woven fabric (e.g. resin-processed fabric), a plastic film (poreless film such as polyethylene, polypropylene, ethylene-vinyl acetate copolymer (EVA), ethylene-vinyl alcohol copolymer (EVAL), polyvinyl alcohol, ionomer, nylon, cellulose triacetate etc.) and the like.

Alternatively, in the aforementioned construction, a pressure-sensitive adhesive may be combined with an external material. An area on which a pressure-sensitive adhesive is attached to an external material is preferably 50% or smaller, more preferably 25% or smaller of a surface area of the aforementioned gel layer.

When a pressure-sensitive adhesive is used, the gel sheet for cooling can be easily fixed to a human body by adhering to a skin, and a gel layer having elasticity accommodated in an outer material exerts cooling effect as a cooling agent for a long time.

Since the non-aqueous absorbent (B) in a gel layer in the present invention can gelate a large amount of alcohol solvent at a small amount, it becomes possible to retain a large amount of an alcohol solvent, and softness is retained even at freezing, and cooling effect lasts over a long time. Therefore, this can be suitably used as a gel sheet for cooling.

In addition, when the gel sheet for cooling of the present invention is accommodated in an outer material, at least a part of which comprises a substrate through which an alcohol solvent steam can permeate, there is no fear of pollution due to leakage of the contents, and since cooling effect lasts over a longer time by accommodating in an outer material having a regulated steam permeation amount, this is suitable as a gel sheet for cooling.

That is, the gel sheet for cooling of the present invention absorbs heat from the surrounding due to evaporation latent heat due to volatilization of an alcohol solvent contained in gel layer from the surface of a gel layer, and has cooling effect even when a gel sheet for cooling is not especially cooled. By freezing with a freezer, it becomes possible to cool for a further long time.

[Fuel Compositions for Solid Fuels or Solid Fuels Using the Same]

The fuel composition for solid fuels of the present invention is a composition comprising the non-aqueous absorbent (B) and an alcohol solvent, and the solid fuel uses the same. As the alcohol solvent used in the fuel composition for solid fuels and the solid fuel of the present invention, an alcohol fuel is used.

Herein, the alcohol fuel refers to an alcohol alone which easily initiates combustion when ignited with a lighter, a match or the like, or a mixture of this and a combustible organic solvent which is miscible therewith. Preferable is an alcohol alone. A preferable alcohol includes methanol, ethanol, isopropyl alcohol, butanol and a mixture thereof, and a more preferable alcohol includes methanol, ethanol and a mixture thereof.

As used herein, a miscible combustible organic solvent refers to an organic solvent which can be mixed with the alcohol fuel at an arbitrary ratio, and in which a mixture with the alcohol fuel easily initiates combustion when ignited with a lighter, match or the like. The combustible organic solvent is not particularly limited as long as it is such the solvent, and preferable examples include ketones such as acetone, methyl ethyl ketone and the like, esters such as ethyl acetate, butyl acetate and the like, ethers such as diethyl ether, tetrahydrofuran and the like, and polyhydric alcohols such as ethylene glycol, propylene glycol and the like.

When the fuel composition for solid fuels is shaped into a sheet, the sheet may be the same as that of the aforementioned alcohol-based bactericidal material. A thickness, a length and a width of a sheet; a substrate to be used, and a basis weight may be the same as those of the aforementioned alcohol-based bactericidal material. A thickness of a base, and a method of coating or impregnating a substrate with the polymer (1) may be the same as those described above. Since the thus prepared fuel composition for solid fuels contains the sheet-like non-aqueous absorbent (B) of the present invention, and effectively absorbs an alcohol fuel, the composition is suitably used as a sheet-type fuel composition.

Another aspect is an integrated gelated-type fuel composition comprising the non-aqueous absorbent (B) and an alcohol fuel. A ratio of the non-aqueous absorbent (B)/alcohol fuel, and a process for preparing a composition in this integrated gelated-type fuel composition may be the same as those of the aforementioned integrated gelated-type alcohol-based bactericidal material.

In addition, an amount of absorbing an alcohol fuel in the fuel composition for solid fuels may be designed as in the case of the alcohol-based bactericidal material.

A form of a gel comprising the non-aqueous absorbent (B) and an alcohol solvent, and a method of preparing the same may be as in the alcohol-based bactericidal material. If necessary, one or more selected from the group consisting of other gelating agent (fatty acid soap, dibenzalsorbitol, hydroxypropylcellulose, benzylidenesorbitol, carboxyvinylpolymer, polyethylene glycol, polyoxyalkylene, sorbitol, nitrocellulose, methylcellulose, ethylcellulose, acetylbutylcellulose, polyethylene, polypropylene, polystyrene, ABS resin, AB resin, acrylic resin, acetal resin, polycarbonate, nylon, phenol resin, phenoxy resin, urea resin, alkyd resin, polyester, epoxy resin, diallyl phthalate resin, polyallomer etc.), a thickener, a binder, a carbonaceous solid fuel (charcoal, oval briquet, briquet, anthracite, sawdust charcoal, used charcoal, papers, hemp, cotton, hair, silk, paraffin etc.), an igniting agent, a conbustion accelerator (oxidizing agent such as permanganates, nitrates, perchlorates etc.), a combustion inhibitor (silicates such as silica gel etc.), clay such as bentonite, kaolinite, montmorillonite etc., potter's clays), a fire sparks flight preventing agent, a compound and/or a complex containing a metal exhibiting a flame reaction (strontium, lithium, calcium, sodium, barium, copper, potassium etc.), and a perfume (animal perfume such as musk, civet etc., plant perfume such as lemongrass oil, mentha oil etc., synthetic perfume such as limonene, isobutylaldehyde, menthol, eugenol, camphor, coumarin, benzyl acetate etc.) may be incorporated into the fuel composition for solid fuels of the present invention. These are not particularly limited as long as they can exert their function, whether solid or liquid. In addition, these may be incorporated at an arbitrary stage of preparation of the fuel composition for solid fuels.

A form of the fuel composition for solid fuels of the present invention is selected from the group consisting of solid-like, gel-like, pellet-like and sheet-like. The solid fuel of the present invention is characterized in that the aforementioned fuel composition for solid fuels is accommodated in an external material comprising a substrate through which a steam of an alcohol fuel, preferably, a steam of ethanol does not permeate (hereinafter, referred to as steam impermeable substrate), in order to suppress volatilization of a fuel. In this case, an alcohol solvent (alcohol fuel) steam permeability of the steam impermeable substrate is as in the case of the aforementioned alcohol-based bactericidal material.

In an external material for the solid fuel, for example, a resin of absorbing the alcohol fuel, an ethanol carrier such as silicon dioxide, vermiculite etc., an igniting agent, a combustion accelerator, a combustion inhibitor, a fire sparks flight preventing agent, a compound and/or a complex containing a metal exhibiting a flame reaction, a perfume, a antiseptic, a mildewproofing agent, an antioxidant, an ultraviolet absorbing agent and the like may coexist, in addition to the non-aqueous absorbent (B), being not limiting. A laminate sheet may be as in the alcohol-based bactericidal material.

Since the non-aqueous absorbent (B) which is a constituent of the fuel composition for solid fuels of the present invention can gelate a large amount of alcohol fuel at a small amount, it becomes possible to retain a large amount of alcohol fuel, and combustion lasts over a long time, the non-aqueous absorbent of the present invention can be suitably used as a solid fuel.

In addition, since the solid fuel in which the fuel composition for solid fuels is accommodated in an external material comprising a substrate through which a steam of an alcohol fuel does not permeate, has no fear of pollution due to leakage of contents, and the decrease of an amount of holding an alcohol fuel due to volatilization after long term storage is not occurred, handling and storage become easy, and combustion lasts for a long time at combustion and, thus, such the solid fuel is suitable as a solid fuel.

[Fragrance Materials or Fragrances]

The fragrance material of the present invention comprises a non-aqueous absorbent (B) of the present invention and an aromatic drug and it is preferable that the aromatic drug has normal temperature volatility.

Herein, the aromatic drug having normal temperature volatility is not particularly limited as long as it has aroma, and is volatilized or evaporated at a normal temperature (normal life temperature, herein, 5 to 40° C.), and may be liquid or solid. When the drug is liquid, it can be used as it is. When the drug is a liquid having a high viscosity and is hardly absorbable, or a solid, the drug can be dissolved in an alcohol solvent (ethanol etc.), and then, absorbed in the non-aqueous absorbent (B) constituting a fragrance material. The concentration at dissolution may be adjusted depending on a use purpose, being not particularly limited. When the drug is a thermally meltable solid, it is absorbed in the non-aqueous absorbent (B) constituting a fragrance material, after thermal melting. Specifically, there are natural perfumes and synthetic perfumes.

Examples of the natural perfume include animal perfumes such as musk, civet, ambergris and the like, natural plant oils such as abies oil, almond oil, bazin, birch oil, cajabute oil, cardamon oil, celery oil, cinnamon oil, citronella oil, cognac oil, cumin oil, camphol oil, estogoran oil, eucalyptus oil, garlic oil, ginger oil, grapefruit oil, hop oil, lemon oil, timewhite oil, lemongrass oil, cassia oil, viment oil, cypress oil, white-sedar leaf oil, floral oil, nutmeg oil, mandarin oil, pepper oil, oragne oil, turpentine oil and the like, and citral, cinnamic aldehyde, thymol, eugenol, rosemary, sage and the like as a natural plant oil extract. Examples of the synthetic perfume include hydrocarbons such as pinene, limonene and the like, alcohols such as geraniol, citroneol, menthol, borneol, benzyl alcohol and the like, phenols such as eugenol and the like, aldehydes such as isobutylaldehyde, cetral, citronellal, cinnamicaldehyde and the like, ketones such as acetophenone and the like, lactones such as coumarin and the like, and esters such as benzyl acetate, cinnamyl acetate, isopropyl isobutyrate, benzyl benzoate, cinnamyl cinnamate and the like.

These may be used alone, or may be a perfume obtained by compounding two or more kinds.

An amount of absorbing an aromatic drug of the non-aqueous absorbent (B) constituting the fragrance material may be designed as in an alcohol absorbing amount in the case of the alcohol-based bactericidal material.

When the fragrance material is shaped into a sheet, the sheet may be as in the case of the aforementioned alcohol-based bactericidal material. A thickness, a length and a width of a sheet; a substrate used, a thickness of a substrate, a method of coating or impregnating a substrate with the non-aqueous absorbent (B), and a basis weight may be the same as those of the alcohol-based bactericidal material. Since the thus prepared fragrance material contains the sheet-like non-aqueous absorbent (B) of the present invention, and effectively absorbs an aromatic drug, the material is useful as a sheet-type fragrance.

Another aspect is an integrated gelated-type fragrance material comprising the (B) and an alcohol solvent. A ratio of the (B)/aromatic drug, and a method of preparing a material in this integrated gelated-type fragrance material may be as in the aforementioned alcohol-based bactericidal material.

A form of a gel of the integrated gelated-type fragrance material comprising (B) and an aromatic drug, and a method for preparing the same may be as in the alcohol-based bactericidal material. In order to improve contact feeling, the same materials as those for the aforementioned alcohol-based bactericidal material may be added to the integrated gelated-type fragrance material.

In addition, the fragrance of the present invention is characterized in that the fragrance material is accommodated in an external material, at least a part of which comprises a substrate through which a steam of a normal temperature volatile component present in the aromatic drug can permeate. In this case, a normal temperature volatile component steam permeability of a substrate, and a kind of substrate may be as in the alcohol-based bactericidal material.

Materials to be present together in the fragrance material or the external material of the fragrance, and the laminated sheet may be as in the alcohol-based bactericidal material.

In addition, in order to prevent erroneous drinking, urea, phenylurea, caffein, naringin, nicotine, tenulin, lactucin, marrubin, amarogentin, swelcide, aucubin, loganin, colchlone, casterin, jasmine, denatonium benzoate and the like as a bitter ingredients may be incorporated in the fragrance of the present invention.

[Patch Materials and Patches]

The patch material of the present invention comprises the non-aqueous absorbent (B) and a percutaneous absorption drug.

In the present invention, the percutaneous absorption drug is not particularly limited as long as it has percutaneous absorbability, and may be liquid or solid. When the drug is liquid, it can be used as it is. When the drug is a liquid having a high viscosity and is hardly absorbable, or a solid, the drug may be dissolved in water or an alcohol solvent (ethanol etc.), and absorbed in the non-aqueous absorbent (B) constituting the patch material. The concentration of the percutaneous absorption drug at dissolution may be adjusted depending on a use purpose, being not particularly limited. When the percutaneous absorption drug is a solid having thermal meltability, it is absorbed in the non-aqueous absorbent (B) constituting the patch material, after thermal melting.

In the present invention, specifically, examples of the percutaneous drug include anti-inflammatory agents such as methyl salicylate, glycol salicylate, diphenylhydrazines, indometacin, flurbiprofen and ketoneprofen, skin stimulating agents such as camphor, menthol and the like, central nerve acting agents (sleep-analgesic, anti-epilepsy agent, psychoneurotic agent), diuretic, hypotensive agent, coronary vasodilator, antitussive expectorant, anti-histamine agent, arrhythmia agent, cardiotonic drug, adrenocortical hormone, anesthetic and the like. These may be used alone, or by mixing two or more.

An amount of absorbing the perucutaneous absorption drug of the patch material may be designed as in an amount of absorbing an alcohol in the case of the aforementioned alcohol-based bactericidal material.

When the patch material is shaped into a sheet, the sheet may be as in the alcohol-based bactericidal material. A thickness, a length and a width of a sheet; a substrate to be used, a thickness of a substrate, a method of coating or impregnating a substrate with the non-aqueous absorbent (B), and a basis weight may be as described above. Since the thus prepared patch material contains the sheet-like non-aqueous absorbent (B) of the present invention, and effectively absorbs the perucutanous absorption drug, the material is useful as a sheet-type patch material.

Another aspect is an integrated gelated-type patch material comprising the (B) and a percutaneous absorption drug. A ratio of the (B)/percutaneous absorption drug, and a method of preparing the same in this integrated gelated-type patch material may be as in the integrated gelated-type alcohol-based bactericidal material.

A form of the integrated gelated-type patch material comprising (B) and a percutaneous absorption drug, a method of preparing the same may be as in the alcohol-based bactericidal material.

The patch of the present invention comprises the aforementioned patch material. That is, the patch of the present invention allows the aforementioned patch material to be used. For example, when the patch material is used, it is preferable to combine one or more substrates selected from the group consisting of a non-woven fabric, a woven fabric, a paper, a plastic film and a metal film. Alternatively, in order to improve adherability with a skin, a pressure-sensitive adhesive may be used in the patch of the present invention. The pressure-sensitive adhesive may be the known pressure-sensitive adhesive which is used in the previous patch, and examples include pressure-sensitive adhesives such as sodium polyacrylate, glycerin, sorbitol, gum arabic and the like. Among them, preferable are sodium polyacrylate and sorbitol which have high safety even when contacted with a skin.

In the patch having the aforementioned construction, it is preferable that a substrate (support) is contacted with at least a part of an integrated gelated-type patch material (gel layer). An area with which a support is contacted is not particularly limited as long as a part of a gel layer is exposed, and is preferably 75% or smaller, more preferably 65% or smaller, further preferably 50% or smaller of a surface area of a gel layer. Therefore, a preferable aspect of the patch of the present invention is such that a gel layer is attached to one surface of the support. Alternatively, a pressure-sensitive adhesive may be directly contacted with a gel layer.

Materials other than the non-aqueous absorbent (B) may coexist in a gel layer in the present invention. Examples of the materials include a resin which absorbs the percutaneous absorption drug, an ingredient having warm-feeling, a representative of which is capsaicin derived from *Capsicum annuum* L. for imparting warm-feeling effect and an analog thereof, an antiseptic, a fungicide, an antioxidant, a ultraviolet absorbing agent, a perfume and the like in addition to the (B), being not limiting. A method of allowing the aforementioned antiseptic, fungicide, antioxidant, ultraviolet absorbing agent, perfume and the like to coexist is not particularly limited as long as percutaneous absorption effect of the patch of the present invention and effects of other coexisting materials are not prevented. For example, these materials may be mixed with a gel layer in advance, and coated on the support. Alternatively, these coexisting materials may be accommodated in a layer different from a gel layer. In order to improve contact feeling, the same polymer and thickener as those described for the alcohol-based bactericidal material may be added to the patch of the present invention.

Since the patch of the present invention contains the non-aqueous absorbent (B) of the present invention, and can gelate a large amount of percutaneous absorption drug even at a small amount, it becomes possible to retain a large amount of percutaneous absorption drug and, since anti-inflammatory effect lasts over a long time, the patch of the present invention can be suitably used as a patch.

[Insecticidal Compositions and Insecticides]

The insecticidal composition of the present invention comprises the non-aqueous absorbent (B) of the present invention and a pyrethroid insecticidal ingredient.

The pyrethroid insecticidal ingredient is not particularly limited as long as it is liquid or solid. When the ingredient is liquid, it can be used as it is. When the ingredient is a liquid having a high viscosity and is hardly absorbable, or a solid, it may be dissolved in an alcohol solvent (ethanol etc.), and absorbed in the non-aqueous absorbent (B). The concentration at dissolution may be adjusted depending on a use purpose, being not particularly limited. When the pyrethroid insecticidal ingredient is a solid having thermal meltability, it may be absorbed in (B) after thermal melting.

In the present invention, specifically, examples of the pyrethroid insecticidal ingredient include empenthrin, flamethrin, transfurthrin, teflamethrin, allethrin and prarethrin, and the ingredient may be appropriately selected depending on a utility and a purpose. Among them, preferable are empenthrin, flamethrin, transfurthrin and prarethrin, and more preferable are empenthrin, transfurthrin and allethrin.

An amount of absorbing the pyrethroid insecticidal ingredient (hereinafter, insecticidal ingredient) of the insecticidal composition of the present invention may be designed as in an amount of absorbing an alcohol in the case of alcohol-based bactericidal material, being not problematic.

When the insecticidal composition is shaped into a sheet, the sheet may be as in the alcohol-based bactericidal material. In addition, a thickness, a length and a width of a sheet; a substrate to be used, a thickness of a substrate, a method of coating or impregnating a substrate with the non-aqueous absorbent (B), and a basis weight may be as described above. Since the thus prepared insecticidal composition contains the sheet-like non-aqueous absorbent (B) of the present invention, and effectively absorbs the insecticidal ingredient, it is used as a sheet-type insecticide.

Another aspect is an integrated gelated-type insecticide comprising the (B) and an insecticidal ingredient. A ratio of the (B)/insecticidal ingredient, a method of preparing the same in this integrated gelated-type insecticide may be as in the alcohol-based bactericidal material.

A form of a gel comprising (B) and the insecticidal ingredient, and a method of preparing the same may be as in the alcohol-based bactericidal material.

In addition, in view of long term use, it is preferable to incorporate a stabilizer into the insecticidal composition of the present invention. Further, if necessary, a volatilization adjusting agent, a solvent, a perfume, a pigment and the like may be appropriately added. As the stabilizer, stabilizers which are not substantially volatilized at a heating temperature of 50 to 200° C., such as dibutylhydroquinone, 2,2'-methylenebis-(4-ethyl-6-t-butylphenol), 4,4'-butylidenebis-(3-methyl-6-t-butylphenol), tris(2-methyl-4-hydroxy-5-t-butylphenyl)butane, pentaerythrityl-tetrakis[3-(3,5-di-t-butyl-4-hydroxyphenyl)propionate], stearyl-β-(3,5-di-t-butyl-4-hydroxyphenyl)propionate, tris-(3,5-di-t-butyl-4-hydroxybenzyl)isocyanurate, 4,4'-thiobis-(3-methyl-6-t-butylphenol), 2-mercaptobenzimidazole, trinonylphenyl phosphite and the like are preferable, and these may be used alone, or in combination of two or more.

The insecticide of the present invention is characterized in that the aforementioned insecticidal composition is accommodated in an external material, at least a part of which comprises a substrate through which a steam of an insecticidal ingredient can permeate (hereinafter, referred to as steam permeable substrate).

Herein, an insecticidal ingredient steam permeable substrate is a substrate having an insecticidal ingredient steam permeability of preferably 0.1 g/m$^2$·24 hr (50% RH/40° C.) or larger, more preferably 1 g/m$^2$·24 hr (50% RH/40° C.) or larger, further preferably 5 g/m$^2$·24 hr (50% RH/40° C.) or larger. Herein, a steam permeability, definition, and a measuring method of the insecticidal ingredient, and a kind of a material may be the same as those of the aforementioned alcohol-based bactericidal material.

In the aforementioned construction, a part of the substrate may be insecticidal ingredient steam permeable. In this case, a substrate may be such a sheet that contents are not leaked, and a material of the substrate is not particularly limited.

In the insecticide of the present invention, materials other than the (B) and the insecticidal ingredient may coexist in the external material. Examples of the materials include a resin which absorbs an insecticidal ingredient, an insecticidal ingredient carrier such as silicon oxide, vermeculite and the like, an oxygen scavenger comprising an iron powder and an oxidation promoter such as sodium chloride, an aldehyde adsorbent such as polyallylamine and anionic exchange resin, an ethylene absorbent, an ethylene generator, a perfume and the like, other than (B), being not limiting. A method of allowing the aforementioned oxygen scavenger, aldehyde adsorbent, ethylene adsorbent, ethylene generator, perfume and the like to coexist is not particularly limited as long as the insecticidal effect of the insecticide of the present invention and effects of other coexisting materials are not prevented, and is as described for the alcohol-based bactericidal material.

A mode for carrying out the insecticidal composition and the insecticide of the present invention is not particularly limited, but the insecticidal composition and/or the insecticide of the present invention may be used per se as a normal temperature volatilization type, or may be formulated into a heating volatilization type and may be used by heating. A normal temperature volatilization insecticidal composition or insecticide which can be used at a normal temperature may be filled, for example, in a plastic container, and may be used by hanging in a wardrobe, or a sheet-type insecticide may be wrapped with a Japanese paper, and may be used by placing into a drawer.

In addition, when a heating volatilizing type is used by heating, for example, this is filled into a plastic container, this is placed on a radiating plate which Ls heated at a temperature of 50 to 200° C., and is used by gradual volatilization of an insecticidal ingredient, thereby, insecticidal efficacy can be maintained for a long term. A temperature of a radiating plate is preferably 50 to 200° C., more preferably 60 to 190° C., further preferably 70 to 180° C. When the temperature is 50° C. or higher, an insecticidal ingredient in a heating volatilization type is volatilized at a necessary amount. When the temperature is 200° C. or lower, a gel is not deteriorated by heat.

Since the insecticidal composition of the present invention contains the aforementioned non-aqueous absorbent (B) as a constitutional component, and can gelate a large amount of insecticidal ingredient even at a small amount, it becomes possible to retain a large amount of an insecticidal ingredient and, since insecticidal effect lasts over a long term without fear of liquid leakage unlike the previous liquid insecticide, the composition can be suitably used as a normal temperature volatilization type or heating volatilization insecticidal composition.

In addition, since an insect-killing method of filling an insecticide obtained by accommodating the insecticidal composition of the present invention in an external material, at least a part of which comprises a substrate through which a steam of an insecticidal ingredient can permeate, into a plastic container, and hanging this in a wardrobe, and an insect-killing method of placing the container on a radiating plate which is heated at a temperature of 50 to 200° C. have no fear of pollution due to leakage of contents, and insecticidal effect lasts over a further long term by accommodating in an external material having a regulated steam permeation amount, those methods become an extremely useful heating volatilization insect-killing method.

[Fuel Stores for Fuel Batteries and Fuel Batteries]

The fuel store for fuel batteries (hereinafter, referred to as fuel store) in the present invention comprises the non-aqueous absorbent (B) and a liquid fuel for fuel batteries, and the fuel battery uses the same.

The liquid fuel for fuel batteries (hereinafter, referred to as liquid fuel) used in the present invention is not particularly limited as long as it is a fuel for fuel batteries which has previously been used. Preferably, the liquid fuel is a mixture of one or more selected from the group consisting of methanol, ethanol, hydrazine, formalin, liquified petroleum gas, naphtha, gasoline, kerosine, liquified natural gas, and liquified dimethyl ether, or a mixture of this and water. More preferable are methanol, ethanol and a mixture of water and them.

An amount of absorbing a liquid fuel of the fuel store of the present invention may be designed as in an amount of absorbing an alcohol in the case of the alcohol-based bactericidal material.

When the fuel store of the present invention is shaped into a sheet, the sheet may be as in the aforementioned sheet-like alcohol-based bactericidal material. A thickness, a length and a width of a sheet; a substrate to be used, a thickness of a substrate, a method of coating or impregnating a substrate with the non-aqueous absorbent (B), and a basis weight may be as described above. Since the thus prepared liquid fuel store for fuel batteries contains the sheet-like non-aqueous absorbent (B) of the present invention, and effectively absorbs the liquid fuel for fuel batteries, this can be used as a sheet-like fuel store for fuel batteries.

Another aspect is an integrated gelated-type fuel store comprising the (B) and a liquid fuel. A ratio of the (B)/liquid fuel, and a method of preparing the same in this integrated gelated-type fuel-stored may be as in the alcohol-based bactericidal material.

In addition, if necessary, one or more selected from the group consisting of other gelating agent (examples include the same gelating agents as those described-above for the fuel composition for solid fuels), an adsorbent (dextrin, dextran, silica gel, silica, alumina, molecular sieve, kaolin, diatomaceous earth, carbon black, active carbon etc.), a thickener, a binder, and a material which chemical converts a liquid fuel into a non-flowing fuel may be incorporated in the fuel store of the present invention. These are not particularly limited as long as they exert their function, and may be solid or liquid. In addition, they may be incorporated at any stage of preparation of the fuel store.

In order to suppress volatilization of a fuel, another aspect is a fuel store characterized in that the aforementioned fuel store is accommodated in an external material comprising a substrate through which a steam of a liquid fuel, preferably, a steam of methanol does not permeate, and a fuel supply valve is attached to a part of thereof.

In the present invention, the aforementioned substrate through which a steam of a liquid fuel does not permeate is a substrate having a liquid fuel steam permeability, preferably, a methanol steam permeability of preferably $10 \text{ g/m}^2 \cdot 24 \text{ hr}$ (50% RH/40° C.) or smaller, more preferably $1 \text{ g/m}^2 \cdot 24 \text{ hr}$ (50% RH·40° C.) or smaller, further preferably $0.1 \text{ g/m}^2 \cdot 24 \text{ hr}$ (50% RH; 40° C.). Definition and a measuring method of a liquid fuel steam permeability are as in the case of the alcohol-based bactericidal material.

Examples of the material used in the aforementioned substrate include materials described for the cool insulating material, a metal can such as an aluminum can and a laminate thereof, a laminate of the aforementioned plastic film, the aforementioned metal film and the aforementioned metal can, and a laminate of them and a paper, a non-woven fabric, a woven fabric or the like. Such the substrate is not particularly limited as long as it is a substrate having liquid fuel steam impermeability and no leakage of contents.

Alternatively, if necessary, a substrate may be subjected to water resistance treatment, oil resistance treatment or printing.

In addition, when an external material is a monolayer, it is not particularly limited as long as a liquid fuel steam permeability is in the aforementioned range. In addition, even when an external material is a laminate, the number of layers is not particularly limited as long as a liquid fuel steam permeation is in the aforementioned range Preferably, the number of layers is 2 to 5. More preferably, the number of layers is 2 to 3. Alternatively, different kinds of materials may be combined.

Materials which are allowed to coexist in an external material for the fuel store, and the laminated sheet may be as in the alcohol-bactericidal material.

Examples of a method of releasing a liquid fuel from the fuel store of the present invention include the following methods (i) to (iv). As long as a necessary amount of a fuel is released at a necessary time, the method is not limited to them. Alternatively, two or more of these methods may be combined.

(i) A method of heating a fuel tank to release a fuel from a fuel store, and supplying the fuel to a fuel electrode.

(ii) A method of compressing a fuel tank to release a fuel from a fuel store, and supplying the fuel to a fuel electrode.

(iii) A method of heating a fuel store which is mounted in place of a fuel tank, to release a fuel, and supplying the fuel to a fuel electrode.

(iv) A method of compressing a fuel store which is mounted in place of a fuel tank, to release a fuel store, and supplying a fuel to the fuel electrode.

Another invention is a fuel battery comprising the non-aqueous absorbent (B) and a liquid fuel for fuel batteries. In particular, the fuel battery of the present invention is suitable in a methanol-type fuel battery.

Usually, a methanol-type fuel battery is composed of a fuel electrode, an air electrode, an electrolyte layer, a fuel tank, an air tank, a fuel supplying port, an air supplying port, an outlet for discharging a reaction product gas, an outlet for discharging a reaction product substance and the like. As a liquid fuel, an aqueous methanol solution is mainly used, and a liquid fuel is sent from a fuel tank to a fuel electrode. In the present invention, it is preferable that a fuel battery is formed by the method of (v) or (vi).

(v) A method of using the non-aqueous absorbent (B) and/or a fuel store in a line from a fuel tank to a site contacting directly with a fuel electrode and/or contacting indirectly with a fuel electrode via a volatilizing layer.

(vi) A method of using the non-aqueous absorbent (B) in an electrolyte layer.

In the case of (v), the non-aqueous absorbent (B) is present in a fuel supplying line from a fuel tank to a fuel electrode, and an aqueous methanol solution is filled therein. When the non-aqueous absorbent (B) is directly contacted with a fuel electrode, a fuel oozes out gradually from a contact surface and is supplied to a fuel electrode, and is used in a reaction. When the non-aqueous absorbent (B) is indirectly contacted with a fuel electrode via a volatilizing layer, a liquid fuel is supplied from the non-aqueous absorbent (B) and/or a fuel store to the volatilizing layer, volatilized in the volatilizing layer, and a gaseous fuel is supplied to a fuel electrode and is used in a reaction. Since occurrence of bubbles during a long unused term or occurrence of bubbles due to exothermic heat during battery working can be prevented by gelating a fuel in a fuel supplying line using the non-aqueous absorbent (B), it becomes possible to retain an amount of supplying a fuel to a fuel electrode constant. Thereupon, a shape of the non-aqueous absorbent (B) is not particularly limited as long as a liquid fuel can be absorbed and gelated, but preferably is particulate or sheet-like.

In the method of (vi), crossover of methanol which is one of most important problems to a methanol battery can be prevented. That is, since a fuel which has became excessive at a fuel electrode is permeated to an air electrode via an electrolyte layer, a fuel is directly oxidized on an air electrode, and the deterioration of the performance of an air electrode can be considerably suppressed. In this case, the non-aqueous absorbent (B) may be located at any position of a fuel battery as long as a fuel permeating through an electrolyte layer can be absorbed, but preferably located between a fuel electrode and an air electrode and/or at a contact surface between a fuel electrode and an electrolyte layer. A shape of the non-aqueous absorbent (B) is not particularly limited, but any shape may be used as long as a fuel permeating through an electrolyte layer can be absorbed. Preferable is sheet-like.

In the fuel battery of the present invention, other materials, for example, a fuel permeating plate (carbon porous plate etc.) may coexist in order to permeate a fuel, or the previous ion exchange membrane (copolymer of tetrafluoroethylene and perfluorovinyl ether etc.) may coexist in order to arrest crossover of a fuel. A method of allowing those materials to coexist is arbitrary as long as their function is not prevented.

Since the sheet-type fuel store, the integrated gelated-type fuel store, and the fuel store obtained by accommodating in an external material comprising a substrate through which a steam of their liquid fuel does not permeate, of the present invention, contains the non-aqueous absorbent (B) of the present invention, and can gelate a large amount of liquid fuel for fuel batteries even at a small amount, it becomes possible to retain a large amount of a liquid fuel for fuel batteries and, since a discharging time lasts for a long time, this can be suitably used as a fuel store.

In addition, since in the fuel battery provided with the non-aqueous absorbent (B), when the non-aqueous absorbent (B) is used in a fuel supplying line, a problem of unstabilization of a fuel supplying amount due to occurrence of bubbles is solved and, when used in an electrolyte, crossover of a fuel does not occur, and reduction in properties of an air electrolyte can be suppressed, it becomes possible to make a fuel battery which is stable over a long term and, thus, this is particularly suitable in a methanol-type fuel battery.

The following Examples and Comparative Examples further illustrate the present invention, but the present invention is not limited by them.

Hereinafter, unless otherwise indicated, % indicates % by weight.

EXAMPLE 1

360 Grams (5 mole) of acrylic acid, 1.08 g of pentaerythritol triallyl ether and 1140 g of water were placed into a 2 liter thermal insulating polymerization tank.

A temperature of a monomer solution was cooled to 0° C., nitrogen was bubbled through the solution to reduce dissolved oxygen, and 0.36 g of 2,2'-azobis(2-amidinopropane) hydrochloride, 3.1 g of a 35% aqueous hydrogen peroxide and 0.38 g of L-ascorbic acid as a polymerization initiator were added to initiate polymerization.

After polymerization, the produced hydrous gel was subdivided using a meat chopper and, thereafter, to this gel was added 1353 g (4 mole) of a 60% methanol solution of methylcarbonate of 1,2,3,4-trimethylimidazolinium cation (molecular weight: 203) (manufactured by Sanyo Chemical Industries, Ltd.), and occurrence of decarbonization and demethanolation was observed.

A hot air at 100° C. was permeated through the gel with imidazolinium cation added thereto using a band-drier (permeating drier manufactured by Inoue Kinzoku), water used as a solvent and methanol produced as a side produce were distilled off, followed by drying.

The dry material was ground using a cutter mill to obtain a particulate non-aqueous absorbent (B1) comprising a crosslinked body (A1) in the present invention having an average particle diameter of 400 μm.

EXAMPLE 2

According to the same manner as that of Example 1 except that 3307 g (4.5 mole) of a 20% aqueous solution of triethylammonium hydroxide (molecular weight: 147) (manufactured by Sanyo Chemical Industries, Ltd.) was added in place of methylcarbonate of 1,2,3,4-trimethylimidazolinium cation used in Example 1, a non-aqueous absorbent (B2) comprising a particulate crosslinked body (A2) of the present invention was obtained.

EXAMPLE 3

184 Grams (1 mole) of p-styrenesulfonic acid, 104 g (1 mole) of styrene and 1.8 g of divinylbenzene were dissolved in 500 g of ethyl acetate.

To this monomer solution was added 332 g (0.8 mole) of a 45% ethanol solution of monomethylcarbonate of 1-ethyl-3-methylimidazolium cation (molecular weight: 187) (manufactured by Sanyo Chemical Industries, Ltd.), to substitute a part of protons of sulfonic acid with imidazolium cations.

Nitrogen was passed through this monomer solution to reduce dissolved oxygen, the monomer solution was heated to 60° C. using a water bath, and a polymerization initiator solution in which 0.6 g of azobis-2,4-dimethylvaleronitrile had been diluted with 12 g of ethanol, was added drop wise to perform polymerization. The resulting gel containing toluene was subdivided, and dried at 50° C. under reduced pressure of 100 hectopascal using a vacuum drier, to distill off the solvent.

The dried material was ground using a cutter mill to obtain a non-aqueous absorbent (B3) comprising a particulate crosslinked body (A3) of the present invention having an average particle diameter of 400 μm.

COMPARATIVE EXAMPLE 1

According to the method described in Example 3 of JP-A No. 58-154709, 100 g of a 80% aqueous solution of methacryloxyethyltrimethylammonium chloride which is a monomer having a quaternary amino group, and 0.06 g of N,N-methylenbisacrylamide were mixed and, further, 0.8 g of 2,2'-azobis(2-amidinopropane)hydrochloride as an initiator was added, followed by mixing.

This solution was placed into a box-type container heated by a constant temperature water tank at 85° C., to perform polymerization. The polymer was removed, and ground using a cutter mill to obtain a non-aqueous absorbent (B'-1) comprising a comparative cationic crosslinked body (A'-1) having an average particle diameter of 400 μm.

COMPARATIVE EXAMPLE 2

According to the method described in Example 1 of JP-A No. 60-179410 gazette, 230 ml of cyclohexane and 1.0 g of ethylcellulose were placed into a 500 ml round flask equipped with a stirrer, a condenser and an addition funnel, and a temperature was risen to 75° C.

Separately, 12 g of acrylic acid, 26.2 g of dimethylaminoethyl methacrylate which is a tertially amino group-containing monomer, and 70 g of distilled water were mixed in an Erlenmeyer flask and, further, 5 g of 35% hydrochloric acid and 0.5 g of N,N-methylenebisacrylamide were added to dissolve them uniformly.

To this monomer solution was added 0.02 g of ammonium persulfate as an initiator, and this solution was added drop wise to the round flask over 1.5 hours to perform polymerization.

After polymerization, cyclohexane was removed by decantation, and the resulting bead-like particles were dried at 90° C. using a vacuum drier, to obtain a non-aqueous absorbent (B'-2) comprising a comparative crosslinked body (A'-2) having an average particle diameter of about 200 micron.

COMPARATIVE EXAMPLE 3

According to the method described in Example 1 of JP-A No. 3-221582 gazette, 2 g of completely saponified POVAL, 0.8 g of partially saponified POVAL (saponification degree about 80%) and 300 g of water were placed into a 500 ml round flask equipped with a thermometer, a gas introducing tube and a condenser, nitrogen was introduced therein to substitute dissolved oxygen, and the materials were heated to 40° C.

Thereafter, a solution containing 99.823 g of dodecyl acrylate which is a monomer, 0.177 g of ethylene glycol diacrylate which is a crosslinking agent, and 0.5 g of azobis-2,4-dimethylvaleronitrile which is a polymerization initiator was added to the flask at once, followed by vigorously stirring at a stirring rate of 400 rpm. Then, a temperature of an interior of the flask was risen to 70° C., polymerization was performed at that temperature for 2 hours and, thereafter, a temperature in an interior of the flask was risen to 80° C., and the temperature was maintained for 2 hours to complete polymerization.

After polymerization, the bead-like crosslinked polymer was filtered, particles were washed with water, and dried to obtain a non-aqueous absorbent (B'-3) comprising a particulate comparative crosslinked body (A'-3) having an average particle diameter of about 300 µm.

COMPARATIVE EXAMPLE 4

According to the method described in Example 1 of JP-A No. 11-35632 gazette, a mixed solution containing 99.827 g of methoxyethyl acrylate, 0.173 g of hexanediol diacrylate which is a crosslinking agent, and 0.1 g of azobis-2,4-dimethylvaleronitrile which is an initiator was poured into a glass cast polymerization container (thickness 1 cm) equipped with a thermometer and a gas introducing tube, and the material was heated at 50° C. for 4 hours under a nitrogen stream, to perform polymerization. Thereafter, a temperature was risen to 80° C., and this temperature was maintained for 2 hours to complete polymerization.

The polymer was cooled to 0° C., and ground with a cutter mill to obtain a non-aqueous absorbent (B'-4) comprising a comparative crosslinked body (A'-4) having an average particle diameter of about 500 µm.

COMPARATIVE EXAMPLE 5

According to the method described in Example 8 of JP-A No. 4-230250, 40 g of N-vinylacetamide and 2.0 mg of N,N'-1,4-butylenebisacetamide were dissolved in 150 g of water in a 200 ml three-neck separatable flask equipped with a nitrogen introducing tube, a thermometer and an air discharging port, in a bath maintained at 30° C., and nitrogen was introduced into the system at 1 liter/min to degas dissolved oxygen. Thereafter, 120 mg of 2,2'-azobis(2-amidinopropane) hydrochloride dissolved in 10 mg of degassed water was added, and allowed to stand for 12 hours, to perform polymerization.

The resulting hydrous gel was cut with a mixer equipped with a cutter, washed with acetone, and vacuum-dried at 80° C. for 12 hours. Dried particles were ground with a cutter mill to obtain a non-aqueous absorbent (B'-5) comprising a comparative crosslinked body (A'-5) having an average particle diameter of 400 µm.

COMPARATIVE EXAMPLE 6

According to the same manner as that of Example 1 except that 226.7 g (4 mole) of a 30% aqueous ammonia solution was used in the polymerized gel obtained in Example 1 in place of a 60% methanol solution of methylcarbonate of 1,2,3,4-trimethylimidazolinium cation (manufactured by Sanyo Chemical Industries, Ltd.), a non-aqueous absorbent (B'-6) comprising a comparative crosslinked body (A'-6) having an average particle diameter of 400 µm was obtained.

An amount of absorbing and an amount of holding various organic solvents of the particulate non-aqueous absorbents (B1) to (B3) of the present invention and the non-aqueous absorbents (B'-1) to (B'-6) comprising the comparative particulate crosslinked bodies were measured by the following method. The results are shown in Table 1.

[Measurement of Liquid Absorbing Amount]

1.00 Gram of a particulate non-aqueous absorbent was added to a mesh nylon bag (opening: 75 µm) having a width of 10 cm and a length of 20 cm, the bag was immersed in propylene carbonate for 3 hours, and excessive propylene carbonate was removed for 30 minutes. The same procedure was performed using an empty bag, and a liquid absorbing amount (g/g) was determined by the following equation.

liquid absorbing amount (g/g)=weight of sample bag after swelling−weight of empty bag after immersion

[Measurement of Liquid Holding Amount]

The mesh nylon bag after measurement of an absorbing amount was placed into a centrifugation dehydrating apparatus (manufactured by Kokusan, centrifugation diameter 15 cm), and centrifugation-dehydrated at a rotation rate of 1,500 rpm for 5 minutes. The same procedure was also performed regarding an empty bag after immersion, and a liquid holding amount was determined by the following equation.

Liquid holding amount (g/g)=weight of sample bag after dehydration−weight of empty bag after dehydration Using γ-butyrolactone, methanol and toluene in place of propylene carbonate, the same procedure was performed, and a liquid absorbing amount, and a liquid holding amount for each solvent was determined.

TABLE 1

| | Non-aqueous absorbent | Propylene carbonate | | γ-butyrolactone | | Methanol | | Toluene | |
|---|---|---|---|---|---|---|---|---|---|
| | | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) |
| Example 1 | B1 | 300 | 260 | 160 | 188 | 140 | 121 | 20 | 17 |
| Example 2 | B2 | 140 | 90 | 90 | 73 | 85 | 70 | 16 | 12 |
| Example 3 | B3 | 260 | 222 | 190 | 162 | 110 | 83 | 65 | 50 |

TABLE 1-continued

| | Non-aqueous absorbent | Propylene carbonate Liquid absorbing amount (g) | Propylene carbonate Liquid holding amount (g) | γ-butyrolactone Liquid absorbing amount (g) | γ-butyrolactone Liquid holding amount (g) | Methanol Liquid absorbing amount (g) | Methanol Liquid holding amount (g) | Toluene Liquid absorbing amount (g) | Toluene Liquid holding amount (g) |
|---|---|---|---|---|---|---|---|---|---|
| Comparative Example 1 | B'-1 | 10 | 7 | 13 | 8 | 30 | 21 | 1 | 1 |
| Comparative Example 2 | B'-2 | 12 | 8 | 10 | 7 | 49 | 29 | 2 | 1 |
| Comparative Example 3 | B'-3 | 5 | 3 | 12 | 8 | 13 | 8 | 17 | 14 |
| Comparative Example 4 | B'-4 | 12 | 9 | 13 | 8 | 14 | 10 | 1 | 1 |
| Comparative Example 5 | B'-5 | 12 | 9 | 10 | 7 | 88 | 26 | 2 | 1 |
| Comparative Example 6 | B'-6 | 14 | 10 | 15 | 11 | 27 | 20 | 1 | 1 |

EXAMPLE 4

72 Grams of acrylic acid, 28 g of monomethoxypolyethylene glycol acrylate (Blenmer AME-400, Nippon Oil & Fats Co., Ltd., number average molecular weight of PEG: about 400) and 100 g of methanol were placed into a 1 liter round flask equipped with a stirrer, a nitrogen introducing tube, a condenser, an addition funnel and a thermometer, nitrogen was passed through contents of the flask to substitute dissolved oxygen and, at the same time, a temperature of contents was risen to 50° C. using a water bath tank.

Separately, a solution obtained by dissolving 0.1 g of azobis-2,4-dimethylvaleronitrile which is a polymerization initiator in 9.9 g of methanol was added drop wise over about 2 hours using an addition funnel while stirring under a nitrogen stream, to perform polymerization and, after completion of addition, polymerization was continued at 50° C. for 2 hours, and, thereafter, a temperature was risen to 70° C. to perform polymerization for 2 hours, and polymerization was completed.

After a solution of the produced polymer was cooled to room temperature, 322 g (corresponding to about 0.95 mole) of a 60% methanol solution of methyl carbonate of 1,2,3,4-trimethylimidazolinium cation (molecular weight 203) used in Example 1 was added drop wise to the polymer solution in the round flask using an addition funnel, and occurrence of decarbonization accompanied with addition was observed. After all amount of the imidazolinium cation solution was added drop wise, stirring was continued for about 2 hours to obtain a polymer solution (polymer concentration: about 42%) substituted with imidazolinium cations.

To this polymer solution (100 g) was added 798 g of γ-butyrolactone, the material was heated to 60° C. under reduced pressure to distill off methanol, and a γ-butyrolactone solution having the polymer concentration of 5% was obtained.

To this γ-butyrolactone solution (100 g) was added 0.5 g of polyglycerol polyglycidyl ether (Denacol 521, manufactured by Nagase Chemtex, number of epoxy groups in molecule; 5) used in Example 4, this was placed into a 100 ml sample bottle, the sample bottle was sealed, and the material was heated for 1 hour in a constant temperature tank at 70° C. to perform gelation, to obtain a non-aqueous gel (C1) comprising the non-aqueous absorbent comprising a crosslinked body of the present invention and an organic solvent.

COMPARATIVE EXAMPLE 7

In order to prepare a PEO (polyethylene oxide) system organic solvent-containing gel, 3 g of polyethyleneglycol (molecular weight: 400) monoacrylate and 2 g of polyethylene glycol diacrylate which are the monomer and the crosslinking agent described in Example of JP-A No. 6-68906 gazette, and 95 g of γ-butyrolactone as a solvent were mixed.

To this γ-butyrolactone solution having the monomer concentration of 5% was added 0.05 g of azobis(2,4-dimethylvaleronitrile) which is a polymerization initiator to dissolve them, and then, this was placed into a 100 ml sample bottle, and polymerization was performed at 60° C. for 5 hours under a nitrogen stream, to obtain a comparative non-aqueous gel (C'-1) comprising a non-aqueous absorbent comprising a crosslinked body and an organic solvent.

COMPARATIVE EXAMPLE 8

5 Grams of acryloyltrimethylammonium chloride and 0.1 g of N,N-methylenebisacrylamide as a crosslinking agent were dissolved in 95 g of γ-butyrolactone.

To this γ-butyrolactone solution having the monomer concentration of 5% was added 0.05 g of azobis-2,4-dimethylvaleronitrile which is a polymerization initiator to dissolve them, this was placed into a 100 ml sample bottle, and polymerization was performed at 60° C. for 5 hours under a nitrogen stream, to obtain a comparative non-aqueous gel (C'-2) comprising a non-aqueous absorbent comprising a crosslinked body and an organic solvent.

Regarding the non-aqueous gel (C1) of the present invention prepared in Example 4, and comparative non-aqueous gels (C'-1) and (C'-2) prepared in Comparative Examples 7 and 8, the gelated states immediately after preparation and after with time were measured by the following method. The results are shown in Table 2.

[Method of Measuring Gelated States Immediately After Preparation and After with Time]

The prepared gels were observed, and assessed by the following criteria to obtain the gelated state immediately after preparation.

⊚: Whole is completely gelated, and a gel strength is high.
○: Whole is completely gelated, but a gel strength is low
Δ: A gel is in semi-dissolved state and, when a sample bottle is inverted, a gel flows.
X: Whole is liquid, and is not gelated.

A sample bottle containing the prepared gel was completely sealed, heated for 30 days in a constant temperature tank at 80° C., and the state of a gel after heating was adopted as gelated state after with time.

EXAMPLE 5

18.4 Grams (0.1 mole) of styrenesulfonic acid and 41.8 g (corresponding to 0.102 mole) of a 45% ethanol solution of monomethylcarbonate of 1-ethyl-3-methylimidazolium cation used in Example 3 were added, to completely substitute protons of sulfonic acid with imidazolium cations, and thereafter the material was heated under reduced pressure using a rotary evaporator, to distill off ethanol as a solvent, and methanol produced as a side product.

10 Grams of styrenesulfonic acid monomer in which protons were completely substituted with imidazolium cations was dissolved in 90 g of propylene carbonate in which $LiPF_6$ had been dissolved to the concentration of 1 mol/L (7.2 g/L) in a glove box under an argon gas stream, and 0.1 g of trimethylolpropanetriallyl ether which is a copolymerizing crosslinking agent and 0.1 g of azobis-2,4-dimethylvaleronitrile which is a polymerization initiator were added to dissolve them.

This monomer solution (monomer concentration: 10%) was placed into a 100 ml sample bottle, an argon gas was poured into the monomer solution to substitute dissolved oxygen, the sample bottle was completely sealed, and heated for 5 hours in a constant temperature tank at 60° C., to obtain a non-aqueous gel (C2) comprising a non-aqueous absorbent comprising a crosslinked body of the present invention and an organic solvent.

According to the same manner as that described above except that the monomer concentration was 5%, and propylene carbonate in which $LiPF_6$ had been dissolved to the concentration of 1.5 mol/L (10.8 g/L) was used, a non-aqueous gel (C3) of the present invention comprising a non-aqueous absorbent comprising a crosslinked body of the present invention and an organic solvent was obtained.

COMPARATIVE EXAMPLE 9

According to the same manner as that of Example 5 except that polyethylene glycol (molecular weight: 400) monoacrylate was used in place of styrenesulfonic acid in which protons was substituted with imidazolium cations, a comparative crosslinked non-aqueous gel (C'-3) having the monomer concentration of 10% comprising a non-aqueous absorbent comprising a comparative crosslinked body and an organic solvent, and a crosslinked non-aqueous gel (C'-4) having the monomer concentration of 5% were obtained.

COMPARATIVE EXAMPLE 10

According to the same manner as that of Example 5 except that acryonitrile was used in place of styrenesulfonic acid in which protons were substituted with imidazolium cations, a comparative crosslinked non-aqueous gel (C'-5) having the monomer concentration of 10% comprising a non-aqueous absorbent comprising a crosslinked body and an organic solvent, and a crosslinked non-aqueous gel (C'-6) having the monomer concentration of 5% were obtained.

COMPARATIVE EXAMPLE 11

According to the same manner as that of Example 5 except that acryloyltrimethylammonium chloride was used in place of styrenesulfonic acid in which protons were substituted with imidazolium cations, a non-aqueous gel (C'-7) crosslinked at the monomer concentration of 10% and a non-aqueous gel (C'-8) crosslinked at the monomer concentration of 5%, comprising a non-aqueous absorbent comprising a comparative crosslinked body and an organic solvent were obtained.

Regarding the non-aqueous gels (C2) to (C3) comprising a non-aqueous absorbent of the present invention and an organic solvent obtained by the method of Example 5, and non-aqueous gels (C'-3) to (C'-8) comprising a comparative non-aqueous absorbent and an organic solvent obtained in the methods of Comparative Examples 9 to 11, the gelated states immediately after preparation and after with time were measured by the aforementioned method, and an ionic conductivity of a gel was measured by the following method. The results are shown in Table 2.

[Measurement of Ionic Conductivity of Gel]

The prepared gel was excised into a cylinder having a diameter of 1 cm, this gel was held between platinum electrode discs having a diameter of 1 cm, and an ionic conductivity at 25° C. was measured using an impedance analyzer under the conditions of an application voltage of 0.5 mV and a sweeping frequency of 5 to 13 MHz.

TABLE 2

| Example | Non-aqueous gel | Organic solvent | Polymer concentration % | Gelated state Immediately after preparation | Gelated state After with time | Ionic conductivity of gel (ms/cm) |
|---|---|---|---|---|---|---|
| Example 4 | C1 | γ-butyrolactone | 5 | ⊚ | ⊚ | — |
| Example 5 | C2 | Propylene carbonate | 10 | ⊚ | ⊚ | 4.2 |
|  | C3 | Propylene carbonate | 5 | ⊚ | ⊚ | 7.9 |
| Comparative Example 7 | C'-1 | γ-butyrolactone | 5 | Δ | X | — |
| Comparative Example 8 | C'-2 | γ-butyrolactone | 5 | ○ | X | — |
| Comparative Example 9 | C'-3 | Propylene carbonate | 10 | ○ | Δ | 3.5 |
|  | C'-4 | Propylene carbonate | 5 | X | X | Not gelated Immeasurable |
| Comparative | C'-5 | Propylene carbonate | 10 | ○ | Δ | 3.6 |

TABLE 2-continued

| Example | Non-aqueous gel | Organic solvent | Polymer concentration % | Gelated state Immediately after preparation | After with time | Ionic conductivity of gel (ms/cm) |
|---|---|---|---|---|---|---|
| Example 10 | C'-6 | Propylene carbonate | 5 | X | X | Not gelated Immeasurable |
| Comparative Example 11 | C'-7 | Propylene carbonate | 10 | ○ | X | 3.2 |
| | C'-8 | Propylene carbonate | 5 | X | X | Not gelated Immeasurable |

EXAMPLE 6

72 Grams of acrylic acid, 28 g of monomethoxypolyethylene glycol acrylate (Blenmer AME-400, manufactured by Nippon Oil & Fats Co., Ltd., number average molecular weight of PEG: about 400) and 100 g of methanol were placed into a 1 liter round flask equipped with a stirrer, a nitrogen introducing tube, a condenser, an addition funnel and a thermometer, nitrogen was passed through contents (f the flask to substitute dissolved oxygen and, at the same time, a temperature of contents was risen to 50° C. using a water bath.

Separately, a solution in which 0.1 g of azobis-2,4-dimethylvaleronitrile as a polymerization initiator had been dissolved in 9.9 g of methanol was added drop wise over about 2 hours using an addition funnel while stirring under a nitrogen stream to polymerize, and after completion of addition, polymerization was continued at 50° C. for 2 hours and, thereafter, a temperature was risen to 70° C. to perform polymerization for 2 hours, and polymerization was completed.

After a solution of the produced polymer was cooled to room temperature, 271 g (corresponding to about 0.8 mole) of a 60% methanol solution of methylcarbonate of 1,2,3,4-trimethylimidazolinium cation (molecular weight 203) used in Example 1 was added drop wise to the polymer solution in a round flask using an addition funnel, and occurrence of decarbonization accompanied with addition was observed. After the addition of all imidazolinium cation solution was completed, stirring was continued for about 2 hours to obtain a polymer solution (polymer concentration: about 47%) substituted with imidazolinium cations.

To 100 g of this polymer solution substituted with imidazolinium cations was added 0.047 g of polyglycelol polyglycidyl ether (Denacol 521, manufactured by Nagase Chemkex, number of epoxies: about 5) as a crosslinking agent, and materials were mixed, and thereafter this was coated on a releasing paper at a thickness of 200 μm using a knife coater, and heated and dried for 10 minutes using a circulating air drier at 100° C., to crosslink a polymer and distill off the used methanol.

After drying, the releasing paper was removed from the polymer to obtain a non-aqueous absorbent sheet (D1) comprising the crosslinked body of the present invention having a thickness of about 80 μm. A basis weight of this sheet was measured, and was found to be about 100 g/m².

EXAMPLE 7

A polyester/polyethylene non-woven fabric (Alucima A0404WTO, manufactured by Unitika) having a thickness of 47 μm was immersed in a mixed solution of the polymer solution of imidazolinium cation obtained in Example 4 and polyglycerolpolyglycidyl ether, and then, the immersed non-woven fabric was squeezed using a mangle so as to give an immersion amount of the polymer solution of about 100 g/m² and, thereafter, this was heated and dried for 15 minutes in a circulating air drier at 90° C., to obtain the non-aqueous absorbent sheet (D2) of the present invention having a basis weight of the non-aqueous absorbent of about 47 g/m². A thickness of this sheet was measured, and found to be about 65 μm.

EXAMPLE 8

Polyethylene was sandwich-laminated on one surface of the non-woven fabric used in Example 7 so as to give a thickness of about 10 μm, to prepare a laminate sheet (total thickness: about 55 μm).

The mixed solution of the polymer solution of imidazolinium cation and polyglycerolpolyglycidyl ether obtained in Example 6 was coated on a non-woven fabric surface on which polyethylene was not laminated at a basis amount of the mixed solution of about 100 g/m² using a knife coater.

Thereafter, this was heated and dried for 15 minutes in a circulating air drier at 90° C. to obtain a non-aqueous absorbent sheet (D3) having a basis weight of a non-aqueous absorbent of about 47 g/m². A thickness of this sheet was measured, and was found to be about 75 μm.

EXAMPLE 9

332 Grams (corresponding to 0.8 mole) of the 45% ethanol solution of monomethylcarbonate of 1-ethyl-3-methylimidazolium cation using in Example 3 was added to 84 g (1 mole) of methacrylic acid, to substitute protons of methacrylic acid with imidazolium cations (monomer concentration: about 41%).

To this monomer solution were added 0.1 g of trimethylolpropane triacrylate which is a copolymerizing crosslinking agent and 0.3 g of t-butylperoxy neodecanoate (PerbutylND, manufactured by Nippon Oil & Fats Co., Ltd., 10 hour half life temperature: 46.5° C.) which is a polymerization initiator.

A polyester non-woven fabric (Appeal AN060) having a thickness of about 400 μm was immersed into this monomer solution, and the non-woven fabric was squeezed using a mangle so as to give an immersion amount of the monomer solution of 500 g/m².

This non-woven fabric impregnated with the monomer solution was placed into a forward wind drier in which blast heated at 80° C. was stopped, and polymerization was immediately initiated. Polymerization was performed at this temperature for 30 minutes, and thereafter, blasting was initiated, followed by heating for another 1 hour to complete polymerization. At the same time, ethanol as a solvent was distilled off to obtain a non-aqueous absorbent sheet (D4) containing a non-aqueous absorbent was obtained.

A thickness of this absorbent sheet and a basis weight of the non-aqueous absorbent comprising a crosslinked body of the present invention were measured, and a thickness was found to be about 450 μ, and a basis weight of the non-aqueous absorbent was about 200 g/m².

COMPARATIVE EXAMPLE 12

The non-woven fabric (Alcima A0404WTO) used in Example 7 was adopted as it was as a comparative sheet (D'-1).

COMPARATIVE EXAMPLE 13

The non-woven fabric (Apeel AN040) used in Example 9 was adopted as it was as a comparative sheet (D'-2).

Regarding the absorbent sheets (D1) to (D4) of the present invention described in Examples 6 to 9 and comparative sheets (D'-1) and (D'-2) described in Comparative Examples 12 to 13, a liquid absorbing amount and a liquid holding amount, a liquid absorbing rate, strike-through property and a strike-through rate of the non-aqueous absorbent sheet for an organic solvent were measured by the following method.

[Measurement of Liquid Absorbing Amount and Liquid Holding Amount of Non-Aqueous Absorbent Sheet]

Measurement of a liquid absorbing amount; A sheet cut into 5×5 cm was immersed in propylene carbonate for 3 hours, and then, the sheet was fixed with a clip, excessive propylene carbonate was extracted for 30 minutes, and a liquid absorbing amount (g/cm²) was determined by the following equation.

Liquid absorbing amount (g/cm²)=weight of sheet after swelling/25 (cm²)

Measurement of liquid holding amount: The sheet after measurement of a liquid absorbing amount was placed into a nylon mesh bag, the bag was placed into a centrifugation dehydrating apparatus (manufactured by Kokusan, centrifugation diameter 15 cm), centrifugation-dehydrated for 5 minutes at a rotation speed of 1,500 rpm, and a liquid holding amount was determined by the following equation.

Liquid holding amount (g/cm²)=weight of sample bag after dehydration (g)−weight of empty bag (g)/25 (cm²)

The same procedure was performed using γ-butyrolactone in place of propylene carbonate, a liquid absorbing amount and a liquid holding amount were determined for each solvent.

[Measurement of Liquid Absorbing Rate]

A sheet cut into 5×5 cm was placed on a glass plate, and an end of the sheet was fixed with a cellophane tape so that the sheet was adhered to the glass plate.

1.0 Gram of propylene carbonate was added to a center part of the sheet using a dropper, and a time until an all amount of added propylene carbonate was absorbed in the sheet was adopted as a liquid absorbing rate.

[Measurement of Strike-Through Property and Strike-Through Rate]

Five filters having a diameter of 12.5 cm (manufactured by Advanteck Toyo, NO. 2) were stacked, a sheet cut into 5×5 cm was placed thereon, 1.0 g of propylene carbonate colored with a dye was added to a central part of the sheet using a dropper, and strike-through property of propylene carbonate absorbed in a filter through the sheet, onto a back of the sheet was assessed using the following criteria:

◎: No strike-through
○: Scarce strike-through
Δ: Slight strike-through
X: Much strike-through In addition, by measuring a weight of the filter before and after a test, a strike-through rate was obtained by the following equation.

Strike-through rate (%)={weight of filter after test (g)−weight of filter before test (g))}/weight of added propylene carbonate (g)×100

TABLE 3

| | | Propylene carbonate | | γ-butyrolactone | | | Strike-through test | |
|---|---|---|---|---|---|---|---|---|
| Example | Non-aqueous absorbent sheet | Liquid absorbing amount | Liquid holding amount | Liquid absorbing amount | Liquid holding amount | Liquid absorbing rate (sec) | Strike-through property | Strike-through rate |
| Example 6 | D1 | 30 | 26 | 16 | 14 | 360 | ○ | 0.8 |
| Example 7 | D2 | 20 | 16 | 10 | 8 | 2 | Δ | 6.2 |
| Example 8 | D3 | 18 | 15 | 10 | 8 | 2 | ◎ | 0 |
| Example 9 | D4 | 62 | 53 | 40 | 26 | 1 | ○−Δ | 3.2 |
| Comparative Example 12 | D'-1 | 0.5 | 0.03 | 0.5 | 0.03 | 2 | X | 82.6 |
| Comparative Example 13 | D'-2 | 1.6 | 0.05 | 1.7 | 0.05 | 1 | X | 52.3 |

From Table 1, the following is apparent.

(1) The non-aqueous absorbents (B1) to (B3) of the present invention have a remarkably high liquid absorbing amount and a remarkably high liquid holding amount for a polar solvent such as propylene carbonate, γ-butyrolactone, methanol and the like as compared with comparative non-aqueous absorbents (B'-1) to (B'-6). In particular, a difference is remarkable regarding propylene carbonate and γ-butyrolactone which are used as a solvent of an electrolyte solution.

(2) By making a polymer structure approach a structure of a solvent to be absorbed, it is also possible to absorb or hold an organic solvent having relatively low polarity such as toluene.

From Table 2, the following is apparent.

(1) Non-aqueous gels (C1) to (C3) of the present invention can form a firm gel having a high gel strength which contains a solvent such as γ-butyrolactone and propylene carbonate, even at the low concentration of the non-aqueous absorbent, as compared with comparative non-aqueous gels (C'-1) to (C'-8).

(2) (C1) to (C3) are remarkably excellent in gel stability with time as compared with (C'-1) to (C'-8).

(3) (C2) and (C3) containing a Li ion etc. have a higher ionic conductivity as compared with (C'-3) to (C'-8). In particular, since (C3) can form a firm gel having a high gel strength even in the system where the concentration of a crosslinked body is low and the concentration of a lithium ion is high, it is possible to considerably increase an ionic conductivity of a gel.

From Table 3, the following is apparent.

(1) Non-aqueous absorbent sheets (D1) to (D4) of the present invention have remarkably high liquid absorbing amount and liquid holding amount for propylene carbonate and γ-butyrolactone as compared with comparative sheets (D'-1) and (D'-2). In particular, a difference is especially remarkable regarding liquid holding amount.

(2) (D1) to (D4) have remarkably low strike-through property and strike-through rate of a sheet as compared with (D'-1) and (D'-2). In particular, the absorbent sheet (D3) of the present invention using a non-woven fabric laminated with a polyethylene sheet as a substrate has no strike-through.

(Alcohol-Based Bactericidal Material, Cold Insulating Material, Fuel Composition and Solid Fuel Using the Same, Fuel Store)

EXAMPLES 10 TO 12, COMPARATIVE EXAMPLES 14 TO 19

Various alcohol solvents described in Table 4 were absorbed in the non-aqueous absorbents (B1) to (B3) of Examples 1 to 3, and the non-aqueous absorbents (BA'-1) to (BA'-6) of Comparative Examples 1 to 6, to obtain (BA1) to (BA3) which are the alcohol-based bactericidal material, the cool insulating material, the fuel composition and the fuel store of the present invention, and (BA-1) to (BA'-6) which are comparative alcohol-based bactericidal material, cold insulating material, fuel composition and fuel store.

COMPARATIVE EXAMPLE 20

207 Grams (1 mole) of 2-acrylamido-2-methylpropanesulfonic acid, 72 g (1 mole) of acrylic acid and 1.8 g of divinylbenzene were dissolved in 500 g of a mixed solution of water/isopropyl alcohol (IPA)=50/50.

Nitrogen was passed through this monomer solution to reduce dissolved oxygen, and then, the monomer solution was heated to 60° C. using a water bath, and a polymerization initiator solution obtained by diluting 0.6 g of azobis-2,4-dimethylvaleronitirile with 12 g of ethanol was added drop wise to perform polymerization. The resulting gel containing an IPA aqueous solution was subdivided, and 160 g (1.6 mole) of a 40% aqueous sodium hydroxite (guaranteed reagent) solution was added to substitute a part of protons of sulfonic acid with sodium.

The gel substituted with sodium was dried at 120° C. under reduced pressure at 100 hectopascal using a vacuum drier, to distill off the solvent.

The dried material was ground using a cutter mill to prepared a particulate non-aqueous absorbent having an average particle diameter of 400 μm, and an alcohol solvent was absorbed therein to obtain (BA'-7) which is comparative alcohol-based bactericidal material, cool insulating material, fuel composition or fuel store.

Regarding (BA1) to (BA3) which are the alcohol-based bactericidal material, the cool insulating material, the fuel composition and the fuel store of the present invention of Examples 10 to 12, and (BA'-1) to (BA'-7) which are comparative alcohol-based bactericidal material, cool insulating material, fuel composition and fuel store of Comparative Examples 14 to 20, a liquid absorbing amount and a liquid holding amount for various alcohol solvents described in Table 4 were measured by the following method. The results are shown in Table 4.

[Measurement of Liquid Absorbing Amount and Liquid Holding Amount]

Using a mixed solvent of ethanol/water (mixing ratio=50/50, 75/25 and 100/0), methanol and IPA in place of propylene carbonate in the aforementioned [Measurement of liquid absorbing amount] and [Measurement of liquid holding amount], these amounts were measured according to the aforementioned manner.

TABLE 4

| | | Mixture of ethanol/water | | | | | | Methanol | | Isopropanol | |
| | | 50/50 | | 75/25 | | 100/0 | | | | | |
| Example | Utility material | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) |
| --- | --- | --- | --- | --- | --- | --- | --- | --- | --- | --- | --- |
| Example 10 | BA1 | 300 | 280 | 200 | 180 | 150 | 139 | 220 | 201 | 120 | 107 |
| Example 11 | BA2 | 320 | 300 | 200 | 184 | 170 | 153 | 225 | 197 | 125 | 112 |
| Example 12 | BA3 | 280 | 250 | 170 | 152 | 140 | 127 | 203 | 170 | 110 | 98 |
| Comparative Example 14 | BA'-1 | 20 | 18 | 21 | 18 | 20 | 17 | 23 | 20 | 20 | 17 |
| Comparative Example 15 | BA'-2 | 23 | 19 | 21 | 18 | 20 | 16 | 22 | 18 | 19 | 16 |
| Comparative Example 16 | BA'-3 | 22 | 15 | 20 | 17 | 19 | 15 | 21 | 15 | 20 | 16 |
| Comparative Example 17 | BA'-4 | 24 | 14 | 19 | 17 | 16 | 14 | 20 | 14 | 21 | 13 |
| Comparative | BA'-5 | 28 | 18 | 21 | 15 | 18 | 12 | 22 | 15 | 20 | 14 |

TABLE 4-continued

| | | Mixture of ethanol/water | | | | | | Methanol | | Isopropanol | |
| | | 50/50 | | 75/25 | | 100/0 | | | | | |
| Example | Utility material | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) |
|---|---|---|---|---|---|---|---|---|---|---|---|
| Example 18 Comparative Example 19 | BA'-6 | 5 | 2 | 2 | 1 | 2 | 1 | 2 | 1 | 1 | 1 |
| Comparative Example 20 | BA'-7 | 115 | 100 | 89 | 80 | 78 | 69 | 142 | 125 | 65 | 59 |

From Table 4, the following is apparent.

(1) Non-aqueous absorbents (B1) to (B3) of the present invention have remarkably high liquid absorbing amount and liquid holding amount for water-soluble alcohols such as methanol, ethanol, isopropyl alcohol and the like as compared with comparative non-aqueous absorbents (B'-1) to (B'-7).

(2) The non-aqueous absorbents of the present invention have remarkably high liquid absorbing amount and liquid holding amount for a mixed solvent of ethanol and water which is usually used as a disinfectant or an insecticide.

Therefore, the non-aqueous absorbent of the present invention can be suitably used as a alcohol-based bactericidal material, a cool insulating material, a fuel composition or a fuel store.

EXAMPLE 13

According to the same manner as that of Example 4, a polymer solution (polymer concentration: about 42%) substituted with imidazolinium cations was obtained. 950 Grams of a mixed solvent of ethanol/water=60/40 was added to 100 g of this polymer solution to dissolve the polymer, to obtain a solution having the polymer concentration of 5%.

According to the same manner as that of Example 4, 0.5 g of (aforementioned) polyglycerolpolyglycidyl ether was added to 100 g of this mixed solution to obtain an alcohol-based bactericidal material (BC1) comprising a non-aqueous absorbent and an alcohol solvent.

Separately, according to the same manner except that 950 g of a mixed solvent of ethanol/water/sodium chloride=47.5/47.5/5 was used in place of 950 g of a mixed solvent of ethanol/water=60/40, an integrated gelated-type cold insulating material (BC2) comprising a non-aqueous absorbent and an alcohol solvent was obtained.

Separately, according to the same manner except that 950 g of a mixed fuel of ethanol/water=50/50 was used in place of 950 g of a mixed solvent of ethanol/water=60/40, an integrated gelated-type fuel composition (BC3) was obtained.

Separately, according to the same manner except that 950 g of a mixed fuel of methanol/water=50/50 was used in place of 950 g of a mixed solvent of ethanol/water=60/40, an integrated gelated-type fuel store (BC4) was obtained.

COMPARATIVE EXAMPLE 21

In order to prepare a PEO (polyethylene oxide)-based alcohol solvent-containing gel, 3 g of polyethylene glycol (molecular weight: 400) monoacrylate and 2 g of polyethylene glycol diacrylate which are the monomer and the crosslinking agent described in Example of JP-A No. 6-68906 gazette, and 95 g of a mixed solvent of ethanol/water=60/40 as a solvent were mixed.

0.05 Gram of azobis-2,4-dimethylvaleronitrile which is a polymerization initiator was added to this solution having the monomer concentration of 5% to dissolve the material, this was placed into a 100 ml sample bottle, and polymerization was performed at 60° C. for 5 hours under a nitrogen stream to obtain a comparative integrated gelated-type alcohol-based bactericidal material (BC'-1) comprising a comparative non-aqueous absorbent and an alcohol solvent.

Separately, according to the same manner as that of Example 13 except that each mixed solvent was used, integrated gelated-type cool insulating material (BC'-2), fuel composition (BC'-3) and fuel store (BC'-4) were obtained.

COMPARATIVE EXAMPLE 22

5 Grams of N-vinylacetamide and 0.1 g of N,N-methylenebisacrylamide as a crosslinking agent were dissolved in 95 g of a mixed solvent containing 5% of ethanol/water=60/40.

0.05 Gram of azobis(2,4-dimethylvaleronitrile) which is a polymerization initiator was added to this solution having the monomer concentration of 5% to dissolve the material, this was placed into a 100 ml sample bottle, and polymerization was performed at 60° C. for 5 hours under a nitrogen stream to obtain a comparative integrated gelated-type alcohol-based bactericidal material (BC'-5) comprising a comparative non-aqueous absorbent and an alcohol solvent.

Separately, according to the same manner as that of Example 13 except that each mixed solvent was used, integrated gelated-type cool insulating material (BC'-6), fuel composition (BC'-7) and fuel store (BC'-8) were obtained.

Regarding (BC1) to (BC4) which are the integrated gelated-type alcohol-based bactericidal material, cool insulating material, fuel composition material and fuel store material of the present invention prepared in Example 13, and (BC'-1) to (BC'-8) which are comparative integrated gelated-type alcohol-based bactericidal material, cool insulting material fuel composition and fuel store prepared in Comparative Examples 21 and 22, gelated states immediately after preparation and after with time were measured as described above.

The results are shown in Table 5.

TABLE 5

| Example | Utility material | Alcohol solvent | Polymer concentration (%) | Gelated state Immediately after preparation | Gelated state After with time |
|---|---|---|---|---|---|
| Example 18 | BC1 | Ethanol/water = 60/40 | 5 | ◎ | ◎ |
|  | BC2 | Ethanol/water/sodium chloride = 47.5/47.5/5 | 5 | ◎ | ◎ |
|  | BC3 | Ethanol/water = 50/50 | 5 | ◎ | ◎ |
|  | BC4 | Methanol/water = 60/40 | 5 | ◎ | ◎ |
| Comparative Example 21 | BC'-1 | Ethanol/water = 60/40 | 5 | Δ | X |
|  | BC'-2 | Ethanol/water/sodium chloride = 47.5/47.5/5 | 5 | Δ | X |
|  | BC'-3 | Ethanol/water = 50/50 | 5 | Δ | X |
|  | BC'-4 | Methanol/water = 60/40 | 5 | Δ | X |
| Comparative Example 22 | BC'-5 | Ethanol/water = 60/40 | 5 | ○ | X |
|  | BC'-6 | Ethanol/water/sodium chloride = 47.5/47.5/5 | 5 | ○ | X |
|  | BC'-7 | Ethanol/water = 50/50 | 5 | ○ | X |
|  | BC'-8 | Methanol/water = 60/40 | 5 | ○ | X |

From Table 5, the following is apparent.

(1) The integrated gelated-type alcohol-based bactericidal material, cool insulating material, fuel composition and fuel store of the present invention have a higher strength of a gel containing a solvent such as ethanol alone and a mixed solvent of ethanol and water, and are firm even at the low concentration of a crosslinked body (polymer) as compared with comparative integrated gelated-type alcohol-based bactericidal material, cool insulating material, fuel composition and fuel store.

(2) The integrated gelated-type alcohol-based bactericidal material, cool insulating material, fuel composition and fuel store of the present invention are remarkably excellent in stability after with time, as compared with comparative integrated gelated-type alcohol-based bactericidal material, cool insulating material, fuel composition and fuel store.

EXAMPLE 14

According to the same manner as that of Example 6, a polymer solution (polymer concentration: about 47%) substituted with imidazolinium cations was obtained. 0.047 Gram of the aforementioned polyglycerolpolyglycidyl ether (Denacol 521, described above) which is a reactive crosslinking agent was added to 100 g of this polymer solution substituted with imidazolinium cations, to mix them, the mixture was coated on a releasing paper at a thickness of 200 μm using a knife coater, and heated and dried for 10 minutes using a circulating air drier at 10° C. to perform crosslinking of the polymer and, at the same time, distill off the used methanol. After drying, the releasing paper was removed from the polymer to obtain (BD1) which is the sheet-type alcohol-based bactericidal material, cool insulating material, fuel composition or fuel store having a thickness of about 80 μm. A basis weight of this sheet (BD1) was about 100 g/m².

EXAMPLE 15

The non-aqueous absorbent sheet (D2) obtained in Example 7 was adopted as (BD2) which is a sheet-type alcohol-based bactericidal material, cool insulating material, fuel composition or fuel store.

EXAMPLE 16

The non-aqueous absorbent sheet (D4) obtained in Example 9 was adopted as (BD3) which is a sheet-type alcohol-based bactericidal material, cool insulating material, fuel composition or fuel store.

COMPARATIVE EXAMPLE 23

The non-woven fabric (Alcima A0404WTO) used in Example 7 was adopted as it was as (BD'-1) which is a comparative sheet-type alcohol-based bactericidal material, cool insulating material, fuel composition or fuel store.

COMPARATIVE EXAMPLE 24

The non-woven fabric (Apeel AN040) used in Example 9 was adopted as it was as (BD'-2) which is a comparative sheet-type alcohol-based bactericidal material, cool insulating material, fuel composition or fuel store.

COMPARATIVE EXAMPLE 25

80 Grams (0.8 mole) of a 40% aqueous sodium hydroxide (guaranteed reagent) solution was added to 184 g (1 mole) of p-styrenesulfonic acid to substitute a part of protons with sodium ions, and then, 104 g (1 mole) of styrene, 1.8 g of divinylbenzene and 0.6 g of azobis-2,4-dimethylvaleronitrile were added to dissolved them in 500 g of isopropyl alcohol.

To this monomer solution were added 0.1 g of trimethylolpropane triacrylate which is a copolymerizing crosslinking agent and 0.3 g of t-butylperoxy neodecanoate (Perbutyl ND, manufactured by Nippon Oil & Fats Co., Ltd., 10 hour half life temperature: 46.5° C.) which is a polymerization initiator.

A polyester non-woven fabric (Posibul AK-65N) having a thickness of about 100 μm was impregnated with this monomer solution, and the non-woven fabric was squeezed using a mangle so as to give an impregnation amount of the monomer solution of 300 g/m².

When this non-woven fabric impregnated with the monomer solution was placed into a forward air drier heated at 80° C. in which blasting was stopped polymerization was immediately initiated. After polymerization at this temperature for 30 minutes, blasting was initiated, and the material was further heated for 1 hour to complete polymerization and, at the same time, distill off ethyl acetate as a solvent, to obtain (BD'-3) which is a comparative sheet-type alcohol-based bactericidal material, cool insulating material, fuel composition or fuel store.

A thickness of this sheet (BD'-3) was about 250 μm, and a basis weight was about 100 g/m².

Regarding (BD1) to (BD3) which are the sheet-type alcohol-based bactericidal material, cool insulating material, fuel composition and fuel store of the present invention described in Examples 14 to 16, and (BD'-1) to (BD'-3) which are comparative sheet-type alcohol-based bactericidal material, cool insulating material, fuel composition and fuel store described in Comparative Examples 23 to 25, a liquid absorbing amount and a liquid holding amount for various alcohol solvents were measured by the following method. The results are shown in Table 6.

[Measurement of Liquid Absorbing Amount and Liquid Holding Amount of Absorbent Sheet]

According to the same manner except that a mixed solvent of ethanol/water (mixing ratio=50/50, 75/25 and 100/0), methanol or IPA was used in place of propylene carbonate in the aforementioned [Measurement of liquid absorbing amount and liquid holding amount], a liquid absorbing amount and a liquid holding amount for each solvent were measured.

fabric (100 g/m²)/polyethylene film (20 μm/) thin paper (16 g/m²) at a rate of 25 g/m², an oil resistant paper (45 g/m²) was overlaid thereon, this was cut into 27 mm×27 mm square, heat-sealed, immersed in absolute ethanol for 3 hours, and excessive absolute ethanol was extracted for 30 minutes to obtain an alcohol-based bactericide (E1).

EXAMPLES 18 TO 19

According to the same manner as that of Example 17 except that the absorbent sheet (D1) obtained in Example 6 or the integrated non-aqueous gel (C1) obtained in Example 4 was used in place of the non-aqueous absorbent (B1) in Examples 17, an alcohol-based bactericide (E2) or (E3) was obtained.

COMPARATIVE EXAMPLES 26 TO 28

According to the same manner as that of Example 17 except that the comparative non-aqueous absorbent (B'-1) obtained in Comparative Example 1, the comparative sheet (BD'-1) obtained in Comparative Example 23 or the comparative sheet (BD'-2) obtained in Comparative Example 24 was used in place of the non-aqueous absorbent (B1) in Example 17, comparative alcohol-based bactericides (E'-1), (E'-2) and (E'-3) were obtained.

TABLE 6

| | | Mixture of ethanol/water | | | | | | Methanol | | Isopropanol | |
| | | 50/50 | | 75/25 | | 100/0 | | | | | |
| Example | Utility material | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) |
| --- | --- | --- | --- | --- | --- | --- | --- | --- | --- | --- | --- |
| Example 14 | BD1 | 70 | 58 | 60 | 52 | 55 | 49 | 60 | 54 | 55 | 48 |
| Example 15 | BD2 | 35 | 30 | 30 | 24 | 25 | 22 | 30 | 27 | 25 | 20 |
| Example 16 | BD3 | 120 | 100 | 105 | 95 | 95 | 88 | 125 | 120 | 98 | 90 |
| Comparative Example 23 | BD'-1 | 2 | 1 | 2 | 1 | 2 | 1 | 2 | 1 | 2 | 1 |
| Comparative Example 24 | BD'-2 | 2 | 1 | 2 | 1 | 2 | 1 | 2 | 1 | 1 | 1 |
| Comparative Example 25 | BD'-3 | 15 | 15 | 20 | 17 | 19 | 15 | 21 | 15 | 20 | 15 |

From Table 6, the following is apparent.

(1) The sheet-type alcohol-based bactericidal material, cool insulating material, fuel composition and fuel store of the present invention have a remarkably higher liquid absorbing amount for ethanol alone or a mixed solvent of ethanol and water, as compared with comparative sheet-type alcohol-based bactericidal material, cool insulating material, fuel composition and fuel store.

(2) The present invention has also remarkably high liquid absorbing amount and liquid holding amount for a mixed solvent of ethanol and water which is usually used as a disinfectant, an insecticide or a cool insulator.

(Alcohol-Based Bactericide)

EXAMPLE 17

The non-aqueous absorbent (B1) obtained in Example 1 was uniformly spread on a laminate film of rayon non-woven

COMPARATIVE EXAMPLE 29

A commercially available food freshness retaining agent Antimold 102 (manufactured by Freund Corporation, bag size 45 mm×65 mm) containing 0.6 g of ethanol was adopted as a comparative alcohol-based bactericide (E'-4).

Regarding the alcohol-based bactericides (E1) to (E3) of the present invention described in Examples 17 to 19, and comparative bactericides (E'-1) to (E'-4) shown in Comparative Examples 26 to 29, an ethanol releasing test and a fungistatic effect test were performed by the following method.

[Ethanol Releasing Test]

A moisture activity adjusting medium obtained by adding 100 g of water to 3.9 g of potato dextrose and 75 g of sucrose and adjusting a pH with an aqueous NaOH solution was used. Moisture activity of this medium was measured with a moisture activity measuring devise (manufactured by Freund Corporation; FWA-200), and was found to 0.90. Separately, a bacterial solution was prepared by dissolving one platinum loop of separated Penicillum notatumu in 50 ml of a saline, and diluting 1 ml of this solution with 200 ml of a sterilized saline. Then, 1 ml of the bacterial solution was placed in a sterilized petri dish (diameter 95 mm. depth 20 mm; manufactured by Aiken Kizai Co., Ltd.) and, then, about 50 g of the aforementioned moisture activity adjusting medium was flown into this petri dish. The bacterial solution and the medium were mixed in the petri dish, and the mixture was allowed to stand for 2 hours to obtain a bacterium seeding petri dish.

Two packing bags having an internal sizes of 155 mm×210 mm composed of a film obtained by laminating a KOP film (polypropylene coated with polyvinylidene chloride) and a LLDPE film (straight low density polyethylene) were prepared, any one of the above-obtained molded products (E1) to (E3), and (E'-1) to (E'-4), and one bacterium seeding petri dish were accommodated in each packing bag, and this was heat-sealed. The thus obtained three packing bags were allowed to stand in a constant temperature bath at 25° C. and, 1, 5, 10, 15 and 20 days after allowing to stand, the concentration of an ethanol steam in the packing bag was measured by the following method. The results are shown in Table 7.

Measurement of the concentration of an ethanol steam was performed using gas chromatography. The measuring conditions were as follows:

Measuring apparatus; GC-14A (FID) (manufactured by Simadzu Corporation)
Filler; PEG-20M 10%
Carrier; Chromosorb WAW DMCS
Column; SUS 2 m×3 mm
Carrier gas; $N_2$ 1.4 kg/cm$^2$
   $H_2$ 1.0 kg/cm$^2$
   Air 1.0 kg/cm$^2$
Temperature of sample injecting part and detecting part; 150° C.
Column temperature, 80° C.

In Table 7, the concentration of an ethanol steam is expressed by %.

TABLE 7

| Example | Alcohol-based insecticide | Lapsed days (day) | | | | |
|---|---|---|---|---|---|---|
| | | 1 | 5 | 10 | 15 | 20 |
| Example 17 | E1 | 0.32 | 0.55 | 0.54 | 0.49 | 0.45 |
| Example 18 | E2 | 0.50 | 0.52 | 0.60 | 0.57 | 0.54 |
| Example 19 | E3 | 0.45 | 0.75 | 0.73 | 0.65 | 0.59 |
| Comparative Example 26 | E'-1 | 0.10 | 0.05 | 0.03 | 0.02 | 0.01 |
| Comparative Example 27 | E'-2 | 0.15 | 0.11 | 0.08 | 0.05 | 0.03 |
| Comparative Example 28 | E'-3 | 0.18 | 0.14 | 0.10 | 0.08 | 0.05 |
| Comparative Example 29 | E'-4 | 0.40 | 0.45 | 0.44 | 0.38 | 0.32 |

[Assessment of Fungistatic Effect]

Growth state of fungus in a bacterium seeding petri dish was assessed based on the following criteria, and fungistatic effect was assessed. The results are shown in Table 8. In addition, the result of the case where only a bacterium seeding petri dish was placed in the packing bag is adopted Comparative Example 30.

TABLE 8

| | | 1 | | 5 | | 10 | | 20 | |
|---|---|---|---|---|---|---|---|---|---|
| Example | Alcohol-based bacteriocide | Determination | Colony diameter (mm) | Determination | Colony diameter (mm) | Determination | Colony diameter (mm) | Determination | Colony diameter (mm) |
| Example 17 | E1 | — | | — | | — | | — | |
| Example 18 | E2 | — | | — | | — | | — | |
| Example 19 | E3 | — | | — | | — | | — | |
| Comparative Example 26 | E'-1 | — | | + | 3 | ++ | 7 | +++ | 14 |
| Comparative Example 27 | E'-2 | — | | + | 4 | ++ | 8 | +++ | 12 |
| Comparative Example 28 | E'-3 | — | | + | 2 | ++ | 4 | +++ | 12 |
| Comparative Example 29 | E'-4 | — | | — | | — | | — | |
| Comparative Example 30 | — | ++ | 5 | ++ | 10 | +++ | 13 | +++ | 16 |

— Growth of fungus is not recognized at all.
+ Slight growth of fungus is recognized.
++ Growth of fungus has progressed.
+++ Growth of fungus has considerably progressed.

From Table 7 and Table 8, the following is apparent.

(1) The alcohol-based bactericide of the present invention has a greater ethanol releasing rate as compared with the previous freshness retaining agent.

(2) Further, the alcohol-based bactericide of the present invention can exert performance equivalent to or superior over that of the prior agent also regarding fungistatic effect.

(Cold Insulator)

EXAMPLE 20

Using a polyethylene (50 μm)/polyester (12 μm)/aluminum foil (7 μm)/polyethylene (12 μm) laminate (ethanol gas permeability 0.7 g/m$^2$ under RH 50%, 40° C. and 24 hours) as a steam impermeable substrate, a bag for a cold insulator was made. A gel-like cold insulating material comprising the 1 g of non-aqueous absorbent (B1) obtained in Example 1, 5 g of sodium chloride and 95 g of a 50% aqueous ethanol solution was placed in the bag, and an opening portion was heat-sealed to obtain a cold insulator (F1) of the present invention.

EXAMPLES 21 AND 22

According to the same manner as that of Example 20 except that the non-aqueous absorbent sheet (D1) or the non-aqueous gel (C1) obtained in Example 6 or 4 was used in place of the non-aqueous absorbent (B1) in Example 20, the cold insulators (F2) and (F3) of the present invention were obtained.

COMPARATIVE EXAMPLES 31 TO 33

According to the same manner as that of Example 20 except that the comparative non-aqueous absorbent (B'-1), sheet (D'-1) or non-aqueous gel (C'-2) obtained in Comparative Example 1, 12 or 8 was used in place of the non-aqueous absorbent (B1) in Example 20, comparative cold insulators (F'-1), (F'-2) and (F'-3) were obtained.

Regarding the cold insulators of the present invention of Examples 20 to 22 and the comparative cold insulators of Comparative Examples 31 to 33, an alcohol volatilization test and a durability test of a cold insulator were performed by the following methods.

[Alcohol Volatilization Test]

Each cold insulator was heated to 40° C., decrease in a weight of the cold insulator was measured, an alcohol volatilization amount was obtained, and a remaining weight rate of an aqueous ethanol solution was obtained by the following equation. The results are shown in Table 9.

Remaining weight rate (%)=(weight of cold insulator before heating/weight of cold insulator after heating)×100

[Durability Test of Cold Insulator]

Each cold insulator was allowed to stand at −30° C. for 16 hours and at 25° C. for 8 hours, and this procedure was repeated 100 times, and then, circumstance of water separation, touch feeling and softness were assessed by the following criteria. The results are also shown in Table 9.

TABLE 9

| Example | Cold insulator | Remaining weight rate of prepared solution (%) | | | | | Water separation | Touch feeling | Softness |
| --- | --- | --- | --- | --- | --- | --- | --- | --- | --- |
| | | Initiation day | After 2 weeks | After 1 month | After 2 months | After 3 months | | | |
| Example 20 | F1 | 100 | 99.99 | 99.99 | 99.99 | 99.99 | ○ | ○ | ○ |
| Example 21 | F2 | 100 | 99.98 | 99.98 | 99.97 | 99.97 | ○ | ○ | ○ |
| Example 22 | F3 | 100 | 99.99 | 99.99 | 99.99 | 99.99 | ○ | ○ | ○ |
| Comparative Example 31 | F'-1 | 100 | 99.98 | 99.97 | 99.97 | 99.96 | Δ | Δ | Δ |
| Comparative Example 32 | F'-2 | 100 | 99.98 | 99.98 | 99.97 | 99.97 | Δ | Δ | X |
| Comparative Example 33 | F'-3 | 100 | 99.97 | 99.96 | 99.95 | 99.95 | X | X | X |

Water separation
○ No water separation.
Δ Slight water separation.
X Much water separation.
Touch feeling
○ Better touch feeling.
Δ Slightly hard.
X Hard.
Softness
○ Bent well.
Δ Difficult to bent.
X Is not bend.

From Table 9, the following is apparent.

(1) The cool insulator of the present invention causes no decrease in a weight and is stable over a long term.

(2) The cool insulator of the present invention is excellent in capability of absorbing an ethanol/sodium chloride aqueous solution having the high concentration, causes no water separation, and is excellent in touch feeling and softness, as compared with previous cool insulator.

(Solid Fuel)

EXAMPLE 23

Using a cellophane (20 μm)/polypropylene (20 μm)/polyethylene (40 μm) laminate (ethanol gas permeability of 0.5 g/m² under RH50%, 40° C. and 24 hours) as a steam impermeable substrate, a bag for a solid fuel was made. A gel-like fuel composition comprising 2 g of the non-aqueous absorbent (B1) and 98 g of a 80% aqueous ethanol solution was placed into this bag, and an opening portion was heat-sealed to obtain the solid fuel (G1) of the present invention.

EXAMPLE 24

According to the same manner as that of Example 23 except that the sheet (BD1) of Example 14 was used in place of the non-aqueous absorbent (B1), the solid fuel (G2) of the present invention was obtained.

EXAMPLE 25

According to the same manner as that of Example 23 except that the integrated gelated-type fuel composition (BC3) of Example 13 was used in place of the non-aqueous absorbent (B1) and a 80% aqueous ethanol solution, the solid fuel (G3) of the present invention was obtained.

COMPARATIVE EXAMPLES 34 TO 35

According to the same manner as that of Example 23 except that the non-aqueous absorbent (B'-1) of Comparative Example 1 or the sheet (BD'-1) of Comparative Example 23 was respectively used in place of the non-aqueous absorbent (B1), comparative solid fuels (G'-1) and (G'-2) were obtained.

COMPARATIVE EXAMPLE 36

According to the same manner as that of Example 23 except that the sheet (BD'-2) of Comparative Example 24 was used in place of the non-aqueous absorbent (B1) and a 80% aqueous ethanol solution, the comparative solid fuel (G'-3) was obtained.

COMPARATIVE EXAMPLE 37

100 Grams of a commercially available solid fuel in a tube, as it was, was used as a comparative solid fuel (G'-4).

Regarding the solid fuels (G1) to (G3) of the present invention and the comparative solid fuels (G'-1) to (G'-4), an alcohol fuel evaporation test and a combustion test were performed by the following methods. The results are shown in Table 10.

[Alcohol Fuel Evaporation Test]

Each solid fuel was heated to 40° C., decrease in a weight of a solid fuel was measured, an amount of an evaporated alcohol fuel was obtained, and a remaining weight rate of an alcohol fuel was obtained by the following equation.

Remaining weight rate (%)=(weight of solid fuel before heating/weight of solid fuel after heating)×100

[Combustion Fuel]

Each solid fuel was placed into a container made of an aluminum foil, this was ignited, a combustion time was measured, and at the same time, the status at combustion was observed and assessed based on the following criteria.

From Table 10, the following is apparent.

(1) The solid fuel accommodated in a steam impermeable substrate of the present invention does not cause change in a weight due to evaporation of an alcohol fuel, and becomes a solid fuel excellent in long term storage stability.

(2) Since the solid fuel accommodated in a steam impermeable substrate of the present invention can retain a large amount of alcohol fuel as compared with the comparative solid fuels (G'-1) to (G'-3) and the previous solid fuel (G'-4), a fuel does not ooze out during combustion, and combustion over a long term becomes possible.

(Gel Sheet for Cooling)

EXAMPLES 26 TO 28

Various alcohol solvents described in Table 11 were absorbed in the non-aqueous absorbents (B1) to (B3) of Examples 1 to 3 to obtain gel layers (L1) to (L3) of a gel sheet for cooling.

COMPARATIVE EXAMPLES 38 TO 44

Various alcohol solvents described in Table 11 were absorbed in a commercially available crosslinked polyvinylcarboxylic acid amide-based liquid absorbing resin NA010 (manufactured by SHOWA DENKO K.K.), the non-aqueous absorbent (B'-5) of Comparative Example 5, a commercially available crosslinked sodium polyacrylate-based water-absorbing resin Sanfresh ST-500D (manufactured by Sanyo Chemical Industries, Co., Ltd.), a commercially available gelatin, the non-aqueous absorbent (B'-3) of Comparative Example 3, the non-aqueous absorbent (B'-6) of Comparative Example 6, and (BA'-7) of Comparative Example 20 to obtain gel layers (L'-1) to (L'7) of comparative gel sheets for cooling.

Regarding the gel layers (L1) to (L3) of gel sheets for cooling in the present invention, and gel layers (L'-1) to (L'-7) of comparative gel sheets for cooling, a liquid absorbing amount and a liquid holding amount for various alcohol solvents were measured as in measurement of a liquid absorbing amount and a liquid holding amount of ethanol/water. The results are shown in Table 11.

TABLE 10

| | | Remaining weight rate of alcohol fuel (%) | | | | | | |
|---|---|---|---|---|---|---|---|---|
| Example | Solid fuel | Initiation date | After 2 weeks | After 1 month | After 2 months | After 3 months | Combustion time (min) | Combustion state |
| Example 23 | G1 | 100 | 99.99 | 99.99 | 99.99 | 99.99 | 30 | ◎ |
| Example 24 | G2 | 100 | 99.98 | 99.98 | 99.97 | 99.97 | 28 | ◎ |
| Example 25 | G3 | 100 | 99.99 | 99.99 | 99.99 | 99.99 | 31 | ◎ |
| Comparative Example 34 | G'-1 | 100 | 99.98 | 99.97 | 99.97 | 99.96 | 14 | X |
| Comparative Example 35 | G'-2 | 100 | 99.98 | 99.98 | 99.97 | 99.97 | 15 | X |
| Comparative Example 36 | G'-3 | 100 | 99.97 | 99.96 | 99.95 | 99.95 | 13 | X |
| Comparative Example 37 | G'-4 | 100 | 0 | 0 | 0 | 0 | 13 | ○ |

◎ Clearly burnt while retaining a shape to the last.
○ On the way, a fuel slightly oozes out.
Δ A fuel oozes out, a shape is slightly disintegrated.
X A fuel oozes out, a shape is not retained at all.

TABLE 11

| Example | Gel layer of gel sheet | Mixture of ethanol/water 50/50 | | 75/25 | | 100/0 | | Methanol | | Isopropanol | |
|---|---|---|---|---|---|---|---|---|---|---|---|
| | | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) |
| Example 26 | L1 | 300 | 280 | 200 | 180 | 150 | 139 | 220 | 201 | 120 | 107 |
| Example 27 | L2 | 320 | 300 | 200 | 184 | 170 | 153 | 225 | 197 | 125 | 112 |
| Example 28 | L3 | 280 | 250 | 170 | 152 | 140 | 127 | 203 | 170 | 110 | 98 |
| Comparative Example 38 | L'-1 | 20 | 18 | 21 | 18 | 20 | 17 | 23 | 20 | 20 | 17 |
| Comparative Example 39 | L'-2 | 23 | 19 | 21 | 18 | 20 | 16 | 22 | 18 | 19 | 16 |
| Comparative Example 40 | L'-3 | 22 | 15 | 20 | 17 | 19 | 15 | 21 | 15 | 20 | 16 |
| Comparative Example 41 | L'-4 | 24 | 14 | 19 | 17 | 16 | 14 | 20 | 14 | 21 | 13 |
| Comparative Example 42 | L'-5 | 28 | 18 | 21 | 15 | 18 | 12 | 22 | 15 | 20 | 14 |
| Comparative Example 43 | L'-6 | 5 | 2 | 2 | 1 | 2 | 1 | 2 | 1 | 1 | 1 |
| Comparative Example 44 | L'-7 | 115 | 100 | 89 | 80 | 78 | 69 | 142 | 125 | 65 | 59 |

EXAMPLE 29

According to the same manner as that of Example 4, an integrated gelated-type gel layer (LC1) comprising a non-aqueous absorbent and an alcohol solvent was obtained.

COMPARATIVE EXAMPLE 45

According to the same manner as that of Comparative Example 7, an integrated gelated-type gel layer (LC'-1) comprising a non-aqueous absorbent and an alcohol solvent was obtained.

COMPARATIVE EXAMPLE 46

According to the same manner as that of Comparative Example 22, an integrated gelated-type gel layer (LC'-2) comprising a non-aqueous absorbent and an alcohol solvent was obtained.

Regarding the aforementioned gel layer (LC1) of a sheet for cooling and the gel layers (LC'-1) and (LC'-2) of the comparative sheets for cooling, gelated states immediately after preparation and after with time were measured as described above. The results are shown in Table 12.

TABLE 12

| | Integrated gelated-type gel layer | Alcohol solvent | Polymer concentration (%) | Gelated state Immediately after preparation | After with time |
|---|---|---|---|---|---|
| Example 29 | LC1 | Ethanol/water = 50/50 | 5 | ◎ | ◎ |
| Comparative Example 45 | LC'-1 | | | Δ | X |
| Comparative Example 46 | LC'-2 | | | ○ | X |

EXAMPLES 30 TO 32

According to the same manners as those of Examples 14, 7 and 9, sheet-type gel layers (LD1) to (LD3) were obtained.

COMPARATIVE EXAMPLES 47 TO 49

According to the same manners as those of Comparative Examples 12, 13 and 25, comparative sheet-type gel layers (LD'-1) to (LD'-3) were obtained.

Regarding respective sheet-type gel layers of Examples 30 to 32, and Comparative Examples 47 to 49, a liquid absorbing amount and a liquid holding amount for various alcohol solvents described in Table 13 were measured as described above. The results are shown in Table 13.

sheet for cooling of Comparative Example 38 was used in place of the non-aqueous absorbent (B1), the comparative gel sheet for cooling (M'-1) was obtained.

COMPARATIVE EXAMPLE 51

According to the same manner as that of Example 34 except that the sheet-type gel layer (LD'-3) of Comparative Example 49 was used in place of the sheet, (BD1), the gel sheet for cooling (M'-2) was obtained.

COMPARATIVE EXAMPLE 52

According to the same manner as that of Example 35 except that the integrated gelated-type gel layer (LC'-1) of

TABLE 13

| | | Mixture of ethanol/water | | | | | | Methanol | | Isopropanol | |
| | | 50/50 | | 75/25 | | 100/0 | | | | | |
| Example | Sheet-type gel layer | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) |
|---|---|---|---|---|---|---|---|---|---|---|---|
| Example 30 | LD1 | 70 | 58 | 60 | 52 | 55 | 49 | 60 | 54 | 55 | 48 |
| Example 31 | LD2 | 35 | 30 | 30 | 24 | 25 | 22 | 30 | 27 | 25 | 20 |
| Example 32 | LD3 | 120 | 100 | 105 | 95 | 95 | 88 | 125 | 120 | 98 | 90 |
| Comparative Example 47 | LD'-1 | 2 | 1 | 2 | 1 | 2 | 1 | 2 | 1 | 2 | 1 |
| Comparative Example 48 | LD'-2 | 2 | 1 | 2 | 1 | 2 | 1 | 2 | 1 | 2 | 1 |
| Comparative Example 49 | LD'-3 | 15 | 15 | 20 | 17 | 19 | 15 | 21 | 15 | 20 | 15 |

EXAMPLE 33

The non-aqueous absorbent (B1) obtained in Example 1 was uniformly spread on a rayon non-woven fabric (100 g/m$^2$) at a ratio of 25 g/m$^2$, an oil resistant paper (45 g/m$^2$) was overlaid thereon, this was cut into 100 mm×100 mm square, heat-sealed, and 5.0 g of an aqueous ethanol solution (ethanol/water=60:40) was absorbed therein to obtain the gel sheet for cooling (M1) of the present invention.

EXAMPLE 34

5.0 Grams of an aqueous ethanol solution (ethanol/water=60/40) was absorbed in the sheet (BD1) obtained in Example 14, to obtain the gel sheet for cooling (M2) of the present invention.

EXAMPLE 35

A rayon non-woven fabric was adhered on one surface of the non-aqueous absorbent sheet (D4) of Example 9 with gum arabic, and 5.0 g of an aqueous ethanol solution (ethanol/water=60/40) was absorbed in the non-aqueous absorbent sheet (D4), to obtain the gel sheet for cooling (M3) of the present invention.

COMPARATIVE EXAMPLE 50

According to the same manner as that of Example 33 except that the gelated layer (L'-1) of the comparative gel Comparative Example 45 was used in place of the non-aqueous absorbent sheet (D4), the comparative gel sheet for cooling (M'-3) was obtained.

Regarding the gel sheets for cooling (M1) to (M3) of the present invention, and the comparative gel sheets for cooling (M'-1) to (M'-3), a cooling test and a freezing test were performed by the following methods. The results are shown in Table 14.

[Cooling Test]

Each gel sheet for cooling was allowed to stand for 1 hour in a refrigerator at 4° C. After taken out in a room, a temperature sensor (RTH-1010 manufactured by ESPEC Corporation) was mounted on a non-woven fabric surface of the gel sheet, and a temperature of the surface was measured with a thermorecorder (RS-11 manufactured by ESPEC Corporation) every hour until 6 hours passed.

[Freezing Test]

Each gel sheet for cooling was allowed to stand for 24 hours in a refrigerator at –18° C. After taken out in a room, the gel status was judged based on the following criteria.

TABLE 14

| Gel sheet for cooling | | Temperature every hour passage | | | | | | | Frozen status |
|---|---|---|---|---|---|---|---|---|---|
| | | 0 (hr) | 1 | 2 | 3 | 4 | 5 | 6 | |
| Example 33 | M1 | 4 | 7 | 10 | 14 | 18 | 22 | 25 | ◯ |
| Example 34 | M2 | 4 | 6 | 9 | 12 | 15 | 20 | 24 | ◯ |
| Example 35 | M3 | 4 | 8 | 10 | 13 | 17 | 21 | 25 | ◯ |

TABLE 14-continued

| | Gel sheet for cooling | Temperature every hour passage | | | | | | | Frozen status |
|---|---|---|---|---|---|---|---|---|---|
| | | 0 (hr) | 1 | 2 | 3 | 4 | 5 | 6 | |
| Comparative Example 50 | M'-1 | 4 | 15 | 25 | 25 | 25 | 25 | 25 | Δ |
| Comparative Example 51 | M'-2 | 4 | 15 | 24 | 25 | 25 | 25 | 25 | X |
| Comparative Example 52 | M'-3 | 4 | 15 | 25 | 25 | 25 | 25 | 25 | X |

○ Not frozen.
Δ Not frozen, but the sheet has no softness.
X Frozen.

From Tables 11 to 14, the following is apparent.

(1) The gel sheet for cooling of the present invention has long lasting cooling capability.

(2) The gel sheet for cooling of the present invention is not frozen even when stored in a refrigerator, and is excellent in softness.

(Fragrance Material and Fragrance)

EXAMPLES 36 TO 38

Rosemary aromatic drugs described in Table 15 were absorbed in the non-aqueous absorbents (B1) to (B3) of Examples 1 to 3, to obtain fragrance materials (N1) to (N3).

COMPARATIVE EXAMPLES 53 TO 59

Rosemary aromatic drugs described in Table 15 were absorbed in a commercially available crosslinked polyvinylcarboxylic acid amide-based liquid absorbing resin NA010 (SHOWA DENKO K.K.), the non-aqueous absorbent (B'-5) of Comparative Example 5, a commercially available crosslinked sodium polyacrylate-based water-absorbing resin Sanfresh ST-500D (manufactured by Sanyo Chemical Industries Co., Ltd.), commercially available gelatin, the known-aqueous absorbent (B'-3) of Comparative Example 3, the non-aqueous absorbent (B'-6) of Comparative Example 6, and (BA'-7) of Comparative Example 20, to obtain fragrance materials (N'-1) to (N'-7).

Regarding a particulate non-aqueous absorbent in the fragrance materials (N1) to (N3) of the present invention of Examples 36 to 38, and fragrance materials (N'-1) to (N'-7) of Comparative Examples 53 to 59, a liquid absorbing amount and a liquid holding amount for various rosemary aromatic drugs were measured as in the aforementioned measurement of a liquid absorbing amount and a liquid holding amount. The results are shown in Table 15.

TABLE 15

| | | Aromatic drug solution | | | | | | | | | |
|---|---|---|---|---|---|---|---|---|---|---|---|
| | | Mixture of ethanol/water/rosemary | | | | | | Methanol/rosemary | | IPA/rosemary | |
| | | 49/49/2 | | 59/39/2 | | 98/0/2 | | 95/5 | | 95/5 | |
| | Fragrance material | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) |
| Example 36 | N1 | 280 | 260 | 200 | 180 | 150 | 139 | 222 | 201 | 120 | 107 |
| Example 37 | N2 | 270 | 240 | 200 | 184 | 170 | 153 | 225 | 197 | 125 | 112 |
| Example 38 | N3 | 280 | 250 | 170 | 152 | 140 | 127 | 203 | 170 | 110 | 98 |
| Comparative Example 53 | N'-1 | 20 | 18 | 21 | 18 | 20 | 17 | 23 | 20 | 20 | 17 |
| Comparative Example 54 | N'-2 | 23 | 19 | 21 | 18 | 20 | 16 | 22 | 18 | 19 | 16 |
| Comparative Example 55 | N'-3 | 22 | 15 | 20 | 17 | 19 | 15 | 21 | 15 | 20 | 16 |
| Comparative Example 56 | N'-4 | 24 | 14 | 19 | 17 | 16 | 14 | 20 | 14 | 21 | 13 |
| Comparative Example 57 | N'-5 | 28 | 18 | 21 | 15 | 18 | 12 | 22 | 15 | 20 | 14 |
| Comparative Example 58 | N'-6 | 5 | 2 | 2 | 1 | 2 | 1 | 2 | 1 | 1 | 1 |
| Comparative Example 59 | N'-7 | 115 | 100 | 89 | 80 | 78 | 69 | 142 | 125 | 65 | 59 |

EXAMPLE 39

740 Grams of a mixed solvent of ethanol/water/lemongrass oil=50/40/10 was added to 100 g of a polymer solution (polymer concentration: about 42%) substituted with imidazolinium cations obtained as in Example 4, to dissolve the polymer, to obtain a solution having the polymer concentration of 5%. 0.5 Gram of the aforementioned polyglycerolpolyglycidyl ether used in Example 4 was added to 100 g of this mixed solution, this was placed into a 100 ml sample bottle, the sample bottle was sealed, heated for 1 hour in a constant temperature bath at 70° C., to gelate the sample, to obtain the integrated gelated-type fragrance material (NC1) of the present invention with a lemongrass oil aromatic drug absorbed therein.

COMPARATIVE EXAMPLE 60

According to the same manner as that of Comparative Example 7 except that a mixed solvent of ethanol/water/lemongrass oil=50/40/10 was used in place of γ-butyrolactone as a solvent in Comparative Example 7, the comparative integrated gelated-type fragrance material (NC'-1) was obtained.

COMPARATIVE EXAMPLE 61

According to the same manner as that of Comparative Example 22 except that a mixed solvent of ethanol/water/lemongrass oil=50/40/10 was used in place of a mixed solvent of ethanol/water=50/50 in Comparative Example 22, the comparative integrated gelated-type fragrance (NC'-2) was obtained.

Regarding the aforementioned integrated gelated-type fragrance material (NC1) and the comparative integrated gelated-type fragrance materials (NC'-1) and (NC'-2), gelated states immediately after preparation and after with time were measured as described above. The results are shown in Table 16.

EXAMPLES 40 TO 42

Cypress oil—based aromatic drugs described in Table 17 were absorbed in the non-aqueous absorbent sheets (D1), (D2) and (D4) obtained in Examples 6, 7 and 9, to obtain the sheet-type fragrance materials (ND1) to (ND3) of the present invention.

COMPARATIVE EXAMPLES 62 TO 64

Cypress oil—based aromatic drugs described in Table 17 were absorbed in the sheets (D'-1) and (D'-2) used in Comparative Examples 12 and 13, and the sheet (BD'-3) obtained in Comparative Example 25, the comparative sheet-type fragrance materials (ND'-1) to (ND'-3) were obtained.

Aromatic drugs described in Table 17 were absorbed in the sheet-type fragrance materials of Examples 40 to 42, and Comparative Examples 62 to 64, and a liquid absorbing amount and a liquid holding amount were measured as described above. The results are shown in Table 17.

TABLE 16

| | Integrated gelated-type fragrance material | Aromatic drug solution | Polymer concentration (%) | Gelated status | |
|---|---|---|---|---|---|
| | | | | Immediately after preparation | After with time |
| Example 39 | NC1 | Ethanol/water/lemongrass oil = 50/40/10 | 5 | ◎ | ◎ |
| Comparative Example 60 | NC'-1 | | | Δ | X |
| Comparative Example 61 | NC'-2 | | | ○ | X |

TABLE 17

| Example | Sheet-type fragrance | Mixture of ethanol/water/cypress oil | | | | | | Methanol/cypress oil | | IPA/cypress oil | |
|---|---|---|---|---|---|---|---|---|---|---|---|
| | | 49/49/2 | | 74/24/2 | | 98/0/2 | | 95/5 | | 95/5 | |
| | | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) |
| Example 40 | ND1 | 70 | 58 | 60 | 52 | 55 | 49 | 60 | 54 | 55 | 48 |
| Example 41 | ND2 | 35 | 30 | 30 | 24 | 25 | 22 | 30 | 27 | 25 | 20 |
| Example 42 | ND3 | 120 | 100 | 105 | 95 | 95 | 88 | 125 | 120 | 98 | 90 |
| Comparative Example 62 | ND'-1 | 2 | 1 | 2 | 1 | 2 | 1 | 2 | 1 | 2 | 1 |
| Comparative Example 63 | ND'-2 | 2 | 1 | 2 | 1 | 2 | 1 | 2 | 1 | 1 | 1 |
| Comparative Example 64 | ND'-3 | 15 | 15 | 20 | 17 | 19 | 15 | 21 | 15 | 20 | 15 |

EXAMPLE 43

The non-aqueous absorbent (B1) obtained in Example 1 was uniformly spread on a rayon non-woven fabric (100 g/m$^2$) at a ratio of 25 g/m$^2$, an oil resistant paper (45 g/m$^3$) was overlaid thereon, this was cut into 100 mm×100 mm square, heat-sealed and immersed in an aromatic drug solution (ethanol/water/lemongrass oil=60/30/10) to obtain a fragrance (Q1).

EXAMPLE 44

The non-aqueous absorbent sheet (BD1) obtained in Example 14 was immersed in an aromatic drug solution (ethanol/water/lemongrass oil=60/30/10) to obtain the fragrance (Q2) of the present invention.

EXAMPLE 45

The integrated gelated-type fragrance material (NC1) of Example 39 was adopted as a fragrance (Q3).

COMPARATIVE EXAMPLE 65

According to the same manner as that of Example 43 except that the fragrance material (N'-1) of Comparative Example 53 was used in place of the non-aqueous absorbent (B1), the comparative fragrance (Q'-1) was obtained.

COMPARATIVE EXAMPLE 66

According to the same manner as that of Example 44 except that the sheet-type fragrance material (ND'-3) of Comparative Example 64 was used in place of the non-aqueous absorbent sheet (BD1), the fragrance (Q'-2) was obtained.

COMPARATIVE EXAMPLE 67

The integrated gelated-type fragrance material (NC'-1) of Comparative Example 60 was adopted as a comparative fragrance (Q'-3).

Regarding the fragrances (Q1) to (Q3) of the present invention of Examples 43 to 45, and the comparative fragrances (Q'-1) to (Q'-3) of Comparative Examples 65 to 67, a volatilization test was performed by the following method.

[Volatilization Test]

The fragrances (Q1) to (Q3) and (Q'-1) to (Q'-3) were arranged on a center of a bottom of a 50 liter plastic desiccator, and the desiccator was sealed. This was allowed to stand in a constant temperature constant humidity bath regulated at a temperature of 28° C. and a relative humidity of 60% RH. After 1, 2, 4, 8 and 12 weeks from the initiation of this allowing to stand, the desiccator was opened, a weight of a fragrance every term was measured, and a volatilized amount (mg) was determined. The results were shown in Table 18.

TABLE 18

| | Fragrance | After 1 week | After 2 weeks | After 4 weeks | After 8 weeks | After 12 weeks |
|---|---|---|---|---|---|---|
| Example 43 | Q1 | 20 mg | 40 | 85 | 180 | 300 |
| Example 44 | Q2 | 18 | 37 | 75 | 150 | 240 |
| Example 45 | Q3 | 15 | 32 | 65 | 130 | 200 |
| Comparative Example 65 | Q'-1 | 15 | 32 | 10 | 5 | 5 |
| Comparative Example 66 | Q'-2 | 10 | 5 | 5 | 3 | 2 |
| Comparative Example 67 | Q'-3 | 7 | 4 | 4 | 2 | 1 |

EXAMPLE 46

According to the same manner as that of Example 43 except that the sheet-type fragrance material (ND1) of Example 40 was used in place of the non-aqueous absorbent (B1), the fragrance (Q4) of the present invention was obtained.

EXAMPLE 47

According to the same manner as that of Example 43 except that the integrated gelated-type fragrance material (NC1) of Example 39 was used in place of the non-aqueous absorbent (B1), the fragrance (Q5) of the present invention was obtained.

COMPARATIVE EXAMPLE 68

According to the same manner as that of Example 43 except that the sheet-type fragrance material (ND'-3) of Comparative Example 64 was used in place of the non-aqueous absorbent (B1), the fragrance (Q'-4) was obtained.

COMPARATIVE EXAMPLE 69

According to the same manner as that of Example 43 except that the integrated gelated-type fragrance material (NC'-1) of Comparative Example 60 was used in place of the non-aqueous absorbent (B1), the comparative fragrance (Q'-5) was obtained.

Regarding the fragrances (Q4) and (Q5) of the present invention of Examples 46 to 47, and the comparative fragrances (Q'-4) to (Q'-5) of Comparative Examples 68 to 69, a volatilization test was performed as in the aforementioned volatilization test. The results are shown in Table 19.

TABLE 19

| | Fragrance | After 1 week | After 2 weeks | After 4 weeks | After 8 weeks | After 12 weeks | After 24 weeks |
|---|---|---|---|---|---|---|---|
| Example 46 | Q-4 | 15 mg | 30 | 62 | 135 | 200 | 420 |
| Example 47 | Q-5 | 12 | 25 | 52 | 100 | 150 | 320 |
| Comparative Example 68 | Q'-4 | 14 | 13 | 12 | 8 | 5 | 3 |
| Comparative Example 69 | Q'-5 | 6 | 4 | 4 | 2 | 1 | 1 |

From Tables 15 to 19, the following is apparent.

Since the fragrance of the present invention has a large amount of holding an aromatic drug, aroma releasing ability lasts over a long term. Further, when used by accommodating in an external material comprising a steam permeable substrate, since a steam permeating amount can be regulated, a fragrance which can maintain aroma effect for a further long term can be provided.

(Patch Materials and Patches)

EXAMPLES 48 TO 50

Percutaneous absorption drugs described in Table 20 were absorbed in the non-aqueous absorbents (B1) to (B3) of Examples 1 to 3, to obtain patch materials (R1) to (R3).

COMPARATIVE EXAMPLES 70 TO 76

Percutaneous absorption drugs described in Table 20 were absorbed in a commercially available crosslinked polyvinylcarboxylic acid amide-based liquid absorbing resin NA010 (SHOWA DENKO K.K.), the non-aqueous absorbent (B'-5) of Comparative Example 5, a commercially available crosslinked sodium polyacrylate-based water-soluble resin Sunfrash ST-500 D (manufactured by Sanyo Chemical Industries Co., Ltd.), commercially available gelatin, the non-aqueous absorbent (B'-3) of Comparative Example 3, the non-aqueous absorbent (B'-6) of Comparative Example 6, and (BA'-7) of Comparative Example 20, to obtain patch materials (R'-1) to (R-7).

Regarding patch materials (R1) to (R3) of the present invention of Examples 48 to 50, and the comparative patch materials (R'-1) to (R'-7) of Comparative Examples 70 to 76, a liquid absorbing amount and a liquid holding amount for mixed solvents described in Table 20 were measured as in the aforementioned liquid absorbing amount and liquid holding amount. The results are shown in Table 20.

TABLE 20

| | | Mixture of ethanol/indometacin | | | | | | Methanol/indometacin | | Isopropanol/indometacin | |
|---|---|---|---|---|---|---|---|---|---|---|---|
| | | 50/50 | | 75/25 | | 25/75 | | 95/5 | | 95/5 | |
| | | Liquid | Liquid | Liquid | Liquid | Liquid | Liquid | Liquid | Liquid | | |
| Example | Patch material | absorbing amount (g) | holding amount (g) | absorbing amount (g) | holding amount (g) | absorbing amount (g) | holding amount (g) | absorbing amount (g) | holding amount (g) | Liquid absorbing amount (g) | Liquid holding amount (g) |
| Example 48 | R1 | 150 | 140 | 180 | 160 | 120 | 109 | 200 | 181 | 100 | 87 |
| Example 49 | R2 | 160 | 100 | 180 | 164 | 100 | 83 | 202 | 181 | 94 | 14 |
| Example 50 | R3 | 140 | 125 | 170 | 152 | 90 | 77 | 203 | 189 | 88 | 64 |
| Comparative Example 70 | R'-1 | 20 | 18 | 21 | 18 | 20 | 17 | 23 | 20 | 10 | 6 |
| Comparative Example 71 | R'-2 | 23 | 19 | 21 | 18 | 20 | 16 | 22 | 18 | 11 | 5 |
| Comparative Example 72 | R'-3 | 22 | 15 | 20 | 17 | 19 | 15 | 21 | 15 | 10 | 4 |
| Comparative | R'-4 | 24 | 14 | 19 | 17 | 16 | 14 | 20 | 14 | 12 | 4 |

TABLE 20-continued

| | | Mixture of ethanol/indometacin | | | | | | Methanol/ indometacin | | Isopropanol/ indometacin | |
| | | 50/50 | | 75/25 | | 25/75 | | 95/5 | | 95/5 | |
| | | Liquid | Liquid | Liquid | Liquid | Liquid | Liquid | Liquid | Liquid | | |
| Example | Patch material | absorbing amount (g) | holding amount (g) | absorbing amount (g) | holding amount (g) | absorbing amount (g) | holding amount (g) | absorbing amount (g) | holding amount (g) | Liquid absorbing amount (g) | Liquid holding amount (g) |
|---|---|---|---|---|---|---|---|---|---|---|---|
| Example 73 | | | | | | | | | | | |
| Comparative Example 74 | R'-5 | 10 | 4 | 15 | 7 | 8 | 3 | 11 | 5 | 10 | 5 |
| Comparative Example 75 | R'-6 | 5 | 2 | 2 | 1 | 2 | 1 | 2 | 1 | 1 | 1 |
| Comparative Example 76 | R'-7 | 15 | 7 | 20 | 11 | 12 | 4 | 18 | 9 | 12 | 7 |

EXAMPLE 51

740 Grams of a mixed solvent of ethanol/water/methyl salicylate=60/30/10 was added to 100 g of a polymer solution (polymer concentration: about 42%) substituted with imidazolinium cations obtained as in Example 4, to dissolve the polymer, to obtain a solution having the polymer concentration of 5%. To 100 g of this mixed solution was added 0.5 g of the aforementioned polyglycerolpolyglycidyl ether (described-above) used in Example 4, this was placed into a 100 ml sample bottle, the sample bottle was sealed, the bottle was heated for 1 hour in a constant temperature bath at 70° C. to gelate the material, to obtain the integrated gelated-type patch material (RC1) of the present invention with methyl salicylate-based percutaneous absorption drug absorbed therein.

COMPARATIVE EXAMPLE 77

According to the same manner as that of Comparative Example 7 except that a mixed solvent of ethanol/water/methyl salicylate=60/30/10 was used in place of γ-butyrolactone as a solvent, the comparative integrated gelated-type patch material (RC'-1) was obtained.

COMPARATIVE EXAMPLE 78

According to the same manner as that of Comparative Example 22 except that a mixed solvent of ethanol/water/methyl salicylate=60/30/10 was used in place of ethanol/water=60/40, the comparative integrated gelated-type patch material (RC'-2) was obtained.

Regarding the integrated gelated-type patch material (RC1) of Example 51 and the comparative integrated gelated-type patch materials (RC'-1) and (RC'-2) of Comparative Examples 77 and 78, gelated states immediately after preparation and after with time were measured as described above. The results are shown in Table 21.

TABLE 21

| | Integrated gelated-type patch material | Percutaneous absorption drug | Polymer concentration (%) | Gelated status | |
| | | | | Immediately after preparation | After with time |
|---|---|---|---|---|---|
| Example 51 | RC1 | Ethanol/water/ methyl salicylate = 60/30/10 | 5 | ◎ | ◎ |
| Comparative Example 77 | RC'-1 | | | Δ | X |
| Comparative Example 78 | RC'-2 | | | ○ | X |

EXAMPLES 52 TO 54

Methyl salicylate-based percutaneous absorption drugs described in Table 22 were absorbed in the non-aqueous absorbent sheets (D1), (D2) and (D4) obtained in Examples 6, 7 and 9, to obtain the sheet-type patch materials (RD1) to (RD3) of the present invention.

COMPARATIVE EXAMPLES 79 TO 81

Methyl salicylate-based percutanesou absorption drugs described in Table 22 were absorbed in the sheets used in Comparative Examples 12 and 13 and the sheet-type gel layer (LD'-3) obtained in Comparative Example 49, to obtain the comparative sheet-type patch materials (RD'-1) to (RD'-3).

Regarding the sheet-type patch materials (RD1) to (RD3) of the present invention of Examples 52 to 54, and the comparative sheet-type patch materials (RD'-1) to (RD'-3) of Comparative Examples 79 to 81, a liquid absorbing amount and a liquid holding amount were measured as in the aforementioned liquid absorbing amount and liquid holding amount. The results are shown in Table 22.

TABLE 22

| Example | Sheet-type patch material | Mixture of ethanol/methyl salicylate | | | | | | Mixture of ethanol/methyl salicylate | | Mixture of IPA/methyl salicylate | |
|---|---|---|---|---|---|---|---|---|---|---|---|
| | | 50/50 | | 75/25 | | 25/75 | | 95/5 | | 95/5 | |
| | | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) |
| Example 52 | RD1 | 70 | 58 | 60 | 52 | 55 | 49 | 60 | 54 | 50 | 41 |
| Example 53 | RD2 | 35 | 30 | 30 | 24 | 25 | 22 | 30 | 27 | 25 | 20 |
| Example 54 | RD3 | 60 | 50 | 54 | 35 | 45 | 32 | 125 | 120 | 53 | 39 |
| Comparative Example 79 | RD'-1 | 2 | 1 | 2 | 1 | 2 | 1 | 2 | 1 | 2 | 1 |
| Comparative Example 80 | RD'-2 | 2 | 1 | 2 | 1 | 2 | 1 | 2 | 1 | 1 | 1 |
| Comparative Example 81 | RD'-3 | 12 | 8 | 11 | 7 | 10 | 5 | 15 | 10 | 10 | 4 |

EXAMPLE 55

The non-aqueous absorbent (B1) obtained in Example 1 was uniformly spread on a rayon non-woven fabric (100 g/m$^2$) at a ratio of 25 g/m$^2$, an oil resistant paper (45 g/m$^2$) was overlaid thereon, cut into 100 mm×100 mm square, heat-sealed, and immersed into a percutaneous absorption drug (ethanol/indometacin=50/50) to obtain a patch (S1).

EXAMPLE 56

The non-aqueous absorbent sheet (BD1) obtained in Example 14 was immersed into a percutaneous absorption drug (ethanol/indometacin=50/50) to obtain a patch (S2).

EXAMPLE 57

The integrated gelated-type patch material (RC1) of Example 51 was adopted as an integrated gelated-type patch (S3).

COMPARATIVE EXAMPLE 82

According to the same manner as that of Example 55 except that the patch material (R'-1) of Comparative Example 70 was used in place of the non-aqueous absorbent (B1), the comparative patch (S'-1) was obtained.

COMPARATIVE EXAMPLE 83

According to the same manner as that of Example 55 except that a sheet-type gel layer (LD'-3) of Comparative Example 49 was used in place of the non-aqueous absorbent (B1), the patch (S'-2) was obtained.

COMPARATIVE EXAMPLE 84

The integrated gelated-type patch material (RC'-1) of Comparative Example 77 was adopted as a comparative patch (S'-3).

An amount of holding a percutaneous absorption drug for the patches (S1) to (S3) of the present invention of Examples 55 to 57, and the comparative patches (S'-1) to (S'-3) of Comparative Examples 82 to 84 was measured by the following method.

[Method of Measuring Amount of Holding Percutaneous Absorption Drug]

Each patch was sealed in an aluminum bag, stored under the condition of 50° C., and a content of indometacin in each patch was measured by high speed liquid chromatography initially, and 5 days, 10 days, 20 days and 30 days after. Letting an initial content to be 1.00, a relative ratio is shown in Table 23.

TABLE 23

| | | Lapsed days | | | | |
|---|---|---|---|---|---|---|
| | Patch | Initial | 5 days | 10 days | 20 days | 30 days |
| Example 55 | S1 | 1.00 | 1.00 | 1.00 | 1.00 | 0.99 |
| Example 56 | S2 | 1.00 | 1.00 | 1.00 | 1.00 | 0.98 |
| Example 57 | S3 | 1.00 | 1.00 | 1.00 | 1.00 | 1.00 |
| Comparative Example 82 | S'-1 | 1.00 | 0.58 | 0.32 | 0.10 | 0.01 |
| Comparative Example 83 | S'-2 | 1.00 | 0.11 | 0.08 | 0.02 | 0.01 |
| Comparative Example 84 | S'-3 | 1.00 | 0.70 | 0.04 | 0.21 | 0.10 |

EXAMPLE 58

5.0 Grams of the non-aqueous absorbent (B1) obtained in Example 1, 2.25 g of polyvinyl alcohol, 1.2 g of tartaric acid, 20 g of concentrated glycerin, 20 g of a 70% D-sorbitol solution, 3.0 g of kaolin, 0.1 g of sodium edetate, 1.5 g of methyl salicylate and an appropriate amount of a 60% aqueous ethanol solution were uniformly mixed to obtain an ointment for patch. This ointment was spread on a non-woven fabric to obtain a patch (S4) according to the conventional method.

EXAMPLE 59

According to the same manner as that of Example 58 except that the non-aqueous absorbent (B2) of Example 2 was used in place of the non-aqueous absorbent (B1), a patch (S5) was obtained.

COMPARATIVE EXAMPLE 85

2.25 Grams of polyvinyl alcohol, 1.2 g of tartaric acid, 20 g of concentrated glycerin, 3.0 g of CMC, 5.0 g of partially neutralized polyacrylic acid, 20 g of a 70% D-sorbitol solution, 3.0 g of kaolin, 0.1 g of sodium edetate, 0.08 g of methasilicate aluminate metal salt, 1.5 g of methyl salicylate, and an appropriate amount of purified water were uniformly mixed to obtain an ointment for a patch. This ointment was spread on a non-woven fabric, to obtain the comparative patch (S'-4) by the conventional method.

COMPARATIVE EXAMPLE 86

According to the same manner as that of Comparative Example 85 except that a 60% aqueous ethanol solution was used in place of purified water, the comparative patch (S'-5) was obtained.

COMPARATIVE EXAMPLE 87

According to the same manner as that of Comparative Example 85 except that thermally crosslinked CMC used in Example 1 of JP-A No. 2000-95678 gazette was used in place of CMC, and a 60% aqueous ethanol solution was used in place of purified water, the comparative patch (S'-6) was obtained.

Each of patches of Examples 58 to 69, and Comparative Examples 85 to 87 was applied to panelers (male 5, female 5) appealing inferior limb pain, to attach one patch to an inferior limb pain place. Upon application for 12 hours, comfortableness, effectiveness feeling, skin adherability, and a pain at peeling of a patch regarding each patch were assessed by the following assessing methods. The results are shown in Table 24.

TABLE 24

| | Patch | Comfortableness | Effectiveness feeling | Skin adherability | Pain when peeled |
|---|---|---|---|---|---|
| Example 58 | S4 | ○ | ○ | ○ | ○ |
| Example 59 | S5 | ○ | ○ | ○ | ○ |
| Comparative Example 85 | S'-4 | Δ | X | ○ | Δ |
| Comparative Example 86 | S'-5 | Δ | X | Δ | Deteriorated adherability Not assessed |
| Comparative Example 87 | S'-6 | Δ | X | ○ | Δ |

Comfortableness
After attachment of a patch, comfortableness one our later was assessed by the following 3 grades.
○ Refreshness
Δ Slight refreshness
X No refreshness
Effectiveness feeling
After attachment of a patch, whether there remains effectiveness feeling 12 hours later was assessed by the following 3 grades.
○ Effectiveness feeling
Δ Slight effectiveness feeling
X No effectiveness feeling
Skin adherability
Upon attachment of a patch, adherability to a skin was assessed by the following 3 grades.
○ Better adherability
Δ Slightly peeled state
X No adherability, peeled state

TABLE 24-continued

| | Patch | Comfortableness | Effectiveness feeling | Skin adherability | Pain when peeled |
|---|---|---|---|---|---|

Pain upon peeling
A pain when a patch was peeled was assessed by the following 3 grades.
○ No pain is felt.
Δ Slight pain is felt, but satisfactory level.
X A half of peelers feel a pain.

From Table 20 to Table 24, the following is apparent.

(1) Whether the sheet-type or the integrated gelated-type, the patch material of the present invention has a remarkably higher liquid absorbing amount and liquid holding amount for a percutaneous absorption drug as compared with the comparative patch material.

(2) Since the integrated gelated-type patch material of the present invention is a firm gel having a higher gel strength which contains a percutaneous absorption drug, even at the lower concentration of a non-aqueous absorbent, as compared with the comparative integrated gelated-type patch material, stability of a gel with time is remarkably excellent.

(3) In the patch of the present invention, reduction in a content of a contained percutaneous absorption drug with time is suppressed, and a large amount of a perucutaneous absorption drug can be stably retained.

(4) Since the patch of the present invention can contain a large amount of a percutaneous absorption drug, it is possible to have long lasting drug efficacy such as inflammatory effect, analgesic effect and the like.

(Insecticidal Compositions and Insecticides)

EXAMPLES 60 TO 62

Pyrethroid insecticidal ingredients described in Table 25 were absorbed in the non-aqueous absorbents (B1) to (B3) of Examples 1 to 3, to obtain insecticidal compositions (T1) to (T3).

COMPARATIVE EXAMPLES 88 TO 94

Pyrethroid insecticidal ingredients described in Table 25 were absorbed in the non-aqueous absorbents (B'-1) to (B'-4) of Comparative Examples 1 to 4, "Oleosoap PW-190" (acrylic polymer-based crosslinked polymer; manufactured by Nippon Shokubai Co., Ltd.), the non-aqueous absorbent (B'-6) of Comparative Example 6, and (BA'-7) of Comparative Example 20, to obtain comparative insecticidal compositions (T'-1) to (T'-7).

Regarding the non-aqueous absorbents of Examples 60 to 62, and Comparative Examples 88 to 94, a liquid absorbing amount and a liquid holding amount were measured as in the aforementioned liquid absorbing amount and liquid holding amount. The results are shown in Table 25.

TABLE 25

| Example | Insecticidal composition | Mixture of ethanol/allethrin (or empenthrin) | | | | | | Methanol/allethrin (or empenthrin) | | Isopropanol/allethrin (or empenthrin) | |
| | | 50/50 | | 75/25 | | 25/75 | | 50/50 | | 50/50 | |
| | | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) |
|---|---|---|---|---|---|---|---|---|---|---|---|
| Example 60 | T1 | 300 | 280 | 200 | 180 | 150 | 139 | 220 | 201 | 100 | 87 |
| Example 61 | T2 | 320 | 300 | 200 | 184 | 170 | 153 | 225 | 197 | 94 | 74 |
| Example 62 | T3 | 280 | 250 | 170 | 152 | 140 | 127 | 203 | 170 | 88 | 64 |
| Comparative Example 88 | T'-1 | 20 | 18 | 21 | 18 | 20 | 17 | 23 | 20 | 10 | 6 |
| Comparative Example 89 | T'-2 | 23 | 19 | 21 | 18 | 20 | 16 | 22 | 18 | 11 | 5 |
| Comparative Example 90 | T'-3 | 22 | 15 | 20 | 17 | 19 | 15 | 21 | 15 | 10 | 4 |
| Comparative Example 91 | T'-4 | 24 | 14 | 19 | 17 | 16 | 14 | 20 | 14 | 12 | 4 |
| Comparative Example 92 | T'-5 | 10 | 4 | 15 | 7 | 8 | 8 | 11 | 5 | 10 | 5 |
| Comparative Example 93 | T'-6 | 5 | 2 | 2 | 1 | 2 | 1 | 2 | 1 | 1 | 1 |
| Comparative Example 94 | T'-7 | 15 | 7 | 20 | 11 | 12 | 4 | 18 | 9 | 12 | 7 |

EXAMPLE 63

740 Grams of a mixed solvent of phenoxyethanol/allethrin (or empenthrin)=50/50 was added to 100 g of a polymer solution (polymer concentration: about 42%) substituted with imidazolinium cations obtained as in Example 4 to dissolve the polymer, to obtain a solution having the polymer concentration of 5%. To 100 g of this mixed solution was added 0.5 g of the polyglycerolpolyglycidyl ether (described-above) used in Example 4, this was placed into a 100 ml sample bottle, the sample bottle was sealed, and heated for 1 hour in a constant temperature bath at 70° C. to gelate the material, to obtain an integrated gelated-type insecticidal composition (TC1).

COMPARATIVE EXAMPLE 95

According to the same manner as that of Comparative Example 7 except that a mixed solvent of phenoxyethanol/allethrin or empenthrin)=50/50 was used in place of γ-butyrolactone as a solvent, the comparative integrated gelated-type insecticidal composition (TC'-1) was obtained.

COMPARATIVE EXAMPLE 96

According to the same manner as that of Comparative Example 22 except that a mixed solvent of phenoxyethanol/allethrin (or empenthrin)=50/50 was used in place of ethanol/water=50/50, the comparative integrated gelated-type insecticidal composition (TC'-2) was obtained.

Regarding the integrated gelated-type insecticidal composition (TC-1) of Example 63, and comparative integrated gelated-type insecticidal compositions (TC'-1) and (TC'-2) of Comparative Examples 95 and 96, gelated states immediately after preparation and after with time were measured as described above. The results are shown in Table 26.

TABLE 26

| | Integrated gelated-type insecticidal composition | Insecticide solution | Polymer concentration (%) | Gelated status | |
| | | | | Immediately after preparation | After with time |
|---|---|---|---|---|---|
| Example 63 | TC1 | Phenoxyethanol/allethrin (or empenthrin) = 50/50 | 5 | ◎ | ◎ |
| Comparative Example 95 | TC'-1 | | | Δ | X |
| Comparative Example 96 | TC'-2 | | | ◯ | X |

EXAMPLES 64 TO 66

Transfurfurin mixed solvents described in Table 27 were absorbed in the non-aqueous absorbent sheets (D1), (D2) and (D4) obtained in Examples 6, 7 and 9 to obtain the sheet-type insecticidal compositions (TD1) to (TD3) of the present invention.

COMPARATIVE EXAMPLES 97 TO 99

Transfurfurin mixed solvents described in Table 27 were absorbed in the sheets used in Comparative Examples 12 and 13 and the sheet (BD'-3) obtained in Comparative Examples 25 to obtain the comparative sheet-type insecticidal compositions (TD'-1) to (TD'-3).

Regarding the sheet-type insecticidal compositions (TD1) to (TD3) of Example 64 to 66, and the sheet-type insecticidal compositions (TD'-1) to (TD'-3) of Comparative Examples 97 to 99, a liquid absorbing amount and a liquid holding amount were measured as in the aforementioned liquid absorbing amount and liquid holding amount. The results are shown in Table 27.

throid insecticidal ingredient solution was extracted to obtain the insecticide (U2) of the present invention.

EXAMPLE 69

The integrated gelated-type insecticidal composition (TC1) of Example 63 was adopted as insecticide (U3) of the present invention.

COMPARATIVE EXAMPLES 100 TO 103

According to the same manner as that of Example 67 except that the insecticidal composition (T'-1) of Comparative Example 88, the sheet-type insecticidal composition (TD'-1) of Comparative Example 97, the integrated gelated-type insecticidal composition (TC'-2) of Comparative Example 96 or Oleosoap PW-190 (manufactured by Nippon Shokubai Co., Ltd.) was used in place of the non-aqueous absorbent (B1), comparative insecticides (U'-1) to (U'-4) were obtained.

Regarding the insecticides (U1) to (U3) of the present invention and the comparative insecticides (U'-1) to (U'-4), a

TABLE 27

| | | Mixture of ethanol/transfurfurin | | | | | | Mixture of methanol/transfurfurin | | Mixture of IPA/transfurfurin | |
| | | 50/50 | | 75/25 | | 25/75 | | 50/50 | | 50/50 | |
| Example | Sheet-type insecticidal composition | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) | Liquid absorbing amount (g) | Liquid holding amount (g) |
|---|---|---|---|---|---|---|---|---|---|---|---|
| Example 64 | TD1 | 70 | 58 | 60 | 52 | 55 | 49 | 60 | 54 | 50 | 41 |
| Example 65 | TD2 | 35 | 30 | 30 | 24 | 25 | 22 | 30 | 27 | 25 | 20 |
| Example 66 | TD3 | 60 | 50 | 54 | 35 | 45 | 32 | 125 | 120 | 53 | 39 |
| Comparative Example 97 | TD'-1 | 2 | 1 | 2 | 1 | 2 | 1 | 2 | 1 | 2 | 1 |
| Comparative Example 98 | TD'-2 | 2 | 1 | 2 | 1 | 2 | 1 | 2 | 1 | 1 | 1 |
| Comparative Example 99 | TD'-3 | 12 | 8 | 11 | 7 | 10 | 5 | 15 | 10 | 10 | 4 |

EXAMPLE 67

The non-aquous absorbent (B1) obtained in Example 1 was uniformly spread on a laminate film of rayon non-woven fabric (100 g/m$^2$)/polyethylene film (20 μm)/thin paper (16 g/m$^2$) at a rate of 400 g/m$^2$, an oil resistant paper (45 g/m$^2$) was overlaid thereon, cut into 23 mm×35 mm square, heat-sealed, immersed in a pyrethroid insecticidal ingredient solution [allethrin (or empenthrin)/phenoxyethanol=50/50] for 3 hours, and then, an excessive amount of the pyrethroid insecticidal ingredient solution was extracted to obtain the insecticide (U1) of the present invention.

EXAMPLE 68

The non-aqueous absorbent sheet (D1) obtained in Example 6 was immersed in a pyrethroid insecticidal ingredient solution [allethrin (or empenthrin)/phenoxyethanol=50/50] for 3 hours, and an excessive amount of the pyrenormal temperature volatilization test, a heating release test and an insecticidal effect test were performed by the following methods.

[Normal Temperature Volatilization Test]

A packing bag of an internal size of 155 mm×210 mm comprising a film obtained by laminating a KOP film (polypropylene coated with polyvinylidene chloride) and a LLDPE film (straight low density polyethylene) was prepared, the above-obtained insecticides of Examples 67 to 69, and Comparative Examples 100 to 103 were accommodated in each packing bag, and heat-sealed. The thus obtained packing bag containing an insecticide was allowed to stand in a constant temperature bath at 25° C., and the concentration of an empenthrin steam in the packing bag was measured by the following method after 1, 10, 30, 60 and 90 day from allowing to stand.

Empenthrin was measured using gas chromatography. The measuring conditions were the same as those for the aforementioned measurement of an ethanol steam.

The results are shown in Table 28. In Table 28, the concentration of empenthrin is expressed by %.

TABLE 28

|  | Insecticide | Lapsed days | | | | |
| --- | --- | --- | --- | --- | --- | --- |
|  |  | Initial | 10 days | 30 days | 60 days | 90 days |
| Example 67 | U1 | 0.32 | 0.55 | 0.54 | 0.49 | 0.45 |
| Example 68 | U2 | 0.50 | 0.52 | 0.60 | 0.57 | 0.54 |
| Example 69 | U3 | 0.45 | 0.75 | 0.73 | 0.65 | 0.59 |
| Comparative Example 100 | U'-1 | 0.10 | 0.05 | 0.03 | 0.02 | 0.01 |
| Comparative Example 101 | U'-2 | 0.15 | 0.11 | 0.08 | 0.05 | 0.03 |
| Comparative Example 102 | U'-3 | 0.18 | 0.14 | 0.10 | 0.08 | 0.05 |
| Comparative Example 103 | U'-4 | 0.40 | 0.45 | 0.44 | 0.38 | 0.32 |

[Heating Release Test]

Each of insecticides of Examples 67 to 69, and Comparative Examples 100 to 103 was filled into an aluminum container having a size of a bottom of 23 mm×35 mm and a height of 10 mm, thereafter, the aluminum container was placed on a heating release apparatus provided with a radiating plate of a size of 24 mm×36 mm having a central part heated at 90° C., and release performance was measured. For measuring an insecticidal ingredient, the insecticidal ingredient was trapped with a column filled with silica gel every predetermined time, the insecticidal ingredient was extracted with acetone, and then, analyzed under the same conditions as those for the aforementioned gas chromatography to obtain a released amount of the allethrin insecticidal ingredient per time. A value shown in Table 29 is expressed by a relative ratio, letting an initial value of each preparation to be 1.00.

TABLE 29

|  | Insecticide | Lapsed days | | | | |
| --- | --- | --- | --- | --- | --- | --- |
|  |  | Initial | 10 days | 20 days | 30 days | 60 days |
| Example 67 | U1 | 1.00 | 1.00 | 1.00 | 0.99 | 0.97 |
| Example 68 | U2 | 1.00 | 1.00 | 0.99 | 0.97 | 0.95 |
| Example 69 | U3 | 1.00 | 1.00 | 0.98 | 0.96 | 0.94 |
| Comparative Example 100 | U'-1 | 1.00 | 0.95 | 0.91 | 0.90 | 0.62 |
| Comparative Example 101 | U'-2 | 1.00 | 0.51 | 0.31 | 0.11 | 0.03 |
| Comparative Example 102 | U'-3 | 1.00 | 0.72 | 0.54 | 0.35 | 0.20 |
| Comparative Example 103 | U'-4 | 1.00 | 0.93 | 0.92 | 0.91 | 0.65 |

[Insecticidal Test]

(Insecticidal Test of Empenthrin by Normal Temperature Volatilization)

Each of insecticides of Examples 67 to 69, and Comparative Examples 100 to 103 was placed into a container having an inner volume of about 10L and equipped with a glass lid. Further, 100 clothes moth larvae together with a wool were placed into an about 1 L stainless container, this was accommodated into the container equipped with a glass lid, and allowed to stand in a constant temperature constant humidity bath retained at 25° C. ·70% RH, and the number of clothes moth larvae which died 1, 5, 10, 20 and 30 days later was measured. The results are shown in Table 30.

TABLE 30

|  | Insecticide | Lapsed days | | | | |
| --- | --- | --- | --- | --- | --- | --- |
|  |  | Initial | 5 days | 10 days | 20 days | 30 days |
| Example 67 | U1 | 10 | 90 | 100 | 100 | 100 |
| Example 68 | U2 | 15 | 95 | 100 | 100 | 100 |
| Example 69 | U3 | 12 | 92 | 100 | 100 | 100 |
| Comparative Example 100 | U'-1 | 5 | 10 | 14 | 18 | 21 |
| Comparative Example 101 | U'-2 | 1 | 4 | 5 | 6 | 7 |
| Comparative Example 102 | U'-3 | 5 | 20 | 30 | 35 | 40 |
| Comparative Example 103 | U'-4 | 10 | 40 | 60 | 70 | 80 |

(Insecticidal Test of Allethrin by Heating Release)

Insecticides of Examples 67 to 69, and Comparative Examples 100 to 103 were assessed for knock down effect against a common gnat every predetermined time by the following continuous airing method. A value shown in Table 31 is expressed by a relative effective ratio of the number of a common gnat knocked down by the test sample, letting an initial value of the number of a common gnat knocked down by a one day mat containing 40 mg of dl, d-cis, trans-allethrin (previous mat) to be 1.00.

Continuous airing method: Plastic cylinders having an internal diameter of 20 cm and a height of 43 cm were piled in two layers, a cylinder having an internal diameter of 20 cm and a height of 20 cm which is divided into an upper part and a lower part with a wire net having a sieve opening of 1 mm (place for housing a test mosquito) is placed thereon, and a cylinder having an internal diameter of 20 cm and a height of 20 cm is placed thereon. These 4-layered cylinders were placed on a stand, a heating release apparatus is placed on a center of a stand, about 20 test mosquitoes are released in a test cylinder, and the number of knocked out mosquitoes is observed with time. Twenty minutes after exposure, all test mosquitoes are transferred to a clean polyethylene container, a 3% aqueous sugar is given, and a rate of dead insects is examined after 24 hours storage.

TABLE 31

|  | Insecticide | Lapsed days | | | | |
| --- | --- | --- | --- | --- | --- | --- |
|  |  | Initial | 10 days | 20 days | 30 days | 60 days |
| Example 67 | U1 | 1.48 | 1.45 | 1.44 | 1.38 | 1.21 |
| Example 68 | U2 | 1.45 | 1.40 | 1.37 | 1.30 | 1.15 |
| Example 69 | U3 | 1.47 | 1.41 | 1.32 | 1.21 | 1.12 |
| Comparative Example 100 | U'-1 | 1.24 | 1.15 | 1.08 | 1.02 | 0.51 |
| Comparative Example 101 | U'-2 | 1.49 | 0.53 | 0.23 | 0.12 | 0.03 |
| Comparative Example 102 | U'-3 | 1.29 | 0.87 | 0.52 | 0.28 | 0.15 |
| Comparative Example 103 | U'-4 | 1.24 | 1.17 | 1.13 | 1.12 | 0.52 |

From Table 25 to Table 31, the following is apparent.

(1) The insecticidal composition of the present invention has a remarkably higher liquid absorbing amount and liquid holding amount for an organic solvent such as ethanol, methanol, phenoxyethanol and the like containing a pyrethroid insecticidal ingredient as compared with the comparative insecticidal compositions.

(2) In the integrated gelated-type insecticidal composition of the present invention, a gel containing an organic solvent such as ethanol or the like containing a pyrethroid insecticide has a high strength and is firm even at the low concentration of a non-aqueous absorbent, and is remarkably excellent in stability with time, as compared with the comparative integrated gelated-type insecticidal compositions.

(3) The insecticide of the present invention exerts the equal or superior volatilization or release rate of an insecticidal ingredient as compared with the previous insecticides. Further, regarding the insecticidal effect, the insecticide of the present invention can exert performance equal to or superior over that of the previous products over a long term.

(Fuel Batteries Using Fuel Stores)

EXAMPLE 70

A gel-like fuel store in which 1 g of the non-aqueous absorbent in the fuel store (BA1) obtained in Example 10 had absorbed a 50% aqueous methanol solution to saturate, was accommodated in an aluminum can, at least a part of which was provided with a fuel supply valve (methanol gas permeability of 0.0001 g/m$^2$ under RH50%, 40° C. and 24 hours), to obtain the fuel store (H1) of the present invention.

EXAMPLE 71

According to the same manner as that of Example 70 except that the sheet-type fuel store (BD1) obtained in Example 14 was cut into 5×5 cm, and four pieces were used in place of the non-aqueous absorbent in the fuel store (H1), the fuel store (H2) of the present invention was obtained.

EXAMPLE 72

According to the same manner as that of Example 70 except that the integrated gelated-type fuel store (BC4) obtained in Example 13 was used in place of the non-aqueous absorbent in the fuel store (H1) and a 50% aqueous methanol solution, the fuel store (H3) of the present invention was obtained.

COMPARATIVE EXAMPLE 104

According to the same manner as that of Example 70 except that the non-aqueous absorbent in the fuel store (BA'-1) of Comparative Example 14 was used in place of the non-aqueous absorbent in the fuel store (H1), the comparative fuel store (H'-1) was obtained.

COMPARATIVE EXAMPLE 105

According to the same manner as that of Example 70 except that the sheet-type fuel store (BD'-1) of Comparative Example 23 was cut into 5×5 cm, and four pieces were used in place of the non-aqueous absorbent in the fuel store (H1), the comparative fuel store (H'-2) was obtained.

COMPARATIVE EXAMPLE 106

According to the same manner as that of Example 70 except that the fuel store (BC'-8) of Comparative Example 22 was used in place of the non-aqueous absorbent in the fuel store (H1) and a 50% aqueous methanol solution, the comparative fuel store (H'-3) was obtained.

COMPARATIVE EXAMPLE 107

Separately, in order to prepare a fuel store, according to the method described in Example of JP-B No. 4-13828, 1 g of dextrin was dissolved in 5 g of distilled water, and 10 g of methanol was added thereto to obtain powders. The powders were accommodated in an aluminum can described in Example 70 to obtain the comparative fuel store (H'-4).

COMPARATIVE EXAMPLE 108

According to the same manner as that of Example 70 except that a bag made of a polypropylene non-woven fabric (methanol gas permeability of 15.0 g/m$^2$ under RH50%, 40° C. and 24 hours) was used in place of the aluminum can, the comparative fuel store (H'-5) was obtained.

Regarding the fuel stores (H1) to (H3) of the present invention of Examples 70 to 72 and the fuel stores (H'-1) to (H'-5) of Comparative Examples 104 to 108, a volatilization test of liquid fuel and a discharge test were performed by the following methods. The results are shown in Table 32.

[Volatilization Test of Liquid Fuel for Fuel Battery]

Each fuel store was heated to 40° C., decrease in a weight of the fuel store was measured to obtain an amount of the volatilized liquid fuel, and a remaining weight rate of the liquid fuel was obtained by the following equation.

Remaining weight rate (%)=(weight of fuel store before heating/weight of fuel store after heating)×100

[Discharge Test]

A mixture containing 30 parts by weight of platinum black and 3.5 parts by weight of polytetrafluoroethylene was coated on a platinum net, and fired at 300° C. for 30 minutes in nitrogen gas to prepare an anode (fuel electrode). Separately, a mixture containing 30 parts by weight of platinum black and 7.5 parts by weight of polytetrafluoroethylene was coated on a platinum net, a porous sheet of polytetrafluoroethylene (waterproofing membrane) was overlaid on one side of the coated net, this was pressed at a pressure of 300 kg/cm$^2$, and baked at a temperature of 300° C. for 30 minutes in nitrogen to prepare a cathode (air electrode). Then, using the aforementioned both electrodes, a cation exchange membrane (Nafion425 manufactured by Du Pond) as a separator, and a 1.5 mol/l aqueous sulfuric aced solution as an electrolyte solution, a fuel battery provided with a line for sending a fuel to an anode and a fuel supply port was prepared.

Each of the fuel stores of Examples 70 to 72, and Comparative Examples 104 to 108 was mounted in the fuel supply port, a fuel supply valve was opened while pressing the fuel store, a fuel battery was operated at a discharge current density of 40 mA/cm$^2$ and at an operation temperature of room temperature, and a discharge time was measured. In addition, the presence or the absence of fuel leakage after operation was confirmed visually, and assessed by the following criteria.

TABLE 32

| | Fuel store | Remaining weight rate of alcohol fuel (%) | | | | | Discharge time | Presence or absence of fuel leakage |
| --- | --- | --- | --- | --- | --- | --- | --- | --- |
| | | Initiation date | After 2 weeks | After 1 month | After 2 months | After 3 months | | |
| Example 70 | H-1 | 100 | 99.99 | 99.99 | 99.99 | 99.99 | 62 hours | ◯ |
| Example 71 | H-2 | 100 | 99.98 | 99.98 | 99.97 | 99.97 | 58 hours | ◯ |
| Example 72 | H-3 | 100 | 99.99 | 99.99 | 99.99 | 99.99 | 20 hours | ◯ |
| Comparative Example 104 | H'-1 | 100 | 99.98 | 99.97 | 99.97 | 99.96 | 4 hours | X |
| Comparative Example 105 | H'-2 | 100 | 99.98 | 99.98 | 99.97 | 99.97 | 2 hours | X |
| Comparative Example 106 | H'-3 | 100 | 99.97 | 99.96 | 99.95 | 99.95 | 20 hours | X |
| Comparative Example 107 | H'-4 | 100 | 99.96 | 99.95 | 99.93 | 99.93 | 2 hours | Δ |
| Comparative Example 108 | H'-5 | 100 | 0 | 0 | 0 | 0 | 45 hours | ◯ |

◯ No fuel leakage
Δ Slight leakage
X Leaked, and surrounding is polluted.

EXAMPLE 73

A fuel supply line of the aforementioned fuel battery prepared in the aforementioned discharge test was filled with the non-aqueous absorbent in the fuel store (BA1) of Example 10 and a mixed fuel of methanol/water=50/50 to obtain the fuel battery (J1) of the present invention.

COMPARATIVE EXAMPLE 109

According to the same manner as that of Example 73 except that the non-aqueous absorbent in the fuel store (BA1) of Example 10 was not used, the comparative fuel battery (J'-1) was obtained.

COMPARATIVE EXAMPLE 110

According to the same manner as that of Example 73 except that the non-aqueous absorbent in the fuel store (BA'-1) of Comparative Example 14 was used in place of the non-aqueous absorbent in the fuel store (BA1) of Example 10, the comparative fuel battery (J'-2) was obtained.

Regarding the fuel batteries of Example 73, and Comparative Examples 109 and 110, the aforementioned discharge test was performed, and thereafter, operation was stopped and, one week later, re-operation was performed. A variation in output at re-operation one week after was confirmed, and assessed by the following criteria. The results are shown in Table 33.

TABLE 33

| | Fuel battery | Line filler | Variation in output |
| --- | --- | --- | --- |
| Example 73 | J1 | H1 | ◯ |
| Comparative Example 109 | J'-1 | None | X |
| Comparative Example 110 | J'-2 | H'-1 | X |

◯: No variation in output
Δ: Slight variation in output
X: Variation in output

EXAMPLE 74

The sheet-type fuel store (BD1) of Example 14 was arranged between an electrode and a cation exchange membrane of the aforementioned fuel battery prepared for the aforementioned discharge test, to obtain the fuel battery (K1) of the present invention.

COMPARATIVE EXAMPLE 111

According to the same manner as that of Example 74 except that the sheet-type fuel store (BD1) of Example 14 was not used, the comparative fuel battery (K'-1) was obtained.

COMPARATIVE EXAMPLE 112

According to the same manner as that of Example 74 except that the sheet-type fuel store (BD'-1) of Comparative Example 23 was used in place of the sheet-type fuel store (BD1) of Example 14, the comparative fuel battery (K'-2) was obtained.

Regarding the fuel batteries of Example 74, and Comparative Examples 111 and 112, the aforementioned discharge test was performed, and a battery voltage at a discharge current of 40 mA/cm, and at a discharge current of 40 mA/cm$^2$ was measured. The results are shown in Table 34.

TABLE 34

| | Fuel battery | Sheet used | Battery voltage (V) |
| --- | --- | --- | --- |
| Example 74 | K1 | BD1 | 0.50 |
| Comparative Example 111 | K'-1 | None | 0.35 |
| Comparative Example 112 | K'-2 | BD'-1 | 0.35 |

From Tables 32 to 34, the following is apparent.

(1) In the fuel battery of the present invention, since a fuel in a line is also gelated, there can be provided a fuel battery in which bubbles generation during operation stop and bubbles generation due to exothermic heat at operation do not occur, and a fuel supply amount is stable even at re-operation.

(2) Since the fuel battery of the present invention is provided with the sheet-type fuel store of the present invention, crossover of methanol can be prevented, and deterioration in properties of an air electrode can be prevented. For this reason, there can be provided a high performance fuel battery in which a battery voltage is not reduced.

INDUSTRIAL APPLICABILITY

The non-aqueous absorbent of the present invention exerts the following effects.

(i) Since the non-aqueous absorbent of the present invention has a remarkably higher liquid absorbing amount for various organic solvents as compared with previous non-aqueous absorbents, the absorbent can gelate a large amount of an organic solvent by addition of an extremely small amount. In addition, since the non-aqueous absorbent of the present invention also has a high liquid holding amount, the absorbent does not release an absorbed organic solvent even when some slight pressure is applied.

(ii) Since the non-aqueous absorbent sheet of the present invention has a remarkably higher liquid absorbing amount and liquid holding amount for organic solvents as compared with the previous sheets, and hardly releases an absorbed organic solvent even when a pressure is applied more or less, the sheet can absorb/hold a large amount of organic solvent in a short time even when a thickness of a sheet or a total area is small.

(iii) Since when the non-aqueous absorbent sheet of the present invention is used as an electrode solution leakage-preventing sheet for such as an organic solvent system battery or a condenser, even an extremely thin sheet having a small area can absorb/hold a large amount of organic solvent in a short time, and has low strike-through, there is no possibility that, when leakage of an electrolyte solution occurs, an electrolyte solution does not pollute other part, or is exposed to the outside.

(iv) The non-aqueous gel of the present invention is such that a non-aqueous absorbent and an organic solvent are integrated, and can be sufficiently applied to package less utilities such as a solid fuel and a gel battery.

(v) Further, since the non-aqueous gel of the present invention has a high strength and is firm when a pure content of a crosslinked body is low, and can be gelated even in a system containing a large amount of an electrolyte such as a lithium ion, a gel having high electrical conductivity can be obtained.

(vi) Moreover, since a non-aqueous gel comprising a non-aqueous absorbent comprising a crosslinked body and an organic solvent is extremely stable for a long term, there is no fear that a gel is deteriorated, and an electrolyte solution and the like is exposed.

In addition, the similar effect can be exerted in various utilities using the aforementioned non-aqueous absorbent.

(vii) A non-aqueous absorbent in the alcohol-based bactericidal material, the cold insulating material, the gel sheet for cooling, the fuel composition and the solid fuel using the same, the fragrance material, the patch material, the insecticidal composition, the fuel store and the fuel battery using the same of the present invention does not release an absorbed alcohol solvent, fuel battery fuel, aromatic drug, percutaneous absorption drug, pyrethroid insecticidal ingredient or the like even when a pressure is applied more or less. Therefore, the effects (disinfectant•sterilization effect, cold insulating effect, combustion time, aroma effect, inflammatory•analgesic effect, insecticidal effect, long term discharge etc.) can be maintained over a long term.

(viii) Since the sheet-type alcohol-based bactericide, cool insulator, gel sheet for cooling, fuel composition and solid fuel using the same, fragrance, patch, insecticide, fuel store and fuel battery using the same have a remarkably higher liquid absorbing amount for an alcohol solvent, a fuel battery fuel, an aromatic drug, a percutaneous absorption drug, a pyrethroid insecticidal ingredient and the like as compared with the previous sheets, and hardly discharge the aforementioned liquid even when a pressure is applied more or less, they can absorb a large amount of alcohol solvent in a short time even when a thickness of a sheet or a total area is small. For this reason, it becomes possible to prepare a bactericide, a fragrance, a patch, an insecticide or the like in a short time, and the effect thereof can be maintained for a long term. In addition, since strike-through property of a sheet is low when the sheet-type alcohol-based bactericide is used as a food storage sheet, there is no fear that an alcohol solvent pollutes other part, or is exposed to the outside. The gel sheet for cooling retains sufficient softness even under low temperature status and, even when taken out from a refrigerator, the sheet can be used as it is.

(ix) Since the non-aqueous absorbent in the present invention and an alcohol solvent, a fuel battery fuel, an aromatic drug, a percutaneous absorption drug, or a pyrethroid insecticidal ingredient can be used to prepare an integrated gel, the present invention can be sufficiently applied to the aforementioned package less various molded product utilities. In addition, in the case of fuel battery, the present invention can sufficiently satisfy a demand of miniaturization and enhanced performance.

(x) Moreover, since the integrated gelated-type alcohol-based bactericide, cool insulator, solid fuel, fuel store and fuel battery using the same, fragrance, patch and insecticide comprising the non-aqueous absorbent and the aforementioned solvent or drug are extremely stable for a long term, there is no fear that a gel is deteriorated, and the aforementioned liquid is exposed.

(xi) Since the aforementioned various molded products in which the present alcohol-based bactericidal material and/or alcohol-based bactericide, cold insulating material and/or cold insulator, gel sheet for cooling, fuel composition and solid fuel using the same, fuel store and fuel battery using the same, fragrance material and/or fragrance, patch material and/or patch, insecticidal composition and/or insecticide is accommodated in an external material, at least a part of which comprises a steam permeable substrate, have a regulated steam permeation amount, they release a steam of the aforementioned solvent or drug over a long term, they can be suitably used in various utilities for a long term. In addition, the gel sheet for cooling can provide a gel sheet for cooling which is excellent in contact feeling and softness at a low temperature, and easily adhere to a human body. Since when this fuel store is used as a fuel for a fuel battery, volatilization of a fuel steam from the surface can be prevented, it becomes possible to retain a fuel store for a long term and, since there is no fear of fuel leakage, handling becomes dramatically easy and, since there is no fear of fuel leakage after operation of a fuel battery, this is suitable as a fuel for a small fuel battery which is conveniently portable.

(xii) Since a body of the fuel battery of the present invention can be compacted, there is no fear of fuel leakage and long term operation is possible, the fuel battery of the present invention is suitable as a portable fuel battery. Since the fuel battery having a fuel supply line provided with the non-aqueous absorbent of the present invention can prevent generation of bubbles due to exothermic heat at long term operation stoppage or battery operation, a fuel supply amount can be maintained constant, and a fuel battery having no variation in output can be provided. Since the fuel battery having an electrolyte layer provided with the non-aqueous absorbent of the present invention can prevent crossover of methanol, reduction in properties of an air electrode can be prevented and, therefore, a high performance fuel battery can be provided.

What is claimed is:

1. A non-aqueous absorbent (B) comprising a crosslinked polymer (1) which contains 20 to 100% by weight of a structural unit having a carboxyl group and/or a sulfonate group in its molecule, and in which from 50 to 100% by mol of the protons of the carboxyl groups and/or the sulfonate groups have been substituted with one or more onium cations selected from the group consisting of imidazolium cations and imidazolinium cations by reaction with a hydroxide salt or a monomethyl carbonate salt of the onium cation.

2. The non-aqueous absorbent (B) according to claim 1, wherein a content of the structural unit having a carboxyl group and/or a sulfonate group of the polymer (1) is 40 to 100% by weight, and 50 to 100% by mol of protons of the carboxyl group and/or the sulfonate group have been substituted with onium cations.

3. The non-aqueous absorbent (B) according to claim 1, wherein an amount of holding an organic solvent selected from propylene carbonate, γ-butyrolactone, ethanol and methanol is 10 g/g to 1,000 g/g.

4. A non-aqueous gel (C), which comprises the non-aqueous absorbent (B) according to claim 1 and an organic solvent (2).

5. The non-aqueous gel (C) according to claim 4, wherein the organic solvent (2) is one or more selected from the group consisting of an alcohol organic solvent, a glycol organic solvent, a carbonate organic solvent, a ketone organic solvent, an ether organic solvent, an aliphatic hydrocarbon organic solvent, an aromatic hydrocarbon organic solvent, a carboxylic acid ester organic solvent, a lactone organic solvent and a lactam organic solvent.

6. The non-aqueous gel (C) according to claim 4, wherein a polymer (1) which contains 20 to 100% by weight of a structural unit having a carboxyl group and/or a sulfonate group in its molecule and in which from 50 to 100% by mol of protons of the carboxyl group and/or the sulfonate group have been substituted with onium cations is dissolved in the organic solvent (2), and is crosslinked using one or more crosslinking means selected from the group consisting of a crosslinking agent, irradiation with ultraviolet-ray or radiation, and heating.

7. The non-aqueous gel (C) according to claim 4, wherein the gel is obtained by polymerizing 20 to 100% by weight of a monomer which contains a carboxyl group and/or a sulfonate group, and in which from 50 to 100% by mol of protons of the carboxyl group and/or the sulfonate group have been substituted with onium cations and, if necessary, 0 to 80% by weight of other copolymerizable monomer, in the organic solvent (2) in the presence of a crosslinking agent.

8. A non-aqueous absorbent sheet (D), which comprises the non-aqueous absorbent (B) according to claim 1, and a substrate selected from the group consisting of a non-woven fabric, a woven fabric, a paper and a film.

9. The non-aqueous absorbent sheet (D) according to claim 8, wherein the polymer (1) which contains 20 to 100% by weight of a structural unit having a carboxylic acid group and/or a sulfonate group in its molecule, and in which from 50 to 100% by mol of protons of the carboxylic acid group and/or the sulfonate group have been substituted with onium cations, is impregnated into and/or coated on one or more substrates selected from the group consisting of a non-woven fabric, a woven fabric, a paper and a film, and thereafter is crosslinked using one or more crosslinking means selected from the group consisting of a crosslinking agent, irradiation with ultraviolet-ray or radiation, and by heating.

10. The non-aqueous absorbent sheet (D) according to claim 8, wherein a mixed solution containing 20 to 100% by weight of a monomer which contains a carboxyl group and/or a sulfonic group and in which from 50 to 100% by mol of protons of the carboxyl group and/or the sulfonate group have been substituted with onium cations, 0 to 80% by weight of other copolymerizable monomer, and a crosslinking agent is impregnated into and/or coated on one or more substrates selected from the group consisting of a non-woven fabric, a paper, a woven fabric and a film, and thereafter the substrate is polymerized using one or more means selected from the group consisting of a polymerization initiator, irradiation with ultraviolet-ray or radiation, and heating.

11. A non-aqueous absorbent (B) characterized in that a shape of the non-aqueous absorbent (B) according to claim 1 is a particle having an average particle diameter of 1 to 5,000 μm.

12. The non-aqueous absorbent (B) according to claim 1, which is used as a constitutional material for an alcohol-based bactericidal material or an alcohol-based bactericide, a cool insulating material or a cool insulator, a gel sheet for cooling, a fuel composition for solid fuels or a solid fuel using the same, a fragrance material or a fragrance, a patch material or a patch, an insecticidal composition or an insecticide, or a fuel store for fuel batteries or a fuel battery using the same.

13. An alcohol-based bactericidal material or an alcohol-based bactericide, a cool insulating material or a cool insulator, a gel sheet for cooling, or a fuel composition for solid fuels or solid fuel using the same, which comprises the non-aqueous absorbent (B) according to claim 1 and an alcohol solvent.

14. A fragrance material or a fragrance, which comprises the non-aqueous absorbent (B) according to claim 1 and an aromatic drug.

15. A patch material or a patch, which comprises the non-aqueous absorbent (B) according to claim 1 and a percutaneous absorption drug.

16. An insecticidal composition or an insecticide, which comprises the non-aqueous absorbent (B) according to claim 1 and a pyrethroid insecticidal ingredient.

17. A fuel store for fuel batteries or a fuel battery using the same, which comprises the non-aqueous absorbent (B) according to claim 1 and a liquid fuel for fuel batteries.

18. A lithium battery characterized in that the non-aqueous absorbent (B) according to claim 1 is used as a gel electrolyte.

* * * * *